United States Patent
Sato et al.

(10) Patent No.: US 8,126,656 B2
(45) Date of Patent: Feb. 28, 2012

(54) MOLECULAR DESIGN METHOD AND COMPUTER-READABLE STORAGE MEDIUM

(75) Inventors: Hiroyuki Sato, Kawasaki (JP); Azuma Matsuura, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 304 days.

(21) Appl. No.: 12/535,750

(22) Filed: Aug. 5, 2009

(65) Prior Publication Data

US 2009/0292517 A1    Nov. 26, 2009

Related U.S. Application Data

(63) Continuation of application No. PCT/JP2007/052137, filed on Feb. 7, 2007.

(51) Int. Cl.
G06F 19/10    (2011.01)
G06F 19/00    (2006.01)
G06F 19/16    (2006.01)
G01N 31/00    (2006.01)

(52) U.S. Cl. .......................................... 702/27; 702/22

(58) Field of Classification Search ........................ None
See application file for complete search history.

(56) References Cited

U.S. PATENT DOCUMENTS

| | | | |
|---|---|---|---|
| 5,572,439 A | | 11/1996 | Nishida et al. |
| 6,073,080 A | * | 6/2000 | Tomonaga .................... 702/27 |
| 7,188,055 B2 | * | 3/2007 | Agrafiotis et al. ................ 703/2 |
| 2004/0241709 A1 | * | 12/2004 | Patterson ........................... 435/6 |
| 2005/0058975 A1 | * | 3/2005 | Takamatsu ..................... 434/278 |
| 2005/0228592 A1 | * | 10/2005 | Ahuja et al. ..................... 702/19 |
| 2007/0168137 A1 | * | 7/2007 | Duan et al. ...................... 702/19 |
| 2008/0270040 A1 | * | 10/2008 | Fischer et al. .................. 702/19 |
| 2011/0137617 A1 | * | 6/2011 | Desmet et al. .................... 703/1 |

FOREIGN PATENT DOCUMENTS

| | | |
|---|---|---|
| JP | 05-128218 A | 5/1993 |
| JP | 05-174109 A | 7/1993 |
| JP | 05-174110 A | 7/1993 |

OTHER PUBLICATIONS

International Search Report of PCT/JP2007/052137, Mailing Date of May 1, 2007.
CAChe Group, The Chemist's Productivity Tool WinMOPAC for Windows 95 & Windows NT4.0 V2.0, Fujitsu 2002.

* cited by examiner

*Primary Examiner* — Lori A Clow
(74) *Attorney, Agent, or Firm* — Westerman, Hattori, Daniels & Adrian, LLP

(57) ABSTRACT

A computer-implemented molecular design method constructs and stores a data structure including an atomic data structure, a bond axis data structure, a molecular data structure, an auxiliary data structure, and an event data structure, with respect to data of a given three-dimensional (3D) molecular structure. A partial structure that is a modifying target is determined using the data structure, based on an atom or bond axis that is specified. A modified 3D molecular structure in which the partial structure has been subjected to a modifying operation is specified. An Undo or Redo operation is performed on the specified modifying operation using the data structure.

14 Claims, 72 Drawing Sheets

FIG.1

| AUXILIARY DATA STRUCTURE (D) | MOLECULAR DATA STRUCTURE (M) | |
|---|---|---|
| 1. EVENT FLAG (eventFlag)<br>2. ATOMIC NO. (Atom or {CHEMICAL SYMBOL})<br>3. MOLECULE SETTING INFO (mSelect)<br>4. IDENTIFICATION NO. (a) OF ADDED ATOM | 1. ATOMIC DATA NO. (na)<br>2. BOND AXIS DATA NO. (nb)<br>3. TOTAL EVENT OPERATION NO. (ne)<br>4. UNDO EVENT OPERATION NO. (nu)<br>5. ATOMIC DATA (A) WITHIN MOLECULE<br>6. BOND AXIS DATA (B) WITHIN MOLECULE | |
| EVENT DATA STRUCTURE (E) | ATOMIC DATA STRUCTURE (A, A') | BOND AXIS DATA STRUCTURE (B, B') |
| 1. EVENT FLAG (eventFlag)<br>2. SELECTED ATOM NO. (na')<br>3. SELECTED BOND AXIS NO. (nb')<br>4. ADDED ATOM DATA NO. (na)<br>5. ADDED BOND AXIS DATA NO. (nb)<br>6. ATOMIC DATA (A) BEFORE PROCESS<br>7. BOND AXIS DATA (b) BEFORE PROCESS<br>8. ATOMIC DATA (A') AFTER PROCESS<br>9. BOND AXIS DATA (B') AFTER PROCESS | 1. IDENTIFICATION NO. (a)<br>2. ATOMIC NO.<br>(Atom or {CHEMICAL SYMBOL})<br>3. BOND AXIS NO. (nb)<br>4. IDENTIFICATION NO. (b) OF<br>BOND AXIS<br>5. EVENT FLAG (eventFlag)<br>[IDENTIFICATION FLAG]<br>6. xyz COORDINATES (coordinate) | 1. IDENTIFICATION NO. (b)<br>2. IDENTIFICATION NO. (a) OF<br>TERMINAL ATOMS<br>3. EVENT FLAG (eventFlag)<br>[IDENTIFICATION FLAG]<br>4. VECTOR (vector)<br>5. BOND AXIS LENGTH (length) |

FIG.2

| D | M[1] | : {Null, {C}, {CH₄}, 2} |
|---|---|---|
| | M[1]→A[1] | : {1, {C}, 3, {1, 2, 3}, Null,...} |
| | M[1]→A[2] | : {2, {O}, 1, {1}, Null,...} |
| | M[1]→A[3] | : {3, {O}, 2, {2, 4}, Null,...} |
| | M[1]→A[4] | : {4, {H}, 1, {3}, Null,...} |
| | M[1]→A[5] | : {5, {H}, 1, {4}, Null,...} |
| | M[1]→B[1] | : {1, {1, 2}, Null,...} |
| | M[1]→B[2] | : {2, {1, 3}, Null,...} |
| | M[1]→B[3] | : {3, {1, 4}, Null,...} |
| | M[1]→B[4] | : {4, {3, 5}, Null,...} |

| E[1] | M[2] | : {Null, 0, 0, 0, 0, Null, Null,...} |
|---|---|---|
| | M[2] | : {5, 4, 0, 0, {A[5]}, {B[4]}} |
| | M[2]→A[1] | : {1, {C}, 4, {1, 2, 3, 4}, Null,...} |
| | M[2]→A[2] | : {2, {H}, 1, {1}, Null,...} |
| | M[2]→A[3] | : {3, {H}, 1, {2}, Null,...} |
| | M[2]→A[4] | : {4, {H}, 1, {3}, Null,...} |
| | M[2]→A[5] | : {5, {H}, 1, {4}, Null,...} |
| | M[2]→B[1] | : {1, {1, 2}, Null,...} |
| | M[2]→B[2] | : {2, {1, 3}, Null,...} |
| | M[2]→B[3] | : {3, {1, 4}, Null,...} |
| | M[2]→B[4] | : {4, {1, 5}, Null,...} |

M[1] (CONSTRUCTED MOLECULE: HCOOH)

M[2] (ADD EVENT SETTING MOLECULE: CH₄)

FIG.6
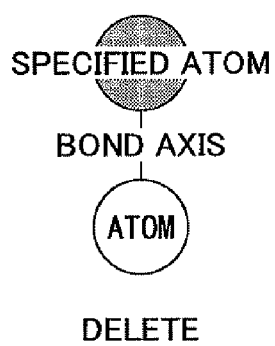
DELETE
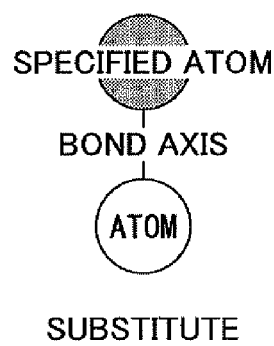
SUBSTITUTE
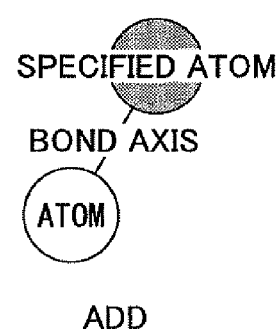
ADD
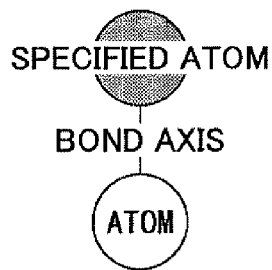 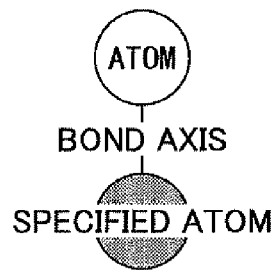
NEW BOND
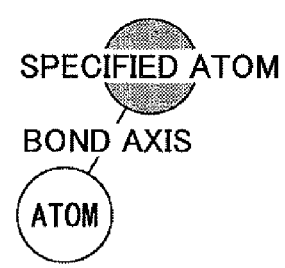
NEW ATOM

FIG.10

1. SET KIND OF EVENT IN "D→eventFlag"
2. "Select" "M→A→eventFlag" OR "M→B→eventFlag"
3. REGISTER KIND OF EVENT OF "D→eventFlag" TO "E→eventFlag"
4. EXECUTE "E→eventFlag" EVENT FOR "M→A" OR "M→B" OF "Select" STATE

FIG.11

"M→A→eventFlag = Delete" : DELETE A FROM OPERATION SCREEN OF MOLECULAR DESIGN SUPPORT SYSTEM
"M→B→eventFlag = Delete" : DELETE B FROM OPERATION SCREEN OF MOLECULAR DESIGN SUPPORT SYSTEM

FIG.12

"M→ne" : TOTAL EVENT OPERATION NO. REGISTERED AND CONSTRUCTING M (NO. OF UNDO OPERATIONS POSSIBLE)
"M→nu" : PRESENT UNDO EVENT OPERATION NO. CONSTRUCTING M (NO. OF REDO OPERATIONS POSSIBLE)
"M→ne − M→nu + 1": PRESENT EVENT NO. CONSTRUCTING M

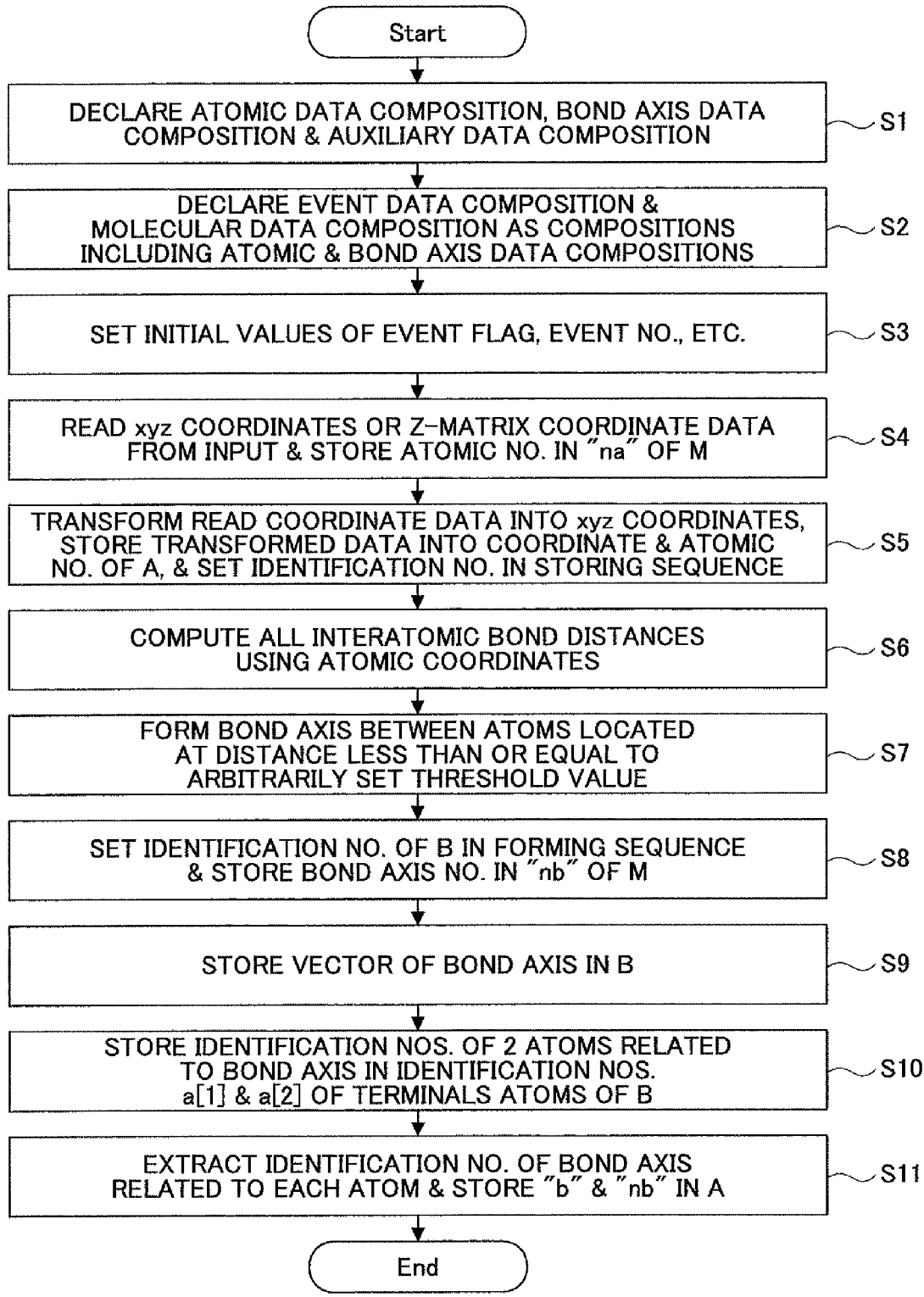

FIG. 14

○ BEFORE DELETE EVENT
E[1]       : {Null, 0, 0, 0, 0, {Null}, {Null}, {Null}}
M[1]       : {5, 4, 0, 0, {A[5]}, {B[4]}}

○ USER INPUT   : D→eventFlag = Delete
                 M[1]→A[4]→eventFlag = Select ○ DELETE EVENT OPERATION
M[1]→A[4]→eventFlag = D→eventFlag
M[1]→B[3]→eventFlag = D→eventFlag
M[1]→ne = M[1]→ne − M[1]→nu + 1
M[1]→nu = 0
E[En] = {Null}        (En >= M[1]→ne)
E[M[1]→ne]→eventFlag = D→eventFlag
M[1]→ne]→na' = 2
M[1]→ne]→nb' = 1
E[M[1]→ne]→A[1] =
                M[1]→A[M[1]→B[3]→a[1]]
E[M[1]→ne]→A[2] =
                M[1]→A[M[1]→B[3]→a[2]]

E[M[1]→ne]→B[1] = M[1]→B[3]
E[M[1]→ne]→A[1]→eventFlag = Null
E[M[1]→ne]→A[2]→eventFlag = Null
E[M[1]→ne]→B[1]→eventFlag = Null
M[1]→A[M[1]→B[3]→a[1]]→b = {1, 2}
M[1]→A[M[1]→B[3]→a[2]]→b = {Null}
M[1]→A[M[1]→B[3]→a[1]]→nb = 2
M[1]→A[M[1]→B[3]→a[2]]→nb = 0
E[M[1]→ne]→A'[1] =
                M[1]→A[M[1]→B[3]→a[1]]
E[M[1]→ne]→A'[2] =
                M[1]→A[M[1]→B[3]→a[2]]
E[M[1]→ne]→B'[1] = M[1]→B[3]

○ AFTER DELETE EVENT
E[1]       : {Delete, 2, 1, 0, 0, {A[2]}, {B[1]}, {A'[2]}, {B'[1]}}
M[1]       : {5, 4, 1, 0, {A[5]}, {B[4]}}
M[1]→A[1]  : {1, {C}, 2, {1, 2}, Null, Delete, {$x_{A1}$, $y_{A1}$, $z_{A1}$}}
M[1]→A[4]  : {4, {H}, 0, {Null}, Delete, {$x_{A4}$, $y_{A4}$, $z_{A4}$}}
M[1]→B[3]  : {3, {1, 4}, Delete, {$x_{B3}$, $y_{B3}$, $z_{B3}$}, length_B3}

FIG.15

```
○ BEFORE UNDO OPERATION (AFTER DELETE)
E[1]        : {Delete, 2, 1, 0, 0, {A[2]}, {B[1]}, {A'[2]}, {B'[1]}}
E[1]→A[1]   : {1, {C}, 3, {1, 2, 3}, Null, {$x_{A1}$, $y_{A1}$, $z_{A1}$}}
E[1]→A[2]   : {4, {H}, 1, {3}, Null, {$x_{A4}$, $y_{A4}$, $z_{A4}$}}
E[1]→B[1]   : {3, {1, 4}, Null, {$x_{B3}$, $y_{B3}$, $z_{B3}$}, length_B3}
M[1]        : {5, 4, 1, 0, {A[5]}, {B[4]}}
M[1]→A[1]   : {1, {C}, 2, {1, 2}, Null, {$x_{A1}$, $y_{A1}$, $z_{A1}$}}
M[1]→A[4]   : {4, {H}, 0, {Null}, Delete, {$x_{A4}$, $y_{A4}$, $z_{A4}$}}
M[1]→B[3]   : {3, {1, 4}, Delete, {$x_{B3}$, $y_{B3}$, $z_{B3}$}, length_B3}

○ USER INPUT    : D→eventFlag = Undo

○ UNDO OPERATION
M[1]→nu = M[1]→nu + 1
E1 = M[1]→ne − M[1]→nu + 1
M[1]→A[E[E1]→A[1]→a] = E[E1]→A[1]
M[1]→A[E[E1]→A[2]→a] = E[E1]→A[2]
M[1]→B[E[E1]→B[1]→b] = E[E1]→B[1]

○ AFTER UNDO OPERATION
M[1]        : {5, 4, 1, 1, {A[5]}, {B[4]}}
M[1]→A[1]   : {1, {C}, 3, {1, 2, 3}, Null, {$x_{A1}$, $y_{A1}$, $z_{A1}$}}
M[1]→A[4]   : {4, {H}, 1, {3}, Null, {$x_{A4}$, $y_{A4}$, $z_{A4}$}}
M[1]→B[3]   : {3, {1, 4}, Null, {$x_{B3}$, $y_{B3}$, $z_{B3}$}, length_B3}
```

FIG.16

○ BEFORE REDO OPERATION (DELETE→AFTER UNDO)
E[1]
E[1]→A'[1] : {Delete, 2, 1, 0, 0, {A[2]}, {B[1]}, {A'[2]}, {B'[1]}}
E[1]→A'[2] : {1, {C}, 2, {1, 2}, Null, {$x_{A1}$, $y_{A1}$, $z_{A1}$}}
E[1]→B'[1] : {4, {H}, 0, {Null}, Delete, {$x_{A4}$, $y_{A4}$, $z_{A4}$}}
M[1] : {3, {1, 4}, Delete, {$x_{B3}$, $y_{B3}$, $z_{B3}$}, length_B3}
M[1]→A[1] : {5, 4, 1, 1, {A[5]}, {B[4]}}
M[1]→A[2] : {1, {C}, 3, {1, 2, 3}, Null, {$x_{A1}$, $y_{A1}$, $z_{A1}$}}
M[1]→A[4] : {4, {H}, 1, {3}, Null, {$x_{A4}$, $y_{A4}$, $z_{A4}$}}
M[1]→B[3] : {3, {1, 4}, Null, {$x_{B3}$, $y_{B3}$, $z_{B3}$}, length_B3}

○ USER INPUT : D→eventFlag = Redo

○ REDO OPERATION
E1 = M[1]→ne − M[1]→nu + 1
M[1]→nu = M[1]→nu − 1
M[1]→A[E[E1]→a] = E[E1]→A'[1]
M[1]→A[E[E1]→a] = E[E1]→A'[2]
M[1]→B[E[E1]→b] = E[E1]→B'[1]

○ AFTER REDO OPERATION
M[1] : {5, 4, 1, 0, {A[5]}, {B[14]}}
M[1]→A[1] : {1, {C}, 2, {1, 2}, Null, {$x_{A1}$, $y_{A1}$, $z_{A1}$}}
M[1]→A[4] : {4, {H}, 0, {Null}, Delete, {$x_{A4}$, $y_{A4}$, $z_{A4}$}}
M[1]→B[3] : {3, {1, 4}, Delete, {$x_{B3}$, $y_{B3}$, $z_{B3}$}, length_B3}

FIG.19

M[1] (BEFORE DELETE)

| M[1] | : {5, 4, 0, 0, {A[5]}, {B[4]}} |
|---|---|
| M[1]→A[1] | : {1, {C}, 3, {1, 2, 3}, Null,...} |
| M[1]→A[2] | : {2, {O}, 1, {1}, Null,...} |
| M[1]→A[3] | : {3, {O}, 2, {2, 4}, Select,...} |
| M[1]→A[4] | : {4, {H}, 1, {3}, Null,...} |
| M[1]→A[5] | : {5, {H}, 1, {4}, Null,...} |
| M[1]→B[1] | : {1, {1, 2}, Null,...} |
| M[1]→B[2] | : {2, {1, 3}, Null,...} |
| M[1]→B[3] | : {3, {1, 4}, Null,...} |
| M[1]→B[4] | : {4, {3, 5}, Null,...} |

M[1] (AFTER DELETE)

| M[1] | : {5, 4, 1, 0, {A[5]}, {B[4]}} |
|---|---|
| M[1]→A[1] | : {1, {C}, 2, {1, 3}, Null,...} |
| M[1]→A[2] | : {2, {O}, 1, {1}, Null,...} |
| M[1]→A[3] | : {3, {O}, 0, {Null}, Delete,...} |
| M[1]→A[4] | : {4, {H}, 1, {3}, Null,...} |
| M[1]→A[5] | : {5, {H}, 0, {Null}, Null,...} |
| M[1]→B[1] | : {1, {1, 2}, Null,...} |
| M[1]→B[2] | : {2, {1, 3}, Delete,...} |
| M[1]→B[3] | : {3, {1, 4}, Null,...} |
| M[1]→B[4] | : {4, {3, 5}, Delete,...} |

FIG. 26

○ BEFORE SUBSTITUTE EVENT (DELETE→AFTER UNDO)
D    : {Null, {C}, {CH₄}, 2}
E[1] : {Delete, 2, 1, 0, 0, {A[2]}, {B[1], {A'[2]}, {B'[1]}}
M[1] : {5, 4, 1, 1, {A[5]}, {B[4]}}
M[1]→A[2] : {2, {O}, 1, {1}, Null, {x_{A2}, y_{A2}, z_{A2}}}
M[1]→B[1] : {1, {1, 2}, Null, {x_{B1}, y_{B1}, z_{B1}}, length_B1}

○ USER INPUT : D→eventFlag = Substitute
              : M[1]→A[2]→eventFlag = Select ○ SUBSTITUTE EVENT OPERATION
M[1]→A[2]→eventFlag = D→eventFlag          M[1]→A[2]→Atom = D→Atom
M[1]→B[1]→eventFlag = D→eventFlag          M[1]→B[1]→vector = {x'_{B1}, y'_{B1}, z'_{B1}}
M[1]→ne = M[1]→ne − M[1]→nu + 1            M[1]→B[1]→length = length'_B1
M[1]→nu = 0                                 M[1]→A[2]→eventFlag = Null
E[En] = {Null}      (En >= M[1]→ne)        M[1]→B[1]→eventFlag = Null
E[M[1]→ne]→eventFlag = D→eventFlag          E[M[1]→ne]→A[1]→eventFlag = Null
E[M[1]→ne]→na' = 1                          E[M[1]→ne]→B[1]→eventFlag = Null
E[M[1]→ne]→nb' = 1                          E[M[1]→ne]→A'[1] = M[1]→A[2]
E[M[1]→ne]→A[1] = M[1]→A[2]                 E[M[1]→ne]→B'[1] = M[1]→B[1]
E[M[1]→ne]→B[1] = M[1]→B[1]                 E[M[1]→ne]→A[2]→coordinate = {x'_{A2}, y'_{A2}, z'_{A2}}

○ AFTER SUBSTITUTE EVENT
E[1] : {Substitute, 1, 1, 0, 0, {A[1]}, {B[1], {A'[1]}, {B'[1]}}}
M[1] : {5, 4, 1, 0, {A[5]}, {B[4]}}
M[1]→A[2] : {2, {C}, 1, {1}, Null, {x'_{A2}, y'_{A2}, z'_{A2}}}
M[1]→B[1] : {1, {1, 2}, Null, {x'_{B1}, y'_{B1}, z'_{B1}}, length'_B1}

FIG.27

○ BEFORE UNDO OPERATION (DELETE→UNDO→AFTER SUBSTITUTE)

E[1]     : {Substitute, 1, 1, 0, 0, {A[1]}, {B[1]}, {A'[1]}, {B'[1]}}
E[1]→A[1] : {2, {O}, 1, {1}, Null, {$x_{A2}$, $y_{A2}$, $z_{A2}$}}
E[1]→B[1] : {1, {1, 2}, Null, {$x_{B1}$, $y_{B1}$, $z_{B1}$}, length_B1}
M[1]      : {5, 4, 1, 0, {A[5]}, {B[4]}}
M[1]→A[2] : {2, {C}, 1, {1}, Null, {$x'_{A2}$, $y'_{A2}$, $z'_{A2}$}}
M[1]→B[1] : {1, {1, 2}, Null, {$x'_{B1}$, $y'_{B1}$, $z'_{B1}$}, length'_B1}

○ USER INPUT : D→eventFlag = Undo

○ UNDO OPERATION
M[1]→nu = M[1]→nu + 1
E1 = M[1]→ne − M[1]→nu + 1
M[1]→A[E[E1]→a] = E[E1]→A[1]
M[1]→B[E[E1]→b] = E[E1]→B[1]
M[1]→A[1~M[1]→na]→coordinate = {$x_{A1~AM[1]→na}$, $y_{A1~AM[1]→na}$, $z_{A1~AM[1]→na}$}

○ AFTER UNDO OPERATION
M[1]      : {5, 4, 1, 1, {A[5]}, {B[4]}}
M[1]→A[2] : {2, {O}, 1, {1}, Null, {$x_{A2}$, $y_{A2}$, $z_{A2}$}}
M[1]→B[1] : {1, {1, 2}, Null, {$x_{B1}$, $y_{B1}$, $z_{B1}$}, length_B1}

FIG.28

○BEFORE REDO OPERATION (DELETE→UNDO→SUBSTITUTE→AFTER UNDO)
E[1]         : {Substitute, 1, 1, 0, 0, {A[1]}, {B[1]}, {A'[1]}, {B'[1]}}
E[1]→A'[1]   : {2, {C}, 1, {1}, Null, {x'$_{A2}$, y'$_{A2}$, z'$_{A2}$}}
E[1]→B'[1]   : {1, {1, 2}, Null, {x'$_{B1}$, y'$_{B1}$, z'$_{B1}$}, length'_B1}
M[1]         : {5, 4, 1, 1, {A[5]}, {B[4]}}
M[1]→A[2]    : {2, {O}, 1, {1}, Null, {x$_{A2}$, y$_{A2}$, z$_{A2}$}}
M[1]→B[1]    : {1, {1, 2}, Null, {x$_{B1}$, y$_{B1}$, z$_{B1}$}, length_B1}

○USER INPUT  : D→eventFlag = Redo

○REDO OPERATION
E1 = M[1]→ne − M[1]→nu + 1
M[1]→nu = M[1]→nu − 1
M[1]→A[E[E1]→A'[1]→a] = E[E1]→A'[1]
M[1]→B[E[E1]→B'[1]→b] = E[E1]→B'[1]
M[1]→A[1~M[1]→na]→coordinate =
{x'$_{A1~AM[1]→na}$, y'$_{A1~AM[1]→na}$, z'$_{A1~AM[1]→na}$}

○AFTER REDO OPERATION
M[1]         : {5, 4, 1, 0, {A[5]}, {B[14]}}
M[1]→A[2]    : {2, {C}, 1, {1}, Null, {x'$_{A2}$, y'$_{A2}$, z'$_{A2}$}}
M[1]→B[1]    : {1, {1, 2}, Null, {x'$_{B1}$, y'$_{B1}$, z'$_{B1}$}, length'_B1}

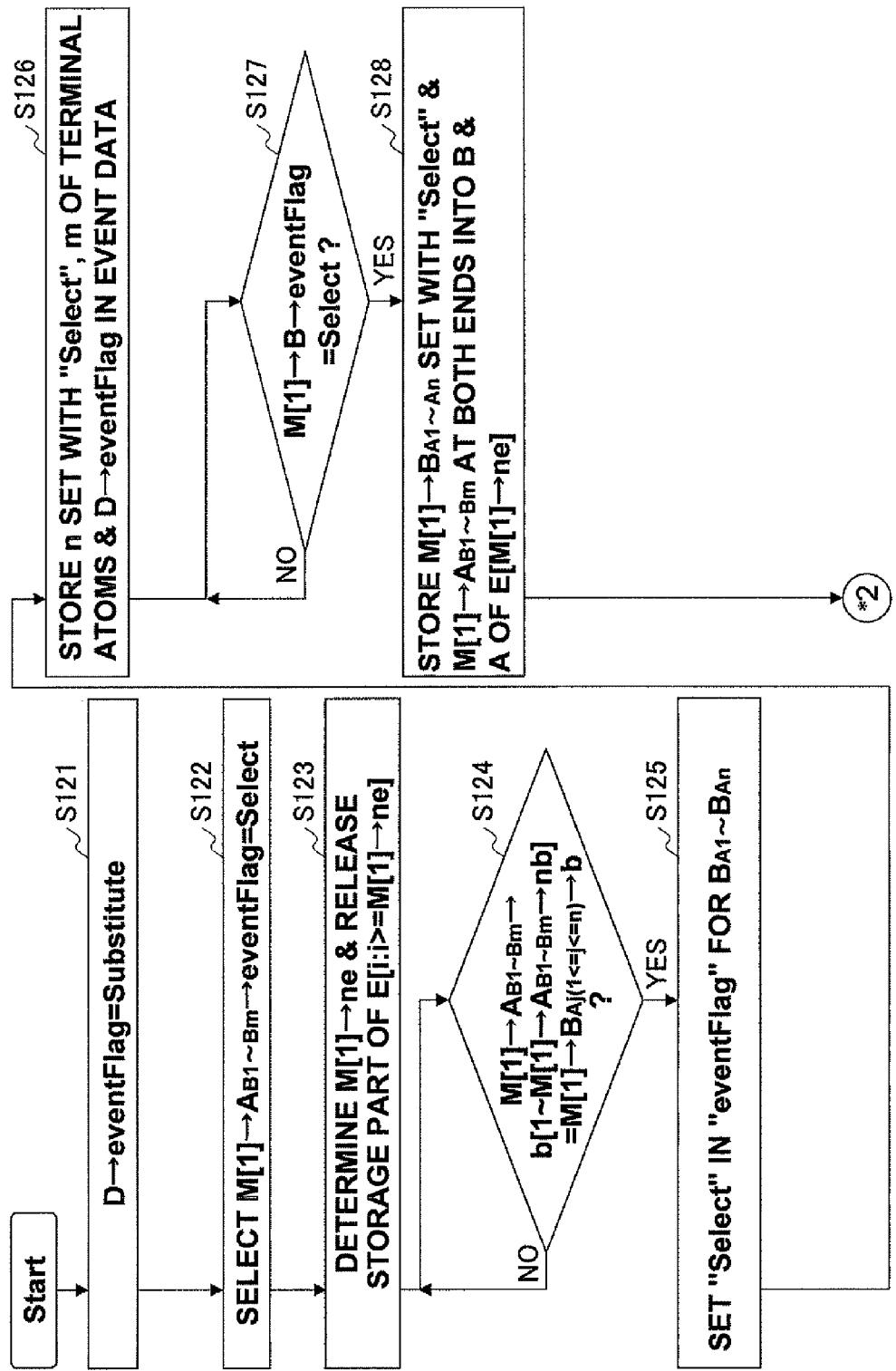

FIG. 38

○ BEFORE ADD EVENT
D     : {Null, {C}, {CH4}, 2}
E[1]  : {Null, 0, 0, 0, 0, {Null}, {Null}, {Null}}
M[1]  : {5, 4, 0, 0, {A[5]}, {B[4]}}

○ USER INPUT     : D→eventFlag = Add
                 : M[1]→A[4]→eventFlag = Select ○ ADD EVENT OPERATION
M[1]→A[4]→eventFlag = Add                                  M[2]→B[m]→length = length'_Bm
M[1]→ne = M[1]→ne − M[1]→nu + 1                            B1 = M[2]→A[D→a]→b[1]
M[1]→nu = 0                                                M[2]→B[B1]→eventFlag = Delete
E[En] = {Null}         (En >= M[1]→ne)                     M[1]→B[M[1]→nb + m] = M[2]→B[m]
E[M[1]→ne]→eventFlag = D→eventFlag                         M[2]→A[n]→coordinate = {x'$_{An}$, y'$_{An}$, z'$_{An}$}
E[M[1]→ne]→na = M[2]→na                                                       (1 <= n <= M[2]→na)
E[M[1]→ne]→nb = M[2]→nb                                    M[2]→A[D→a]→eventFlag = Delete
E[M[1]→ne]→na' = 1                                         M[1]→A[M[1]→na + n] = M[2]→A[n]
E[M[1]→ne]→nb' = 1                                         M[1]→A[4]→eventFlag = Delete
E[M[1]→ne]→A[1] = M[1]→A[4]                                M[1]→B[3]→a = {1, 6}
E[M[1]→ne]→B[1] = M[1]→B[3]                                M[1]→A[6]→b = {3, 6, 7, 8}
M[1]→B[3]→vector = {x'$_{B3}$, y'$_{B3}$, z'$_{B3}$}       M[1]→na = M[1]→na + M[2]→na
M[1]→B[3]→length = length'_B3                              M[1]→nb = M[1]→nb + M[2]→nb
M[2]→B[m]→vector = {x'$_{Bm}$, y'$_{Bm}$, z'$_{Bm}$}       E[M[1]→ne]→A[1]→eventFlag = Null
            (1 <= m <= M[2]→nb)                            E[M[1]→ne]→A'[1] = M[1]→A[4]
                                                           E[M[1]→ne]→B'[1] = M[1]→B[3]

○ AFTER ADD EVENT
M[1]  : {10, 8, 1, 0, {A[10]}, {B[8]}}

FIG.39

○ BEFORE UNDO OPERATION (AFTER ADD)

E[1]      : {Add, 1, 1, 5, 4, {A[1]}, {B[1]}, {A'[1]}, {B'[1]}}
E[1]→A[1] : {4, {H}, 1, {3}, Null, {$x_{A4}$, $y_{A4}$, $z_{A4}$}}
E[1]→B[1] : {3, {1, 4}, Null, {$x_{B3}$, $y_{B3}$, $z_{B3}$}, length_B3}
M[1]      : {10, 8, 1, 0, {A[10]}, {B[8]}}
M[1]→A[4] : {4, {H}, 1, {3}, Delete, {$x_{A4}$, $y_{A4}$, $z_{A4}$}}
M[1]→B[3] : {3, {1, 6}, Null, {x'$_{B3}$, y'$_{B3}$, z'$_{B3}$}, length'_B3}

○ USER INPUT    : D→eventFlag = Undo

○ UNDO OPERATION
M[1]→nu = M[1]→nu + 1
E1 = M[1]→ne − M[1]→nu + 1
M[1]→A[E[E1]→a] = E[E1]→A[1]
M[1]→B[E[E1]→b] = E[E1]→B[1]
M[1]→na = M[1]→na − E[E1]→na
M[1]→nb = M[1]→nb − E[E1]→nb

○ AFTER UNDO OPERATION

M[1]      : {5, 4, 1, 1, {A[10]}, {B[8]}}
E[1]→A[1] : {4, {H}, 1, {3}, Null, {$x_{A4}$, $y_{A4}$, $z_{A4}$}}
E[1]→B[1] : {3, {1, 4}, Null, {$x_{B3}$, $y_{B3}$, $z_{B3}$}, length_B3}

FIG.40

○BEFORE REDO OPERATION (ADD→AFTER UNDO)
E[1]           : {Add, 1, 1, 5, 4, {A[1]}, {B[1]}, {A'[1]}, {B'[1]}}
E[1]→A'[1]     : {4, {H}, 1, {3}, Delete, {$x_{A4}$, $y_{A4}$, $z_{A4}$}}
E[1]→B'[1]     : {3, {1, 6}, Null, {$x'_{B3}$, $y'_{B3}$, $z'_{B3}$}, length'_B3}
M[1]           : {5, 4, 1, 1, {A[10]}, {B[8]}}
M[1]→A[4]      : {4, {H}, 1, {3}, Null, {$x_{A4}$, $y_{A4}$, $z_{A4}$}}
M[1]→B[3]      : {3, {1, 6}, Null, {$x_{B3}$, $y_{B3}$, $z_{B3}$}, length_B3}

○USER INPUT     : D→eventFlag = Redo

○REDO OPERATION
E1 = M[1]→ne − M[1]→nu + 1
M[1]→nu = M[1]→nu − 1
M[1]→A[E[E1]→a] = E[E1]→A'[1]
M[1]→B[E[E1]→b] = E[E1]→B'[1]
M[1]→na = M[1]→na + E[E1]→na
M[1]→nb = M[1]→nb + E[E1]→nb

○AFTER REDO OPERATION
M[1]           : {10, 8, 1, 0, {A[10]}, {B[8]}}
M[1]→A[4]      : {4, {H}, 1, {3}, Delete, {$x_{A4}$, $y_{A4}$, $z_{A4}$}}
M[1]→B[3]      : {3, {1, 6}, Null, {$x'_{B3}$, $y'_{B3}$, $z'_{B3}$}, length'_B3}

FIG. 50

○ BEFORE NEW BOND EVENT
E[1]      : {Null, 0, 0, 0, 0, {Null}, {Null}, {Null}}
M[1]      : {5, 4, 0, 0, {A[5]}, {B[4]}}

○ USER INPUT
D→eventFlag = NewBond
M[1]→A[2]→eventFlag = Select
M[1]→A[3]→eventFlag = Select

○ NEW BOND EVENT OPERATION
M[1]→ne = M[1]→ne − M[1]→nu + 1
M[1]→nu = 0
E[En] = {Null}           (En >= M[1]→ne)
E[M[1]→ne]→eventFlag = D→eventFlag
E[M[1]→ne]→na' = M[1]→A[2]→a
E[M[1]→ne]→nb' = M[1]→A[3]→a
M[1]→nb = M[1]→nb + 1
M[1]→B[M[1]→nb]→b = M[1]→nb
M[1]→B[M[1]→nb]→a[1] = M[1]→A[2]→a
M[1]→B[M[1]→nb]→a[2] = M[1]→A[3]→a
M[1]→A[2]→eventFlag = Null
M[1]→A[3]→eventFlag = Null
M[1]→B[M[1]→nb]→vector =
    M[1]→A[2]→coordinate −
    M[1]→A[3]→coordinate
M[1]→B[M[1]→nb]→length =
    sqrt((M[1]→B[M[1]→nb]→vector)**2)
M[1]→A[2]→nb = M[1]→A[2]→nb + 1
M[1]→A[3]→nb = M[1]→A[3]→nb + 1
M[1]→A[2]→b[M[1]→A[2]→nb] = M[1]→nb
M[1]→A[3]→b[M[1]→A[3]→nb] = M[1]→nb

○ AFTER NEW BOND EVENT
E[1]        : {NewBond, 2, 3, 0, 0, {Null}, {Null}, {Null}}
M[1]        : {5, 5, 1, 0, {A[5]}, {B[5]}}
M[1]→A[2]   : {2, {O}, 2, {1, 5}, Null, {$x_{A2}$, $y_{A2}$, $z_{A2}$}}
M[1]→A[3]   : {3, {O}, 3, {2, 4, 5}, Null, {$x_{A3}$, $y_{A3}$, $z_{A3}$}}
M[1]→B[5]   : {5, {2, 3}, Null, {$x_{B5}$, $y_{B5}$, $z_{B5}$}, length_B5}

FIG.51

○ BEFORE UNDO OPERATION (AFTER NEW BOND)
E[1]                : {NewBond, 2, 3, 0, 0, {Null}, {Null}, {Null}, {Null}}
E[1]→na'            : 2
E[1]→nb'            : 3
M[1]                : {5, 5, 1, 0, {A[5]}, {B[5]}}
M[1]→A[2]           : {2, {O}, 2, {1, 5}, Null, {$x_{A2}$, $y_{A2}$, $z_{A2}$}}
M[1]→A[3]           : {3, {O}, 3, {2, 4, 5}, Null, {$x_{A3}$, $y_{A3}$, $z_{A3}$}}
M[1]→B[5]           : {5, {2, 3}, Null, {$x_{B5}$, $y_{B5}$, $z_{B5}$}, length_B5}

○ USER INPUT        : D→eventFlag = Undo

○ UNDO OPERATION
M[1]→nu = M[1]→nu + 1
E1 = M[1]→ne − M[1]→nu + 1
M[1]→A[E[E1]→na']→nb =
    M[1]→A[E[E1]→na']→nb − 1
M[1]→A[E[E1]→nb']→nb =
    M[1]→A[E[E1]→nb']→nb − 1

M[1]→A[E[E1]→na']→b = {1}
M[1]→A[E[E1]→nb']→b = {2, 4}
M[1]→nb = M[1]→nb − 1

○ AFTER UNDO OPERATION
M[1]                : {5, 4, 1, 1, {A[5]}, {B[5]}}
E[1]→A[2]           : {2, {O}, 1, {1}, Null, {$x_{A2}$, $y_{A2}$, $z_{A2}$}}
E[1]→A[3]           : {3, {O}, 2, {2, 4}, Null, {$x_{A3}$, $y_{A3}$, $z_{A3}$}}

FIG.52

```
○BEFORE REDO OPERATION (NEW BOND→AFTER UNDO)
E[1]        : {NewBond, 2, 3, 0, 0, {Null}, {Null}, {Null}}
E[1]→na'    : 2
E[1]→nb'    : 3
M[1]        : {5, 4, 1, 1, {A[5]}, {B[5]}}
M[1]→A[2]   : {2, {O}, 1, {1}, Null, {xA2, yA2, zA2}}
M[1]→A[3]   : {3, {O}, 2, {2, 4}, Null, {xA3, yA3, zA3}}

○USER INPUT : D→eventFlag = Redo

○REDO OPERATION                                    M[1]→A[E[E1]→na']→b = {1, 5}
E1 = M[1]→ne — M[1]→nu + 1                         M[1]→A[E[E1]→nb']→b = {2, 4, 5}
M[1]→nu = M[1]→nu − 1                              M[1]→nb = M[1]→nb + 1
M[1]→A[E[E1]→na']→b =
     M[1]→A[E[E1]→na']→nb + 1
M[1]→A[E[E1]→nb']→nb =
     M[1]→A[E[E1]→nb']→nb + 1

○AFTER REDO OPERATION
M[1]        : {5, 5, 1, 0, {A[5]}, {B[5]}}
M[1]→A[2]   : {2, {O}, 2, {1, 5}, Null, {xA2, yA2, zA2}}
M[1]→A[3]   : {3, {O}, 3, {2, 4, 5}, Null, {xA3, yA3, zA3}}
M[1]→B[5]   : {5, {2, 3}, Null, {xB6, yB6, zB6}, length_B5}
```

FIG. 62

| | |
|---|---|
| ○BEFORE NEW ATOM EVENT | |
| E[1] | : {Null, 0, 0, 0, 0, {Null}, {Null}, {Null}} |
| M[1] | : {5, 4, 0, 0, {A[5]}, {B[4]}} |
| ○USER INPUT | : D→eventFlag = NewAtom |
| | : M[1]→A[3]→eventFlag = Select |
| ○NEW ATOM EVENT OPERATION | M[1]→B[M[1]→nb]→eventFlag = Null |
| M[1]→ne = M[1]→ne − M[1]→nu + 1 | M[1]→A[3]→eventFlag = Null |
| M[1]→nu = 0 | M[1]→A[M[1]→na]→coordinate = {x,y,z} |
| E[En] = {Null}    (En >= M[1]→ne) | M[1]→B[M[1]→nb]→vector = |
| E[M[1]→ne]→eventFlag = D→eventFlag | M[1]→A[M[1]→na]→coordinate |
| E[M[1]→ne]→na' = M[1]→A[3]→a | − M[1]→A[3]→coordinate |
| M[1]→na = M[1]→na + 1 | M[1]→B[M[1]→nb]→length = |
| M[1]→nb = M[1]→nb + 1 | sqrt ((M[1]→B[M[1]→nb]→vector)**2) |
| M[1]→A[M[1]→na]→a = M[1]→na | M[1]→A[3]→nb = M[1]→A[3]→nb + 1 |
| M[1]→B[M[1]→nb]→b = M[1]→nb | M[1]→A[3]→b[M[1]→A[3]→nb] = |
| M[1]→B[M[1]→nb]→a[1] = M[1]→A[3]→a | M[1]→nb |
| M[1]→B[M[1]→nb]→a[2] = M[1]→na | M[1]→A[M[1]→na]→nb = 1 |
| M[1]→A[M[1]→na]→eventFlag = Null | M[1]→A[M[1]→na]→b = M[1]→nb |
| ○AFTER NEW ATOM EVENT | |
| E[1] | : {NewAtom, 3, 0, 0, 0, {A[6]}, {B[5]}, {Null}, {Null}} |
| M[1] | : {6, 5, 1, 0, {A[6]}, {B[5]}} |
| M[1]→A[3] | : {3, {O}, 3, {2, 4, 5}, Null, {x_{A3}, y_{A3}, z_{A3}}} |
| M[1]→A[6] | : {6, {C}, 1, {5}, Null, {x_{A6}, y_{A6}, z_{A6}}} |
| M[1]→B[5] | : {5, {3, 6}, Null, {x_{B5}, y_{B5}, z_{B5}}, length_B5} |

FIG.63

○BEFORE UNDO OPERATION (AFTER NEW ATOM)
E[1]         : {NewAtom, 3, 0, 0, 0, {Null}, {Null}, {Null}}
E[1]→na'     : 3
M[1]         : {6, 5, 1, 0, {A[6]}, {B[5]}}
M[1]→A[3]    : {3, {O}, 3, {2, 4, 5}, Null, {$x_{A3}$, $y_{A3}$, $z_{A3}$}}
M[1]→A[6]    : {6, {C}, 1, {5}, Null {$x_{A6}$, $y_{A6}$, $z_{A6}$}}
M[1]→B[5]    : {5, {3, 6}, Null, {$x_{B5}$, $y_{B5}$, $z_{B5}$}, length_B5}

○USER INPUT  : D→eventFlag = Undo

○UNDO OPERATION
M[1]→nu = M[1]→nu + 1
E1 = M[1]→ne − M[1]→nu + 1
M[1]→A[E[E1]→na'] =
       M[1]→A[E[E1]→na']→nb − 1
M[1]→na = M[1]→na − 1
M[1]→nb = M[1]→nb − 1

○AFTER UNDO OPERATION
M[1]         : {5, 4, 1, 1, {A[6]}, {B[5]}}
E[1]→A[3]    : {3, {O}, 2, {2, 4}, Null, {$x_{A3}$, $y_{A3}$, $z_{A3}$}}

FIG.64

| ○BEFORE REDO OPERATION (NEW ATOM→AFTER UNDO) | |
|---|---|
| E[1] | : {NewAtom, 3, 0, 0, 0, {Null}, {Null}, {Null}} |
| E[1]→na' | : 3 |
| M[1] | : {5, 4, 1, 1, {A[6]}, {B[5]}} |
| M[1]→A[3] | : {3, {O}, 2, {2, 4}, Null, {$x_{A3}$, $y_{A3}$, $z_{A3}$}} |

| ○USER INPUT | : D→eventFlag = Redo |
|---|---|

○REDO OPERATION
E1 = M[1]→ne − M[1]→nu + 1
M[1]→nu = M[1]→nu − 1
M[1]→A[E[E1]→na']→nb =
　　　　　M[1]→A[E[E1]→na']→nb + 1
M[1]→na = M[1]→na + 1
M[1]→nb = M[1]→nb + 1

| ○AFTER REDO OPERATION | |
|---|---|
| M[1] | : {6, 5, 1, 0, {A[6]}, {B[5]}} |
| M[1]→A[3] | : {3, {O}, 3, {2, 4, 5}, Null, {$x_{A3}$, $y_{A3}$, $z_{A3}$}} |
| M[1]→A[6] | : {6, {O}, 1, {5}, Null, {$x_{A6}$, $y_{A6}$, $z_{A6}$}} |
| M[1]→B[5] | : {5, {3, 6}, Null, {$x_{B5}$, $y_{B5}$, $z_{B5}$}, length_B5} |

FIG.66

| M[1] (BEFORE NEW ATOM) | |
|---|---|
| D | : {Null, {C}, {CH4}, 2} |
| M[1] | : {5, 4, 0, 0, {A[5]}, {B[4]}} |
| M[1]→A[1] | : {1, {C}, 3, {1, 2, 3}, Null,...} |
| M[1]→A[2] | : {2, {O}, 1, {1}, Null,...} |
| M[1]→A[3] | : {3, {O}, 2, {2, 4}, Select,...} |
| M[1]→A[4] | : {4, {H}, 1, {3}, Null,...} |
| M[1]→A[5] | : {5, {H}, 1, {4}, Null,...} |
| M[1]→B[1] | : {1, {1, 2}, Null,...} |
| M[1]→B[2] | : {2, {1, 3}, Null,...} |
| M[1]→B[3] | : {3, {1, 4}, Null,...} |
| M[1]→B[4] | : {4, {3, 5}, Null,...} |

| M[1] (AFTER NEW ATOM) | |
|---|---|
| M[1] | : {6, 5, 1, 0, {A[6]}, {B[5]}} |
| M[1]→A[1] | : {1, {C}, 2, {1, 3}, Null,...} |
| M[1]→A[2] | : {2, {O}, 1, {1}, Null,...} |
| M[1]→A[3] | : {3, {O}, 3, {2, 4, 5}, Null,...} |
| M[1]→A[4] | : {4, {H}, 1, {3}, Null,...} |
| M[1]→A[5] | : {5, {H}, 1, {4}, Null,...} |
| M[1]→A[6] | : {6, {C}, 1, {5}, Null,...} |
| M[1]→B[1] | : {1, {1, 2}, Null,...} |
| M[1]→B[2] | : {2, {1, 3}, Null,...} |
| M[1]→B[3] | : {3, {1, 4}, Null,...} |
| M[1]→B[4] | : {4, {3, 5}, Null,...} |
| M[1]→B[5] | : {5, {3, 6}, Null,...} |

FIG.73

| | |
|---|---|
| CONVENTIONAL EXAMPLE: | E={eventFlag, {M[ne]}} <br> M={na, nb, ne, {A[na]}, {B[nb]}} |
| EMBODIMENT: | D={eventFlag, {Atom}, {mSelect}, a} <br> E={eventFlag, na', nb', na, nb, {A[na']}, {B[nb']}, {A'}, {B'}} <br> M={na, nb, ne, nu, {A[na]}, {B[nb]}} <br> A={a, {Atom}, nb, {b[nb]}, eventFlag, {coordinate}} <br> B={b, {a[2]}, eventFlag, {vector}, length} |

FIG.74

| EXAMPLE OF CONVENTIONAL EXAMPLE (a & b ARE CONSTANTS, i=0~m) | EXAMPLE OF EMBODIMENT |
|---|---|
| $M_i = a + (n+i)(56+x) + (nb+i)(4+y)$<br>$E_i = b + M_i$<br>$Total = \Sigma i (E_i)$ | $D = 16, \quad E = 20m$<br>$M = 16 + A + B$<br>$A = 40 + (24+x)(n+m)$<br>$B = 20 + (24+y)(nb+m)$<br>$Total = D + E + M$ |
| n=1000,nb=1000,m=1000→90090000<br>(a=0,b=0,x=0,y=0 : NO GUI MEMORY) | n=1000,nb=1000,m=1000→116092<br>(x=0,y=0 : NO GUI MEMORY)<br>1/776 THE SIZE OF CONVENTIONAL EXAMPLE |

*INITIAL ATOM NO.: n, INITIAL BOND AXIS NO.: nb
GUI MEMORY FOR ATOMIC SPHERE: x (Bytes), GUI MEMORY FOR BOND AXIS: y (Bytes)

Moved to response.

It is to be understood that both the foregoing general description and the following detailed description are exemplary and explanatory and are not restrictive of the invention, as claimed.

BRIEF DESCRIPTION OF THE DRAWINGS

FIG. 1 is a diagram for explaining a data structure;

FIG. 2 is a diagram for explaining how the data structure is set by taking formic acid (HCOOH) as an example;

FIG. 6 is a diagram illustrating a state of a molecular structure before a molecular structure modifying operation;

FIG. 10 is a diagram illustrating a relationship between an event operation and an event flag "eventFlag";

FIG. 11 is a diagram illustrating a relationship between an item on which an event operation may be performed and a delete bit "Delete";

FIG. 12 is a diagram illustrating a relationship of an Undo operation, a Redo operation and an event number;

FIG. 13 is a flow chart for explaining constructing of an initial data structure;

FIG. 14 is a diagram illustrating an example of a data change by a delete event for the formic acid (HCOOH);

FIG. 15 is a diagram for explaining the constructing of an Undo operation related to the delete event illustrated in FIG. 14;

FIG. 16 is a diagram for explaining the constructing of a Redo operation related to the Undo operation illustrated in FIG. 15;

FIG. 19 is a diagram illustrating an example of a structural change by the delete event for the formic acid (HCOOH);

FIG. 26 is a diagram illustrating an example of a data change by a substitute event for the formic acid (HCOOH);

FIG. 27 is a diagram for explaining the construction of an Undo operation related to the substitute event illustrated in FIG. 26;

FIG. 28 is a diagram for explaining the construction of a Redo operation related to the Undo operation illustrated in FIG. 27;

FIG. 29 is a flow chart for explaining a process of the substitute event;

FIG. 38 is a diagram illustrating an example of a data changed by an add event for the formic acid (HCOOH);

FIG. 39 is a diagram for explaining the construction of an Undo operation related to the add event illustrated in FIG. 38;

FIG. 40 is a diagram for explaining the construction of a Redo operation related to the Undo operation illustrated in FIG. 39;

FIG. 50 is a diagram illustrating an example of a data change by a bond axis adding event (or new bond event) for the formic acid (HCOOH);

FIG. 51 is a diagram for explaining the construction of an Undo operation related to the new bond event illustrated in FIG. 50;

FIG. 52 is a diagram for explaining the construction of a Redo operation related to the Undo operation illustrated in FIG. 51;

FIG. 62 is a diagram illustrating an example of a data change by a new atom event (or new atom adding event) for the formic acid (HCOOH);

FIG. 63 is a diagram for explaining the construction of an Undo operation related to the new atom event illustrated in FIG. 62;

FIG. 64 is a diagram for explaining the construction of a Redo operation related to the Undo operation illustrated in FIG. 63;

FIG. 66 is a diagram illustrating an example of a structural change by the new atom event for the formic acid (HCOOH);

FIG. 73 is a diagram comparing data structures of the embodiment and the conventional example; and FIG. 74 is a diagram comparing effects of the embodiment and the conventional example.

DESCRIPTION OF EMBODIMENTS

Figure 3:
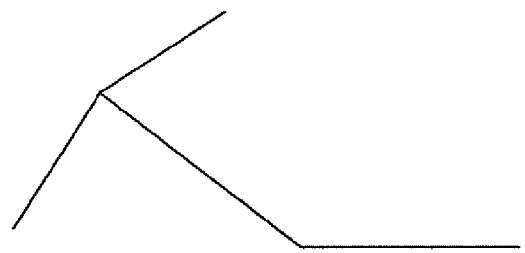
FIG. 3 is a diagram for explaining a display of a half vector format.

Preferred embodiments of the present invention will be described with reference to the accompanying drawings.

A description will now be given of the molecular design method and computer-readable storage medium in each embodiment according to the present invention.

In the disclosed molecular design method, data of a data structure defined as illustrated in FIG. 1 is used when performing a molecular structure modifying operation. More particularly, the data structure includes atomic data structures A and A' related to an atom, bond axis data structures B and B' related to a bond axis, a molecular data structure M related to a molecule, an auxiliary data structure D, and an event data structure E. In the data structure illustrated in FIG. 1, the atomic data structures A and A' and the bond axis data structures B and B' respectively include data having a 1:1 correspondence with respect to all atoms and bond axes, and an event flag, and an identification flag. The event data structure E includes event information data, and the auxiliary data structure D assists an event operation that includes the molecular structure modifying operation. The molecular data structure M includes an Undo event operation number. Each of the data structures A, A', B, B', M, D and E includes an event flag. In FIG. 1, constituent elements (or items) of each of the data structures A, A', B, B', M, D and E have numbers 1, 2, 3, . . . assigned thereto, and data in brackets denote data that are not essential.

In the atomic data structures A and A', an identification number "a" is made up of an atomic sequence number in an internal coordinate, and an atomic number "Atom" is made up of a chemical symbol. In addition, a bond axis number "nb" is made up of a numerical value which varies when an arbitrary new molecular structure is added to the original molecule. An initial value of the bond axis number "nb" indicates a bond number that is estimated from an input structure as forming an atomic pair based on the van der Waals radius. An identification number "b" of the bond axis is made up of data (or set data) of a set of identification numbers of each of the bond axes included in the bond axis number "nb". The event flag "eventFlag" indicates the kind of the present (or current) event operation with respect to an event operation of a molecular structure constructing GUI, such as a delete operation, an add operation, a substitute operation, a bond axis add operation (or new bond operation), and an atom adding operation (or new atom operation). The identification flag is used to check whether a ring structure is obtained, in order to prevent an unwanted structure from being obtained, and this identification flag may be omitted. xyz coordinates "coordinate" indicate Cartesian coordinates, and include data indicate a position (or location) of each atom existing in a three-dimensional space. For example, the atomic data structure A may be represented by A={a, {Atom}, nb, {b[nb]}, eventFlag, {coordinate}}.

In the bond axis data structures B and B', the identification number "b" is made up of a number necessary to make a 1:1 correspondence for all of the bond axes. The bond type includes data for identifying the type of bond axis, such as a single bond and a double bond. When constructing an arbitrary molecular structure, the bond type is not necessarily essential. The identification numbers "a" of the terminal atoms are made up of data (or set data) of a set of identification numbers of the atoms existing at both ends of the bond axis, and the data number (or number of data) thereof is two. The event flag "eventFlag" and the identification flag are the same as the event flag "eventFlag" and the identification flag of the atomic data structures A and A'. Vector information "vector" indicates a 1:1 correspondence of the bond axis and a three-dimensional vector. When the vector information "vector" is represented by a unit vector, a bond axis length "length" which indicates the length of the bond axis also needs to be included in the bond axis data structures B and B'. For example, the bond axis data structure B may be represented by B={b, {a[2]}, eventFlag, {vector}, length}.

The molecular data structure M includes both the atomic data structures A and A' and the bond axis data structures B and B' which hold mutual data thereof. The molecular data structure M includes the atomic data number "na", the bond axis data number "nb", the event information data and the like, in order to also cope with the delete operation and the add operation. The molecular data structure M further includes a total event operation number "ne" and an Undo event operation number "nu", in order to efficiently execute the Undo operation and the Redo operation. The molecular data structure M also includes an atomic data "A" within the molecule, and a bond axis data "B" within the molecule. For example, the molecular data structure M may be represented by M={na, nb, ne, nu, {A[na]}, {B[nb]}}.

The auxiliary data structure D includes an event flag "eventFlag" which is similar to that of the atomic data structures A and A', an atomic number "Atom", and molecule setting information "mSelect" corresponding to atomic setting information after substitution by a substitute operation or an added partial structure of an add operation. The auxiliary data structure D also includes identification information (or identification number) "a" indicating the identification information of the added atom in order to identify the bond position of the add operation with respect to the original molecular structure. For example, the auxiliary data structure D is represented by D={eventFlag, {Atom}, {mSelect}, a}.

The event data structure E includes an event flag "eventFlag" which is similar to that of the atomic data structures A and A', a selected atom number "na'", a selected bond axis number "nb'", an atomic data "A'" after the process, and a bond axis data "B'" after the process. The event data structure E further includes an added atom data number "na" indicating the number of added atom data, a bond axis data number "nb" indicating the number of added bond axis data, an atomic data "A" indicating the atomic data before the process, and a bond axis data "B" indicating the bond axis data before the process. The selected atom number "na'" and the selected bond axis number "nb'" indicate the atom and the position of the bond axis that are specified in order to determine the operation position when making an event operation. The added atom data number "na" and the added bond axis data number "nb" indicate the atom number and the bond axis number within the partial structure related to the add operation. The atomic data "A" before the process and the bond axis data "B" before the process indicate the atomic data structure and the bond axis data structure before the event operation such as the substitution. The atomic data "A'" after the process and the bond axis data "B'" after the process indicate the atomic data structure and the bond axis data structure after the event operation such as the substitution. For example, the event data structure E may be represented by E={eventFlag, na', nb', na, nb, {A[na']}, {B[nb']}, {A'}, {B'}}.

A description will be given of how the data structure illustrated in FIG. 1 is set when the data of the molecular structure is given, by taking formic acid (HCOOH) as an example, in conjunction with FIG. 2. FIG. 2 is a diagram for explaining how the data structure is set by taking formic acid (HCOOH) as an example. In FIG. 2, "A[ ]" denotes the atomic data structure "A", "B[ ]" denotes the bond axis data structure "B", "M[ ]" denotes the molecular data structure "M", "D[ ]" denotes the auxiliary data structure "D", and "E[ ]" denotes the event data structure "E". Hence, "M[1]" denotes the molecular data structure of formic acid, M[1]→A denotes the atomic structure of the formic acid, and "B" denotes the bond axis data structure of the formic acid. In addition, "M[2]" denotes the methane molecular structure set to D→mSelect={CH4}, and M[2]→A and M[2]→B respectively denote the bond axis of the atom within the methane molecule.

Figure 4:
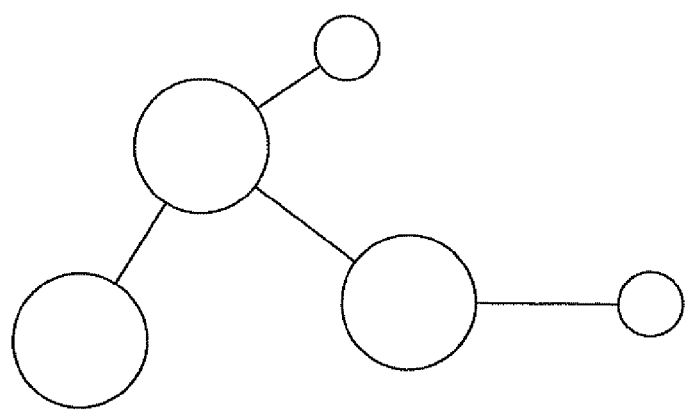
FIG. 4 is a diagram for explaining a display of a ball-and-stick format.
Figure 5:
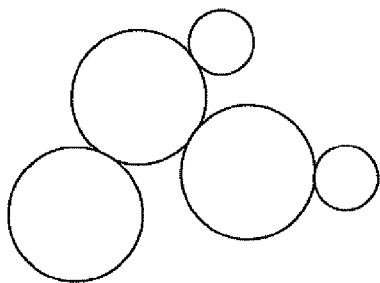
FIG. 5 is a diagram for explaining a display of a space fill format.

When making a molecular structure modifying operation, such as delete, substitute, add and new operations, a main window for work is displayed on a display screen, for example, and a three-dimensional molecular structure is displayed in this main window with the half vector format illustrated in FIG. 3 or, in the ball-and-stick format illustrated in FIG. 4 or, in the space filing format illustrated in FIG. 5. FIG. 3 is a diagram for explaining the display of the half vector format, FIG. 4 is a diagram for explaining the display of the ball-and-stick format, and FIG. 5 is a diagram for explaining the display of the space fill format. A partial structure which is the modifying target is determined by specifying the atom and the bond axis on the main window by making a clicking or drag-and-drop operation by a pointing device, or by making an input operation such as a keyboard operation from an input part.

Figure 7:
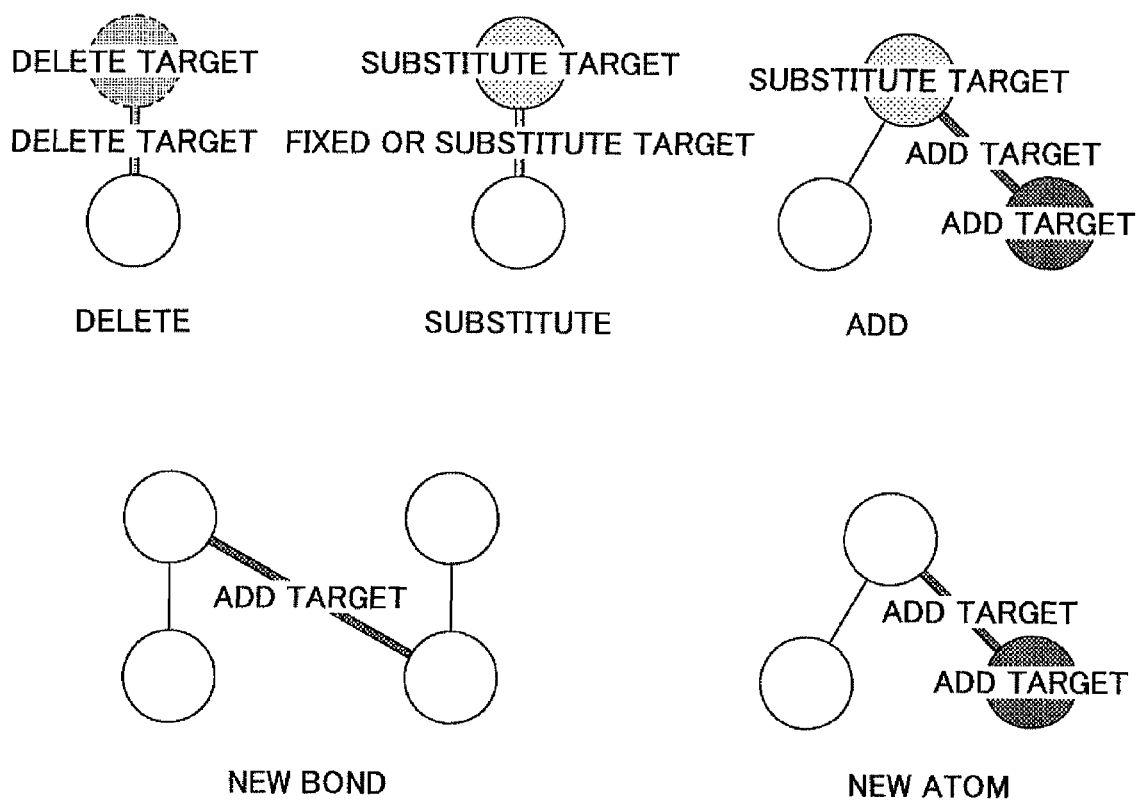
FIG. 7 is a diagram illustrating a state of the molecular structure after the molecular structure modifying operation.

In a case where the molecular structure modifying operation is the delete operation which deletes a partial structure from the molecular structure, the partial structure which is the delete target as illustrated in FIG. 6 is determined, and a new molecular structure which has been deleted of the partial structure as illustrated in FIG. 7 is displayed on the main window, by specifying the bond axis in the half vector format or, the atom in the ball-and-stick format and also the bond axis if necessary or, the atom in the space fill format. FIG. 6 is a diagram illustrating a state of the molecular structure before the molecular structure modifying operation, and FIG. 7 is a diagram illustrating the state of the molecular structure after the molecular structure modifying operation. By using the data structures described above, the Undo operation which returns the molecular structure after the delete operation back to the original molecular structure, and the Redo operation which performs the delete operation on the molecular structure again after the Undo operation, are continuously executed as will be described later in conjunction with the embodiment while suppressing the amount of storage capacity that is used for the operation.

In a case where the molecular structure modifying operation is the substitute operation which substitutes a partial structure of the molecular structure, the partial structure which is the substitute target as illustrated in FIG. 6 is determined, and a new molecular structure which has been substituted of the partial structure as illustrated in FIG. 7 is displayed on the main window, by specifying the atom in the ball-and-stick format or, the atom in the space fill format. By using the data structures described above, the Undo operation which returns the molecular structure after the substitute operation back to the original molecular structure, and the Redo operation which performs the substitute operation on the molecular structure again after the Undo operation, are continuously executed as will be described later in conjunction with the embodiment while suppressing the amount of storage capacity that is used for the operation.

In a case where the molecular structure modifying operation is the add operation which adds a partial structure to a position of a certain atom in place of the certain atom in the molecular structure, the position where the target partial structure is to be added as illustrated in FIG. 6 is determined, and a new molecular structure which has been added with the partial structure in place of the certain atom as illustrated in FIG. 7 is displayed on the main window, by specifying the bond axis in the half vector format or, the atom in the ball-and-stick format or, the atom in the space fill format. By using the data structures described above, the Undo operation which returns the molecular structure after the add operation back to the original molecular structure, and the Redo operation which performs the add operation on the molecular structure again after the Undo operation, are continuously executed as will be described later in conjunction with the embodiment while suppressing the amount of storage capacity that is used for the operation.

In this case, with respect to bond axes B1 and B2 of a specified atom A1 in the three-dimensional molecular structure that is displayed in the ball-and-stick format or the space fill format, the molecular structure modifying operation may be restricted if it is possible to move from the bond axis B1 to a terminal atom A2 other than the specified atom A1 and similar procedures can be continued to move to the bond axis B2 by tracing other atoms.

In a case where the molecular structure modifying operation is the new bond operation which newly adds a bond axis to the molecular structure, two target atoms to which the bond axis is to be added as illustrated in FIG. 6 are determined, and a new molecular structure which has been added with the bond axis to the original molecular structure as illustrated in FIG. 7 is displayed on the main window, by specifying the two target atoms in the ball-and-stick format. By using the data structures described above, the Undo operation which returns the molecular structure after the new bond operation back to the original molecular structure, and the Redo operation which performs the new bond operation on the molecular structure again after the Undo operation, are continuously executed as will be described later in conjunction with the embodiment while suppressing the amount of storage capacity that is used for the operation.

In a case where the molecular structure modifying operation is the new atom operation which newly adds a new atom to the molecular structure, the position of the target atom to which the new atom is to be added as illustrated in FIG. 6 is determined, and a new molecular structure which has been added with the atom to the original molecular structure as illustrated in FIG. 7 is displayed on the main window, by specifying the target atom in the ball-and-stick format or the space fill format. By using the data structures described above, the Undo operation which returns the molecular structure after the new atom operation back to the original molecular structure, and the Redo operation which performs the new atom operation on the molecular structure again after the Undo operation, are continuously executed as will be described later in conjunction with the embodiment while suppressing the amount of storage capacity that is used for the operation.

Accordingly, an arbitrary molecular structure modifying operation can be executed with ease while suppressing the amount of storage capacity (or memory capacity) required for the operation.

EMBODIMENTS

Figure 8:
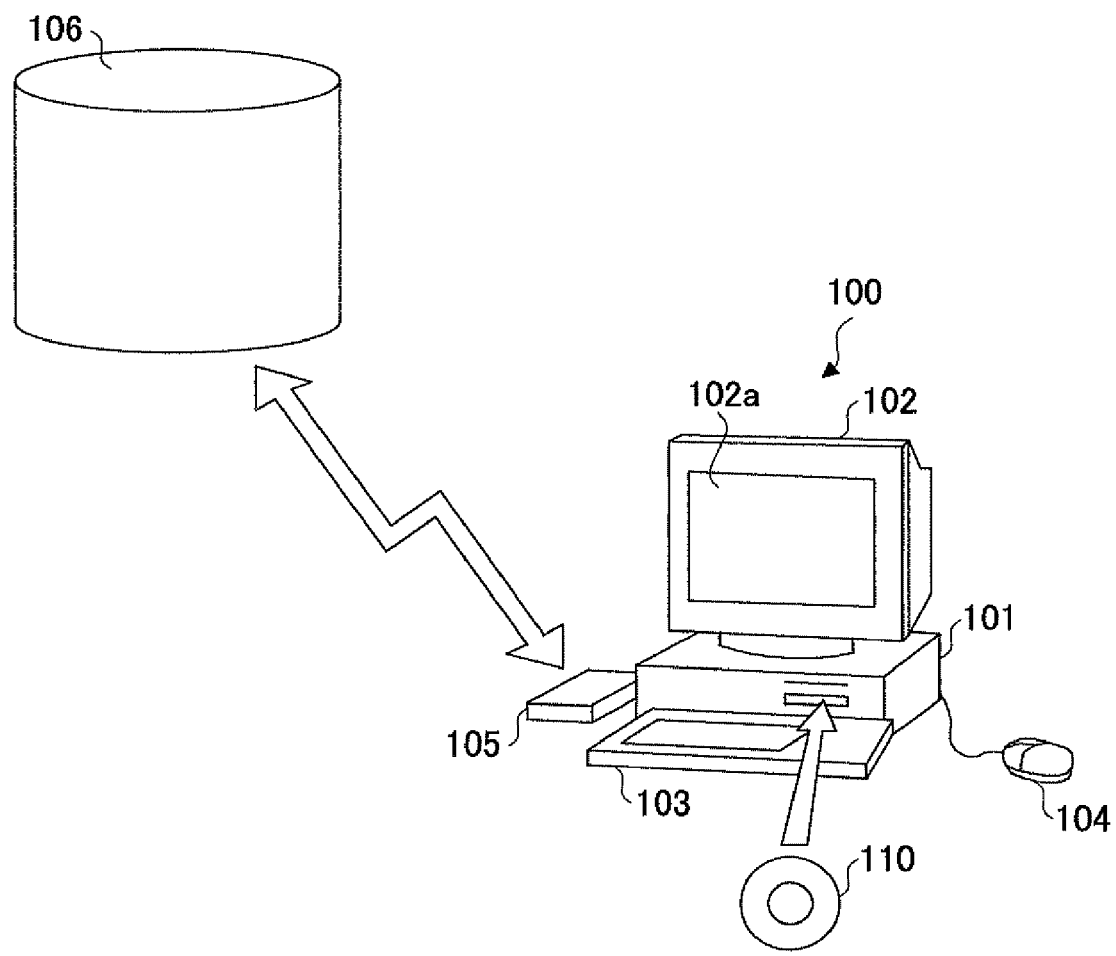
FIG. 8 is a perspective view illustrating a computer system to which an embodiment of the present invention may be applied.

In one embodiment of the present invention, the molecular design method is performed by executing a program on a computer. This embodiment of the present invention may be applied to a computer system which forms a molecular design support apparatus. FIG. 8 is a perspective view illustrating the computer system to which an embodiment of the present invention may be applied.

A computer system 100 illustrated in FIG. 8 includes a main body 101, a display 102, a keyboard 103, a mouse 104, and a modem 105. The main body 101 includes a Central Processing Unit (CPU), a disk drive and the like. The display 02 displays images of molecules and the like that are formed by a molecule forming simulation on a display screen 102a in response to an instruction from the main body 101. The keyboard 103 is used to input various information to the computer system 100. The mouse 104 is used to specify an arbitrary position on the display screen 102a of the display 102. The modem 105 makes an access to an external database or the like and downloads programs and the like that are stored in another computer system.

A program (or molecular design support software) which, when executed by a computer such as the CPU, causes the computer system 100 to perform at least a molecule design support function, is stored in a portable recording medium such as a disk 110 or, is downloaded from a recording medium 106 of another computer system using a communication apparatus such as the modem 105. This program is input to the computer system 100 and compiled therein. In other words, the program causes the computer system (that is, a CPU 201 which will be described later) to operate as the molecule design support apparatus (or a simulation system) having the molecule design support function. The program may be stored in a computer-readable storage medium such as the disk 110. The computer-readable storage medium is not limited to a portable recording medium such as the disk 110, an Integrated Circuit (IC) card memory, magnetic recording media such as a floppy disk (registered trademark), magneto-optical recording media, and optical recording media such as a CD-ROM. In other words, the computer-readable storage medium includes any type of recording media that are accessible by a computer which is connected via a communication apparatus such as the modem 105, a Local Area Network (LAN) and the like.

Figure 9:
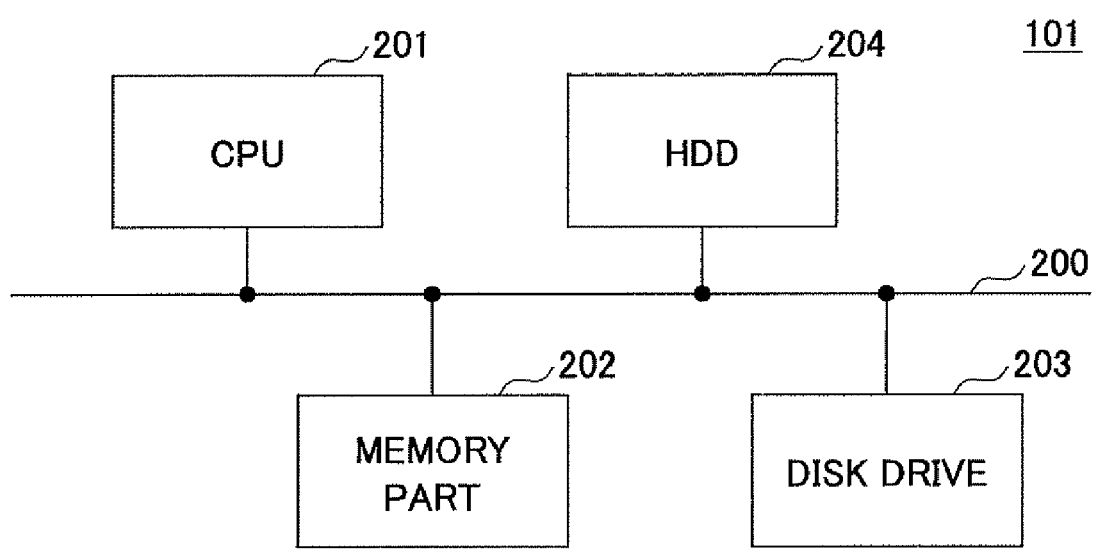
FIG. 9 is a block diagram for explaining a structure of a part within a main body of the computer system.

FIG. 9 is a block diagram for explaining a structure of a part within the main body 101 of the computer system 100 illustrated in FIG. 8. The main body 101 includes a CPU 201, a memory part 202, a disk drive 203 for the disk 110, and a Hard Disk Drive (HDD) 204 which are connected via a bus 200 as illustrated in FIG. 9. The memory part 202 includes a Random Access Memory (RAM), a Read Only Memory (ROM) and the like. In this embodiment, the display 102, the keyboard 103 and the mouse 104 are also connected to the CPU 201 via the bus 200, however, the display 102, the keyboard 103 and the mouse 104 may be connected directly to the CPU 201. In addition, the display 102 may be connected to the CPU 201 via a known graphic interface (not illustrated) which processes input and output image data.

In the computer system 100, the keyboard 103 and the mouse 104 form an input part of the molecule design support apparatus. The display 102 displays the three-dimensional molecular structure in the half vector format or the ball-and-stick format or the space fill format on the display screen 102a. The CPU 201 executes a determining step or procedure, a modifying step or procedure, and a display step or procedure. Based on a bond axis specified from the input part in a molecular structure, the determining step or procedure determines a side (or end) that is a target of a coordinate modification with respect to at least the specified bond axis. The modifying step or procedure performs a modification on the molecular structure, including a rotation about the specified bond axis and expansion or contraction of the specified bond axis, based on an instruction from the input part. The display step or procedure displays on the display screen 102a of the display 102 the molecular structure which has been modified based on the determination made by the determining step or procedure or the modification made by the modifying step or procedure.

The structure of the computer system 100 is of course not limited to that illustrated in FIGS. 8 and 9, and it is possible to use various known structures instead.

In this embodiment, when performing the molecular structure modifying operation such as to delete, substitute and add the partial structure of the molecular structure, the main window for work is displayed on the display screen 102a of the display 102, and the three-dimensional molecular structure is displayed in the half vector format illustrated in FIG. 3 or, in the ball-and-stick format illustrated in FIG. 4 or, in the space fill format illustrated in FIG. 5, for example. The partial structure that is the modifying target is determined by specifying the atom or the bond axis on the main window by making a clicking or drag-and-drop operation by the pointing device, or by making an input operation from the input part such as the keyboard 103. In addition, it is possible to perform in succession to the molecular structure modifying operation the Undo operation which returns the molecular structure after the molecular structure modifying operation back to the original molecular structure, and the Redo operation which performs the molecular structure modifying operation on the molecular structure again after the Undo operation.

The Undo operation, the Redo operation and the actual event operation have the relationship illustrated in FIGS. 10 through 12 with respect to the data structures illustrated in FIG. 1. FIG. 10 is a diagram illustrating the relationship between the event operation and the event flag "eventFlag".

FIG. 11 is a diagram illustrating the relationship between an item on which the event operation may be performed and a delete bit "Delete". FIG. 12 is a diagram illustrating the relationship of the Undo operation, the Redo operation and the event number.

FIG. 13 is a flow chart for explaining constructing of an initial data structure. The process illustrated in FIG. 13 is executed by the CPU 201.

In FIG. 13, a step S1 declares an atomic data composition having the atomic data structure "A" illustrated in FIG. 1, a bond axis data composition having the bond axis data structure "B" illustrated in FIG. 1, and an auxiliary data composition having the auxiliary data structure "D" illustrated in FIG. 1. A step S2 declares a molecular data composition having the molecular data structure "M" illustrated in FIG. 1 and an event data composition having the event data structure "E" illustrated in FIG. 1, as compositions including the atomic data composition and the bond axis data composition. A step S3 sets initial values of the event flag "eventFlag", the event number and the like.

A step S4 reads the Cartesian (xyz coordinates) or Z-matrix coordinate data from a storage part, and stores the atomic number in the atomic data number "na" of the molecular data structure M. The storage part may be formed by any of the memory part 202, the disk drive 203 and the HDD 204 within the computer system 100 or, may be formed by the recording medium 105 or the like external to the computer system 100. A step S5 transforms the read coordinate data into the Cartesian coordinates if the read coordinate data is the Z-matrix coordinate data, and stores the transformed data into the xyz coordinates "coordinate" and the atomic number "Atom" of the atomic data structure "A", and also sets the identification number "a" in the storing sequence. A step S6 computes all interatomic bond distances using the atomic coordinates.

A step S7 forms a bond axis between the atoms that are located at a distance less than or equal to an arbitrarily set threshold value. A step S8 sets the identification number "b" of the bond axis data structure "B" in the forming sequence, and stores the bond axis number in the bond axis data number "nb" of the molecular data structure "M". A step S9 stores the vector of the bond axis in the vector "vector" of the bond axis data structure "B". A step S10 stores the identification numbers of the two atoms related to the bond axis in the identification numbers "a[1]" and "a[2]" of the terminal atoms of the bond axis data structure "B". A step S11 extracts the identification number of the bond axis related to each atom, stores the identification number "b" and the bond axis number (total number) "nb" in the atomic data structure "A", and the process ends. Hence, with respect to the given molecular data structure, the initial data structure made up of the atomic data structure "A", the bond axis data structure "B", the molecular data structure "M", the auxiliary data structure "D" and the event data structure "E" illustrated in FIG. 1 is constructed and stored in the storage part.

Next, a description will be given of the relationship among each event operation, the Undo operation and the Redo operation.

1. Relationship Among the Event Operation, Undo Operation and Redo Operation:

With respect to the data structure illustrated in FIG. 1 that is constructed by the process illustrated in FIG. 13, the user selects a bond axis item or an atom item by clicking the mouse 104, for example, in order to set a select bit "Select" in the event flag "eventFlag" of the selected bond axis item or atom item. This process is represented by M→B→eventFlag=Select or M→A→eventFlag=Select. When the delete bit "Delete" is set in the event flag "event-Flag" of the auxiliary data structure "D", a delete event is executed as illustrated in FIG. 14 in the case of the example illustrated in FIG. 2. FIG. 14 is a diagram illustrating an example of a data change by the delete event for the formic acid (HCOOH). FIG. 14 illustrates a state before the delete event, a user input, a delete event operation, and a state after the delete event. The event flag "eventFlag" of the auxiliary data structure "D" may be set in advance.

First, the delete bit "Delete" is set in the item for which the select bit "Select" is set. In addition, the delete bit "Delete" is also set in the bond axis data corresponding to the bond axis information included in the atomic data for which the select bit "Select" is set. Next, a present total event operation number is updated to M→ne=M→ne−M→nu+1, and the Undo event operation number is initialized to M→nu=0. When the total event operation number is updated, the subsequent event data is initialized to E[n>=M→ne]=Null, and the data for the delete event is substituted into the present event by E[M→ne]→eventFlag=Delete, . . . , etc. In the case of the delete event, the information of the atom item and the bond axis information for which the delete bit "Delete" is set are registered in the bond axis data before the processing of the event data and the atomic data before the processing of the event data, as well as the numbers thereof. In this state, the delete bit "Delete" and the select bit "Select" are reset with respect to the bond axis data before the processing of the event data and the atomic data before the processing of the event data. After the substitution to the event data ends, the atom number information and the bond axis information of the molecular data are updated, and the bond axis information included in the atomic data of the atom item is updated if necessary. Finally, the item information for which the delete bit "Delete" is set is registered in the bond axis data after the processing of the event data and the atomic data after the processing of the event data.

The delete event operation is completed by redisplaying the molecular structure so as to exclude the item for which the delete bit "Delete" is set from the display contents on the main window, after the data updating described above.

The Undo operation related to the delete event illustrated in FIG. 14 is constructed as illustrated in FIG. 15. FIG. 15 is a diagram for explaining the constructing of the Undo operation related to the delete event illustrated in FIG. 14. In other words, when an Undo bit is set in the event flag "eventFlag" of the auxiliary data structure "D", the Undo event operation number "nu" is first updated to M→nu=M→nu+1. The corresponding event number is set by the total event operation number and the Undo event operation number according to n=m→ne−M→nu+1, and the data before the processing of the corresponding event data is substituted into the present molecular data. The Undo operation is completed by finally redisplaying the molecular structure on the main window.

The Redo operation related to the Undo operation illustrated in FIG. 15 is constructed as illustrated in FIG. 16. FIG. 16 is a diagram for explaining the constructing of the Redo operation related to the Undo operation illustrated in FIG. 15. In other words, when a Redo bit is set in the event flag "eventFlag" of the auxiliary data structure "D", the corresponding event number is first set by the total event operation number and the Undo event operation number according to n=M→ne−M→nu+1. Then, the Undo event operation number is updated to M→nu=M→nu−1, and the data after the processing of the corresponding event data is substituted into the present molecular data. The Redo operation is completed by finally redisplaying the molecular structure on the main window.

Figure 17:
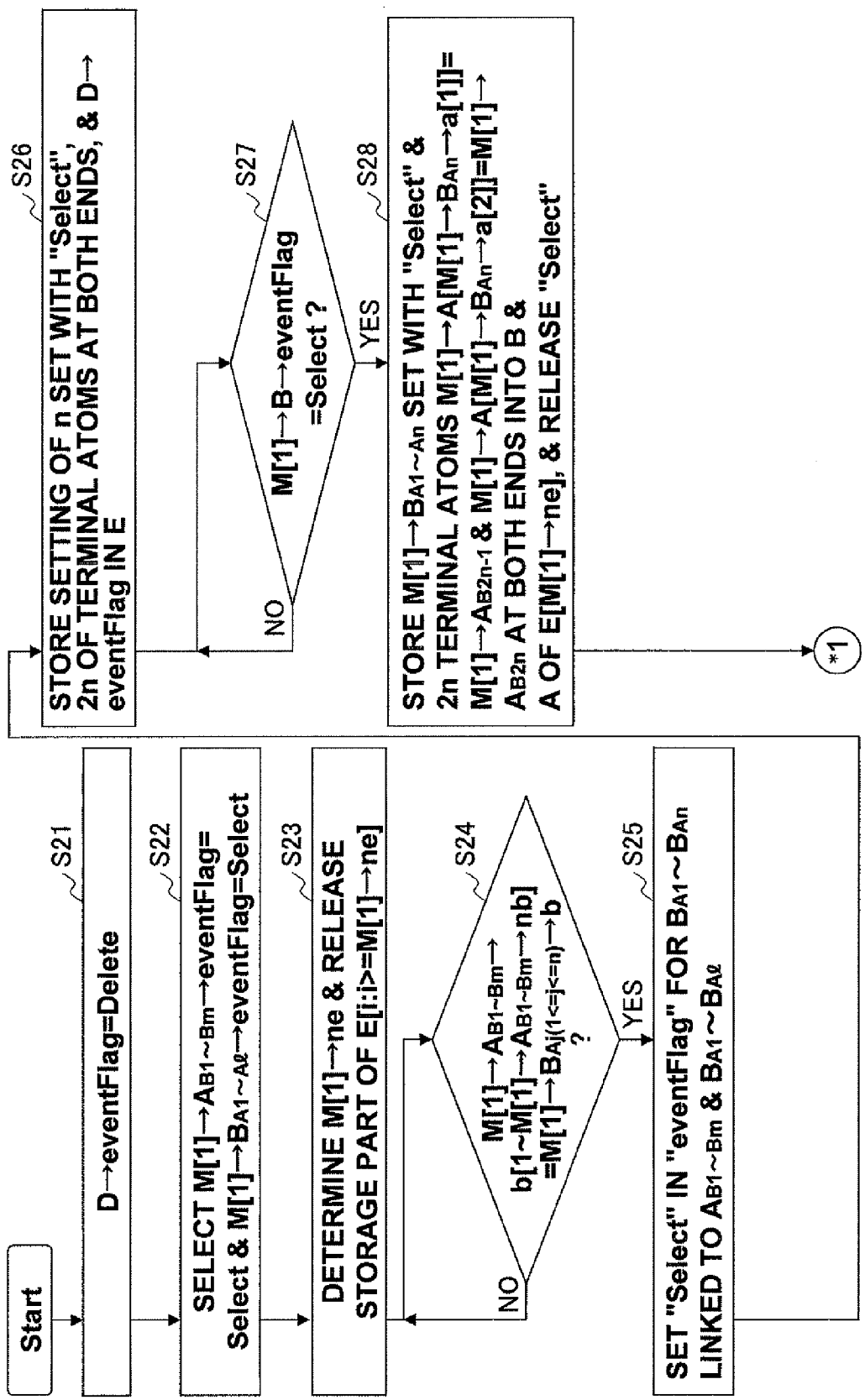
FIG. 17 is a flow chart for explaining a process of the delete event.
Figure 18:
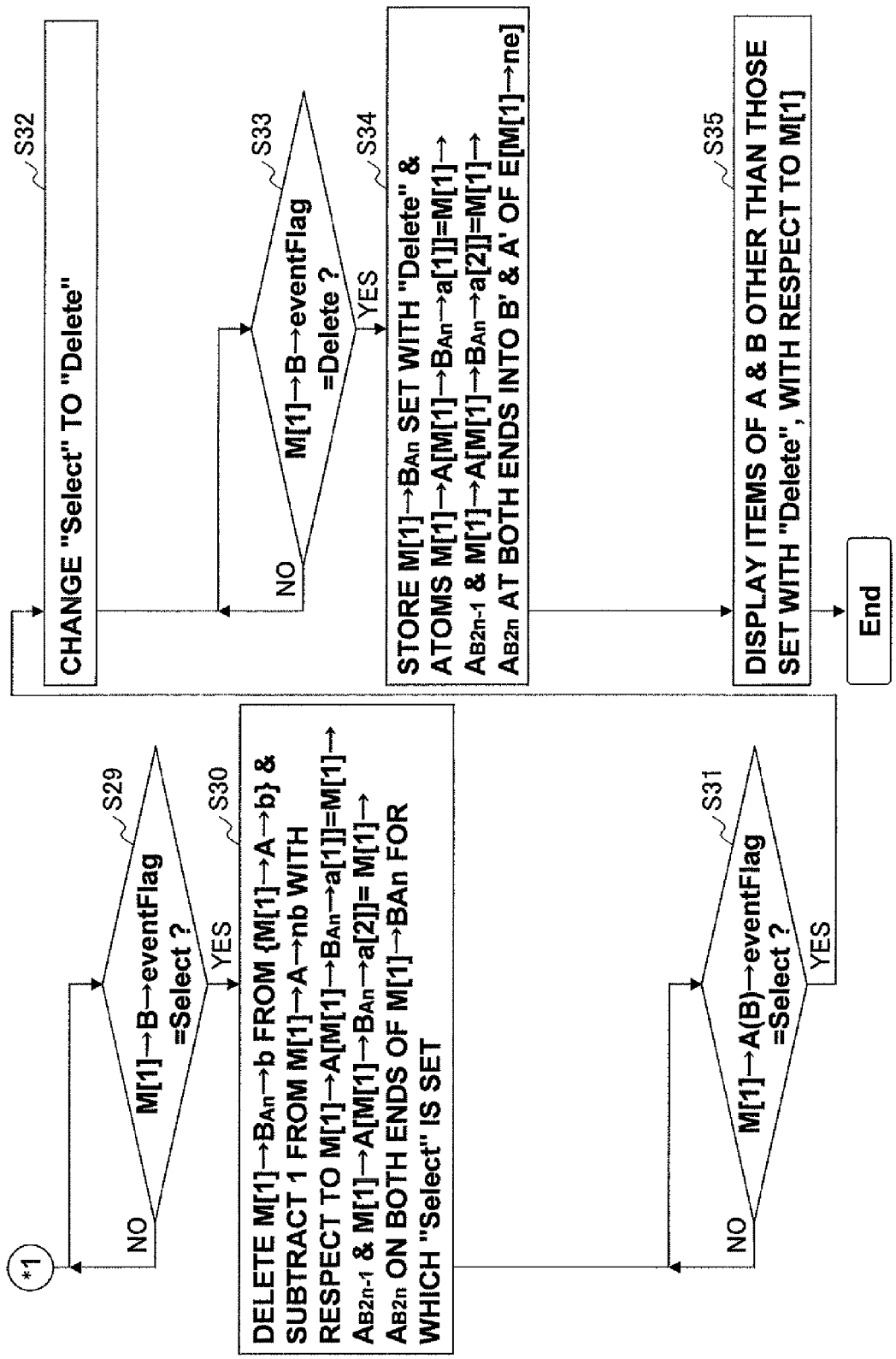
FIG. 18 is a flow chart for explaining the process of the delete event.

FIGS. 17 and 18 are flow charts for explaining the process of the delete event.

First, in FIG. 17, a step S21 sets D→eventFlag=Delete, that is, sets the delete bit "Delete" in the event flag "eventFlag" of the auxiliary data structure "D", based on a setting made by the user from the input part. A step S22 selects M[1]→$A_{B1\sim Bm}$→eventFlag=Select and M[1]→$B_{A1\sim Al}$→eventFlag=Select, that is, selects m+1 corresponding items to m atoms $A_{B1}$~$A_{Bm}$ and l bond axes $B_{A1}$~$B_{Al}$ of the molecular data M[1], based on a selection made by the user from the input part. In this example, the atom item A[3] is selected according to M[1]→A[3]→eventFlag=Select. Next, a step S23 determines M[1]→ne according to M[1]→ne=M[1]→ne−M[1]→nu+1, M[1]→nu=0, and E[n]=Null (M[1]→ne<=n<=MaxEvent), and releases the storage part of E[i:i>=M[1]→ne]. In other words, the total event operation number ne of M[1] is determined, and the storage part is released with respect to the M[1]→(ne)th and subsequent event data. A step S24 decides whether M[1]→$A_{B1\sim Bm}$→b [1~M[1]→$A_{B1\sim Bm}$→nb]=M[1]→$B_{Aj(1<=j<=n)}$→b, and the process advances to a step S25 if the decision result is YES. The step S25 sets the select bit "Select" in the event flag "eventFlag" for a total of n bonding axes $B_{A1}$~$B_{An}$, made up of all bond axes linked to the atoms $A_{B1\sim Bm}$ and the bond axes $B_{A1}$~$B_{Al}$ according to M[1]→$B_{A1}$→eventFlag=Select, . . . , M[1]→$B_{An}$→eventFlag=Select. A step S26 stores setting of the bond axis number n set with the select bit "Select", the number 2n of terminal atoms at both ends, and D→eventFlag in the event data, according to E[M[1]→ne]→eventFlag=D→eventFlag, E[M[1]→ne]→na'=2n, and E[M[1]→ne]→nb'=n. A step S27 decides whether M[1]→B→eventFlag=Select, and the process advances to a step S28 if the decision result is YES.

The step S28 stores n bond axes M[1]→$B_{A1\sim An}$ set with the select bit "Select" and 2n terminal atoms M[1]→A[M[1]→$B_{An}$→a[1]]=M[1]→$A_{B2n-1}$ and M[1]→A[M[1]→$B_{An}$→a[2]]=M[1]→$A_{B2n}$ at both ends into B and A of E[M[1]→ne], according to E[M[1]→ne]→A[1]=M[1]→$A_{B1}$, . . . , E[M[1]→ne]→A[2n]=M[1]→$A_{B2n}$, E[M[1]→ne]→B[1]=M[1]→$B_{A1}$, . . . , E[M[1]→ne]→B[n]=M[1]→$B_{An}$, E[M[1]→ne]→A[1]→eventFlag=Null, E[M[1]→ne]→B[1]→eventFlag=Null, . . . , E[M[1]→ne]→B[n]→eventFlag=Null, and releases the select bit "Select". After the step S28, the process advances to a step S29 illustrated in FIG. 18.

Accordingly, in this example, with respect to the bond axis information 2, 4 included in M[1]→A[3]b[ ], the corresponding bond axes B[2] and B[4] are selected according to M[1]→B[2]→eventFlag=Select and M[1]→B[4]→eventFlag=Select. In addition, the number of atoms set with the select bit "Select" is two from B[2] and B[4], and the number of terminal atoms of B[2] and B[4] on both ends is four, namely, 1, 3, 3 and 5. Hence, the data necessary for the event data is substituted into the event data structure E, according to E[M[1]→ne]→nb'=2, E[M[1]→ne]→na'=2, and E[M[1]→ne]→eventFlag=D→eventFlag=Delete. Furthermore, the data is substituted into the atomic data before the processing and included in the event data, according to E[M[1]→ne]→AM[1]=M[1]→AM[1], . . . , E[M[1]→ne]→AM[4]=M[1]→AM[5], and the data is substituted into the bond axis data before the processing and included in the event data, according to E[M[1]→ne]BM[1]=M[1]→BM[2] and E[M[1]→ne]→BM[2]=M[1]→BM[4]. The event flag "eventFlag" is set to "Null" with respect to the atomic data and the bond axis data of E[M M[1]→ne].

After substituting the data into the event data, the delete operation actually deletes from the molecular data M[1] as illustrated in FIG. 18. The step S29 decides whether M[1]→B→eventFlag=Select, and the process advances to a step S30 if the decision result is YES. The step S30 performs an operation of deleting an element M[1]→$B_{An}$→b from an array {M[1]→A→b} and subtracting 1 from M[1]→A→nb, with respect to the terminal atoms M[1]→A[M[1]→$B_{An}$→a[1]]=M[1]→$A_{B2n-1}$ and M[1]→A[M[1]→$B_{An}$→a[2]]=M[1]→$A_{B2n}$ on both ends of the bond axis M[1]→$B_{An}$ for which the select bit "Select" is set, according to M[1]→$A_{B1}$→b~=M[1]→$B_{A1}$→b, M[1]→$A_{B2}$→b~=M[1]→$B_{A1}$→b, . . . , M[1]→$A_{B2n-1}$→b~=M[1]→$B_{An}$→b, M[1]→$A_{B2n}$→b~=M[1]→$B_{An}$→b, M[1]→$A_{B1}$→nb=M[1]→$A_{B1}$→nb−1, . . . , M[1]→$A_{B2n}$→nb=M[1]→$B_{B2n}$→nb=M[1]→$A_{B2n}$→nb−1. In this example, the element 2 is deleted from M[1]→AM[1]→b{1, 2} and 1 is subtracted from M[1]→AM[1]→nb, the elements 2 and 4 are deleted from M[1]→AM[3]→b{2, 4} and 2 is subtracted from M[1]→AM[3]→nb, and the element 4 is deleted from M[1]→AM[5]→b{4} and 1 is subtracted from M[1]→AM[5]→nb. A step S31 decides whether M[1]→A(B)→eventFlag=Select, and the process advances to a step S32 if the decision result is YES. The step S32 changes the set select bit "Select" to the delete bit "Delete", according to M[1]→$A_{B1}$→eventFlag=Delete, M[1]→$B_{A1}$→eventFlag=Delete, . . . , M[1]→$B_{An}$→eventFlag=Delete. Hence, a change is made to set the delete bit "Delete" in the event flag "eventFlag" with respect to the atom item and the bond axis item for which the select bit "Select" is set in the event flag "eventFlag".

A step S33 decides whether M[1]→B→eventFlag=Delete, and the process advances to a step S34 if the decision result is YES. The step S34 stores n bond axes M[1]→$B_{An}$ set with the delete bit "Delete" and 2n terminal atoms M[1]→A[M[1]→$B_{An}$→aM[1]]=M[1]→$A_{B2n-1}$ and M[1]→A[M[1]→$B_{An}$→aM[2]]=M[1]→$A_{B2n}$ at both ends into B' and A' of E[M[1]→ne], according to E[M[1]→ne]→A'M[1]=M[1]→$A_{B1}$, . . . , E[M[1]→ne]→A'[2n]=M[1]→$A_{B2n}$, E[M[1]→ne]→B'[1]=M[1]→$B_{A1}$, . . . , E[M[1]→ne]→B'[n]=M[1]→$B_{An}$. Hence, the bond axes B[2} and BM[4] set with the delete bit "Delete" and the terminal atoms AM[1], AM[3] and AM[5] thereof are substituted into the event data as E[M[1]→ne]→A'M[1]=M[1]=M[1]→AM[1], E[M[1]→ne]→A'M[2]=M[1]→AM[3], E[M[1]→ne]→A'M[3]=M[1]→AM[5], E[M[1]→ne]→B'M[1]=M[1]→BM[2], and E[M[1]→ne]→B'[2]=M[1]→B[4].

Finally, a step S35 displays on the display screen 102a items of the atom A and items of the bond axis B, other than those set with the delete bit "Delete", with respect to the molecular data M[1], and the series of operations ends.

FIG. 19 is a diagram illustrating an example of a structural change by the delete event for the formic acid (HCOOH). In FIG. 19, the left side indicates the display state of the molecular structure of the molecular data M[1] on the display screen 102a before and after the delete event, and the right side indicates the change in the structural data of the molecular data M[1] before and after the delete event. FIG. 19 illustrates a case where the selected atom AM[3] is deleted.

Figure 20:
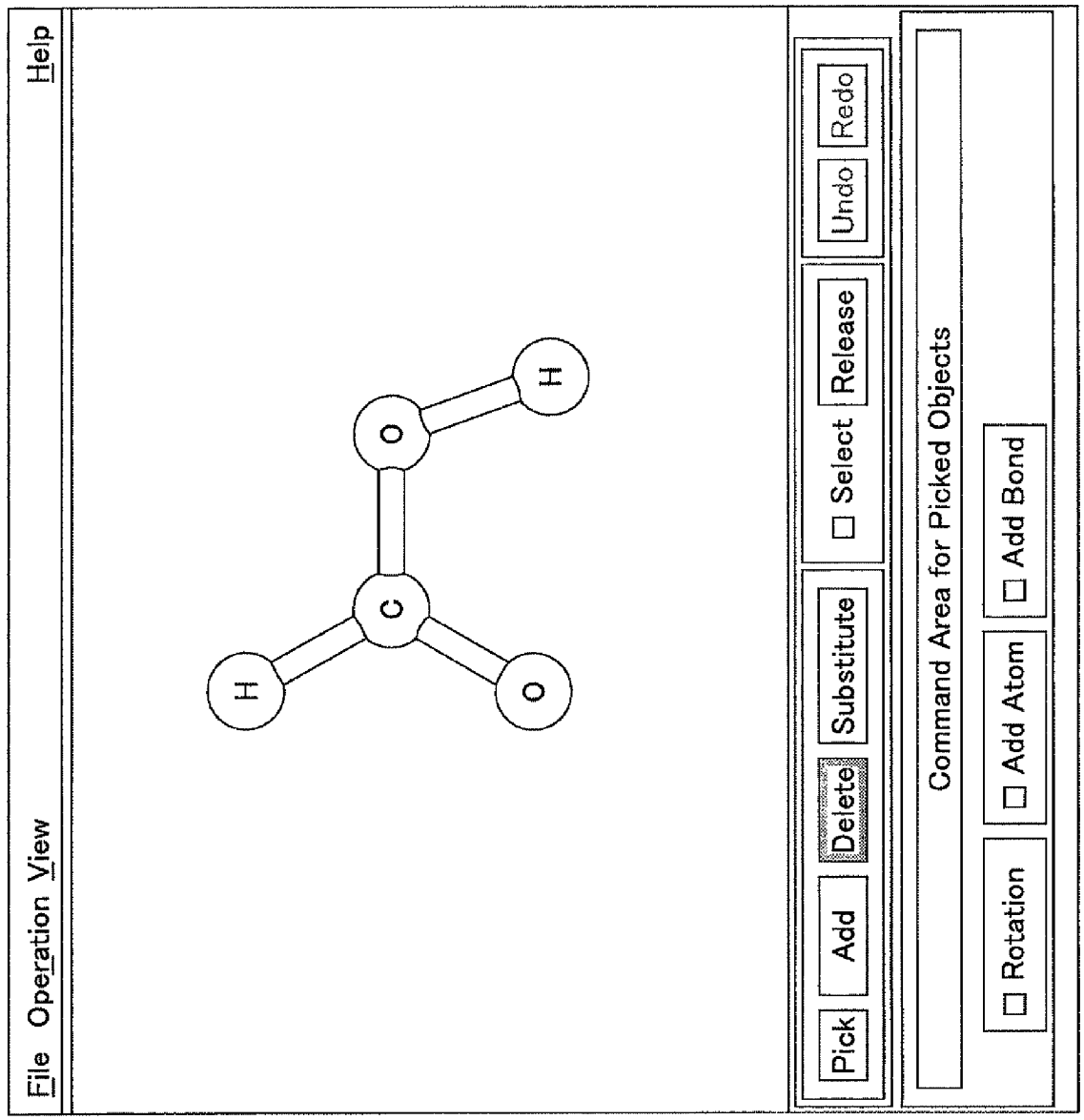
FIG. 20 is a diagram illustrating a display state of the molecular structure before the delete event.
Figure 21:
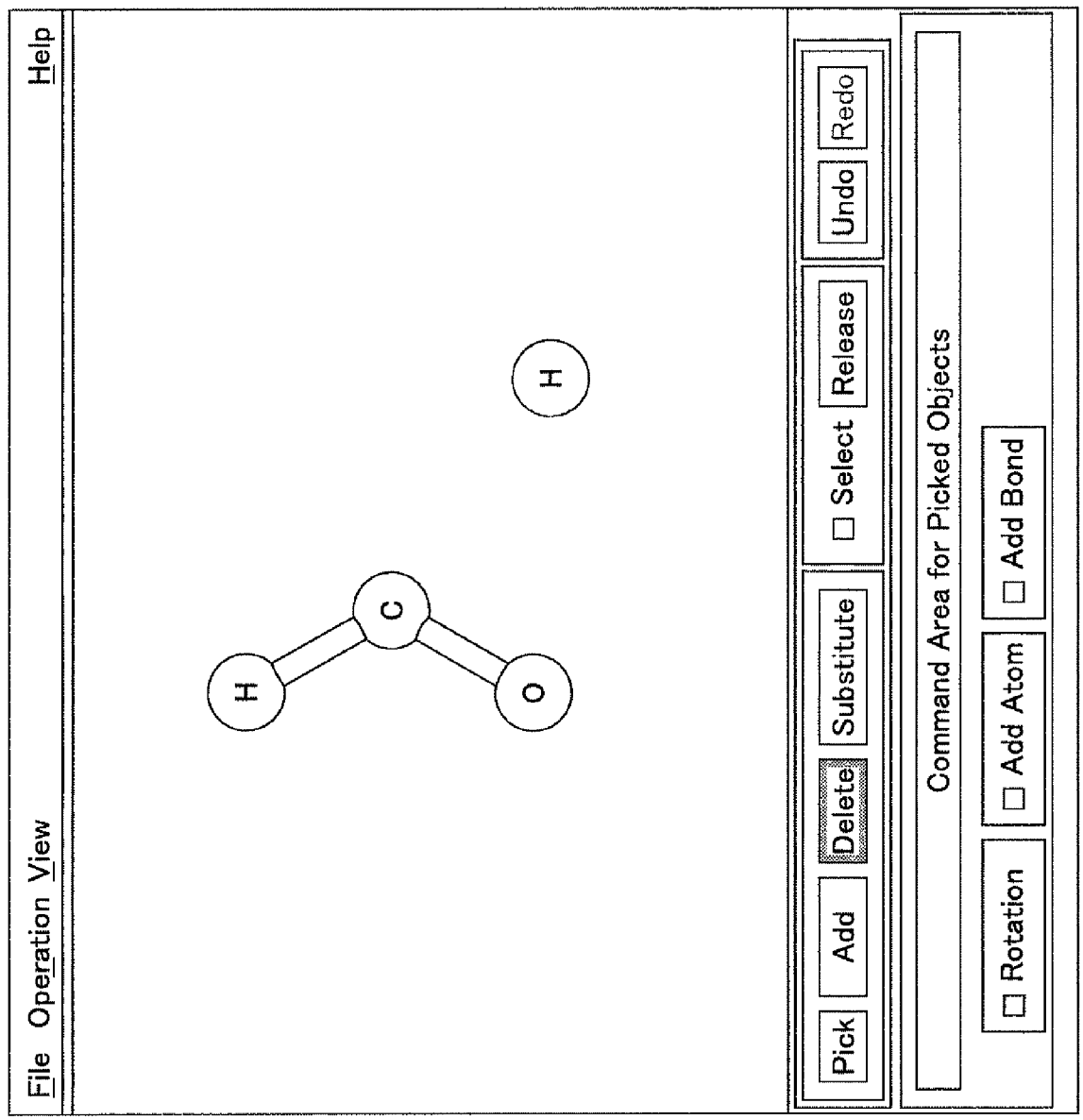
FIG. 21 is a diagram illustrating a display state of the molecular structure after the delete event.

FIG. 20 is a diagram illustrating a display state of the molecular structure on the display screen 102a before the delete event, and FIG. 21 is a diagram illustrating a display state of the molecular structure on the display screen 102a after the delete event. The Undo operation and the Redo operation cannot be performed in the state before the delete event illustrated in FIG. 20. On the other hand, the Undo operation can be performed and the Redo operation cannot be performed in the state after the delete event illustrated in FIG. 21.

Figure 22:
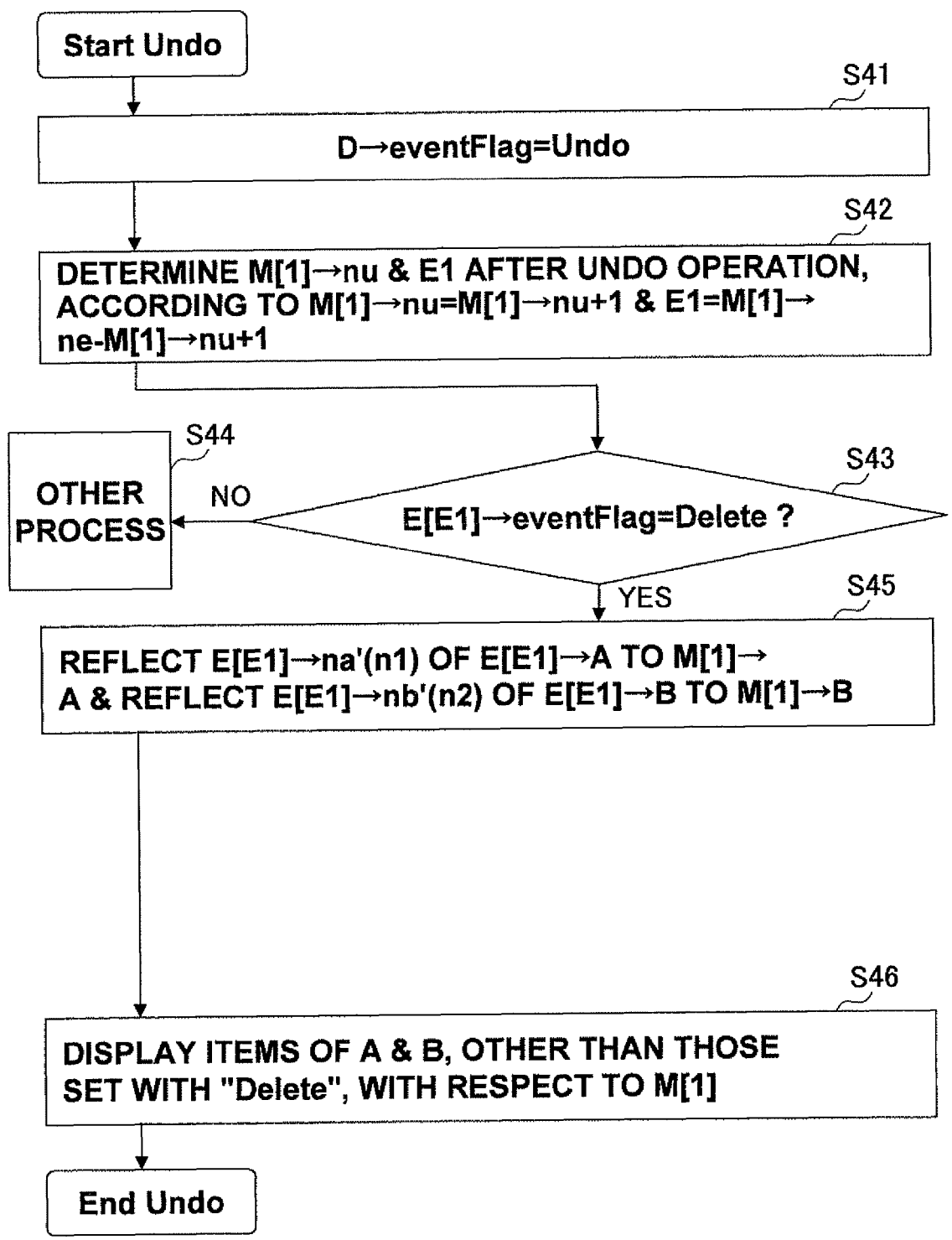
FIG. 22 is a flow chart for explaining the Undo operation of the delete event.

FIG. 22 is a flow chart for explaining the Undo operation of the delete event. When the Undo operation is started, a step S41 sets the event flag "eventFlag" of the auxiliary data to "Undo" according to D→eventFlag=Undo, based on a setting made by the user from the input part. A step S42 determines M[1]→nu and determines an event number E1 after the Undo operation, according to M[1]→nu=M[1]→nu+1 and E1=M[1]→ne-M[1]→nu+1. A step S43 decides whether E[E1]→eventFlag=Delete, and the process advances to a step S44 which performs another process that is not directly related to the subject matter of the present invention if the decision result is NO. On the other hand, the process advances to a step S45 if the decision result in the step S43 is YES.

The step S45 reflects a number E[E1]→na'(n1) of E[E1]→A to M[1]→A, and reflects a number E[E1]→nb'(n2) of E[E1]→B to M[1]→B, according to M[1]→A[E[E1]→AM[1]→a]=E[E1]→AM[1], . . . , M[1]→A[n1]=E[E1]→A[E[E1]→na'], M[1]→B[E[E1]→BM[1]→b]=E[E1]→BM[1], . . . , M[1]→B[n2]=E[E1]→B[E[E1]→nb']. Further, a step S46 displays on the display screen 102a items of the atom A and items of the bond axis B, other than those set with the delete bit "Delete", with respect to the molecular data M[1], and the Undo operation ends.

Figure 23:
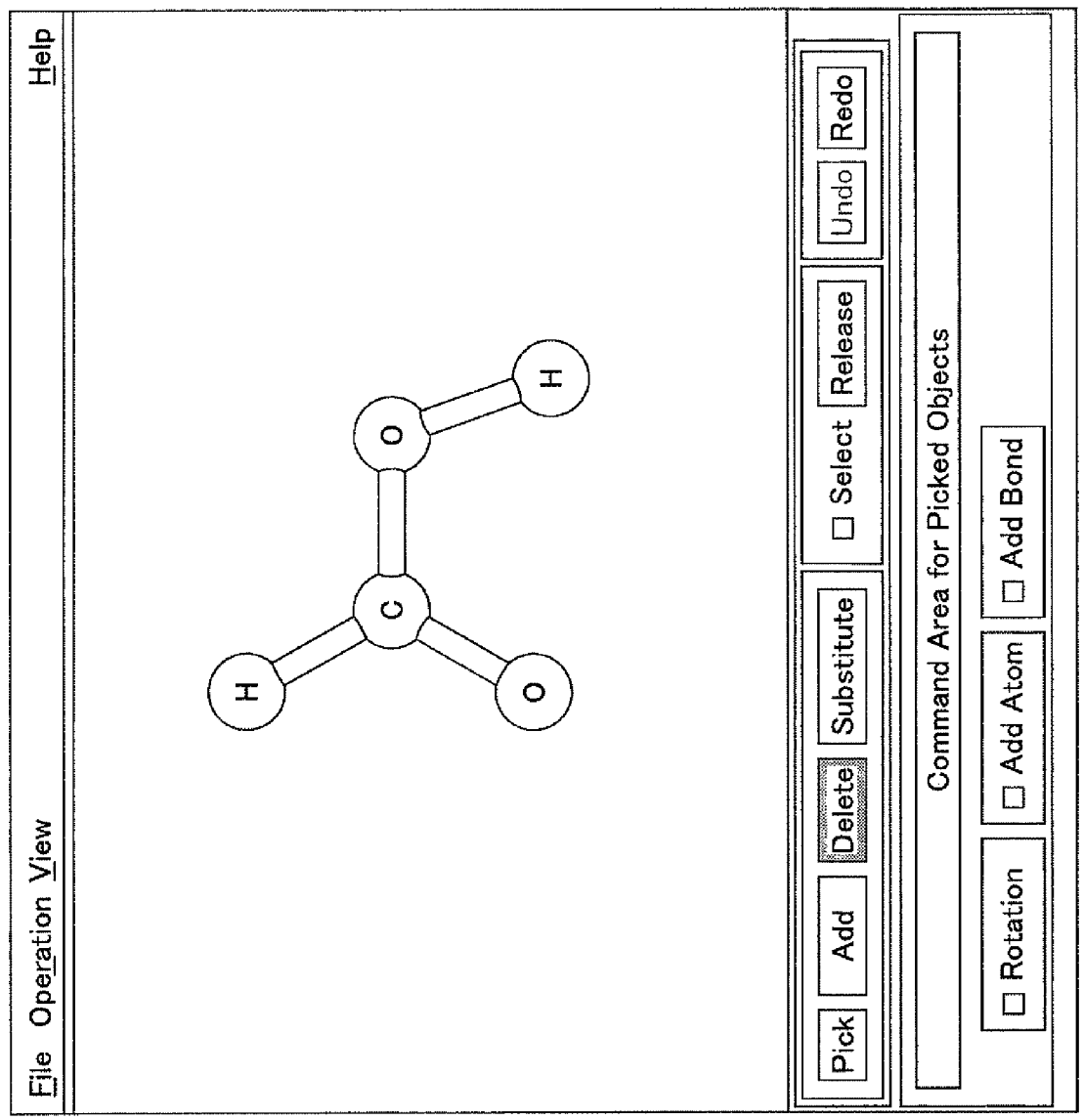
FIG. 23 is a diagram illustrating a display state of the molecular structure after the Undo operation.

FIG. 23 is a diagram illustrating a display state of the molecular structure on the display screen 102a after the Undo operation illustrated in FIG. 22. In the state after the Undo operation illustrated in FIG. 23, the Undo operation cannot be performed, but the Redo operation can be performed.

Figure 24:
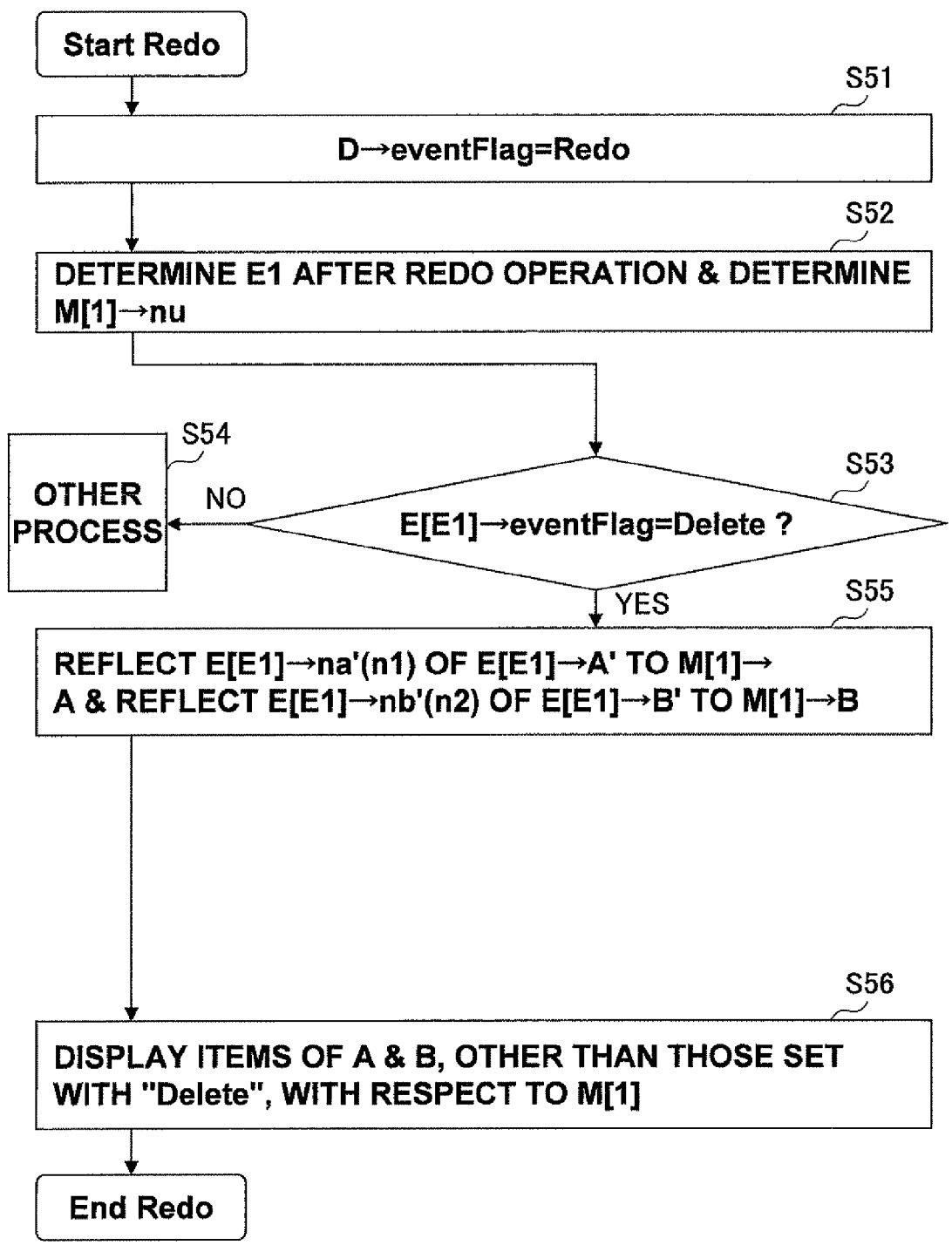
FIG. 24 is a flow chart for explaining the Redo operation of the delete event.

FIG. 24 is a flow chart for explaining the Redo operation of the delete event. When the Redo operation is started, a step S51 sets the event flag "eventFlag" of the auxiliary data to "Redo" according to D→eventFlag=Redo, based on a setting made by the user from the input part. A step S52 determines an event number E1 after the Redo operation and determines M[1]→nu, according to EM[1]=M[1]→ne-M[1]→nu+1 and M[1]→nu=M[1]→nu-1. A step S53 decides whether E[E1]→ eventFlag=Delete, and the process advances to a step S54 which performs another process that is not directly related to the subject matter of the present invention if the decision result is NO. On the other hand, the process advances to a step S55 if the decision result in the step S53 is YES.

The step S55 reflects a number E[E1]→na'(n1) of E[E1]→A' to M[1]→A, and reflects a number E[E1]→nb'(n2) of E[E1]→B' to M[1]→B, according to M[1]→A[E[E1]→A'M[1]→a]=E[E1]→A'M[1], . . . , M[1]→A[n1]=E[E1]→A'[E[E1]→na'], M[1]→B[E[E1]→B'M[1]→b]=E[E1]→B'M[1], . . . , M[1]→B[n2]=E[E1]→B'[E[E1]→nb']. Further, a step S56 displays on the display screen 102a items of the atom A and items of the bond axis B, other than those set with the delete bit "Delete", with respect to the molecular data M[1], and the Redo operation ends.

Figure 25:
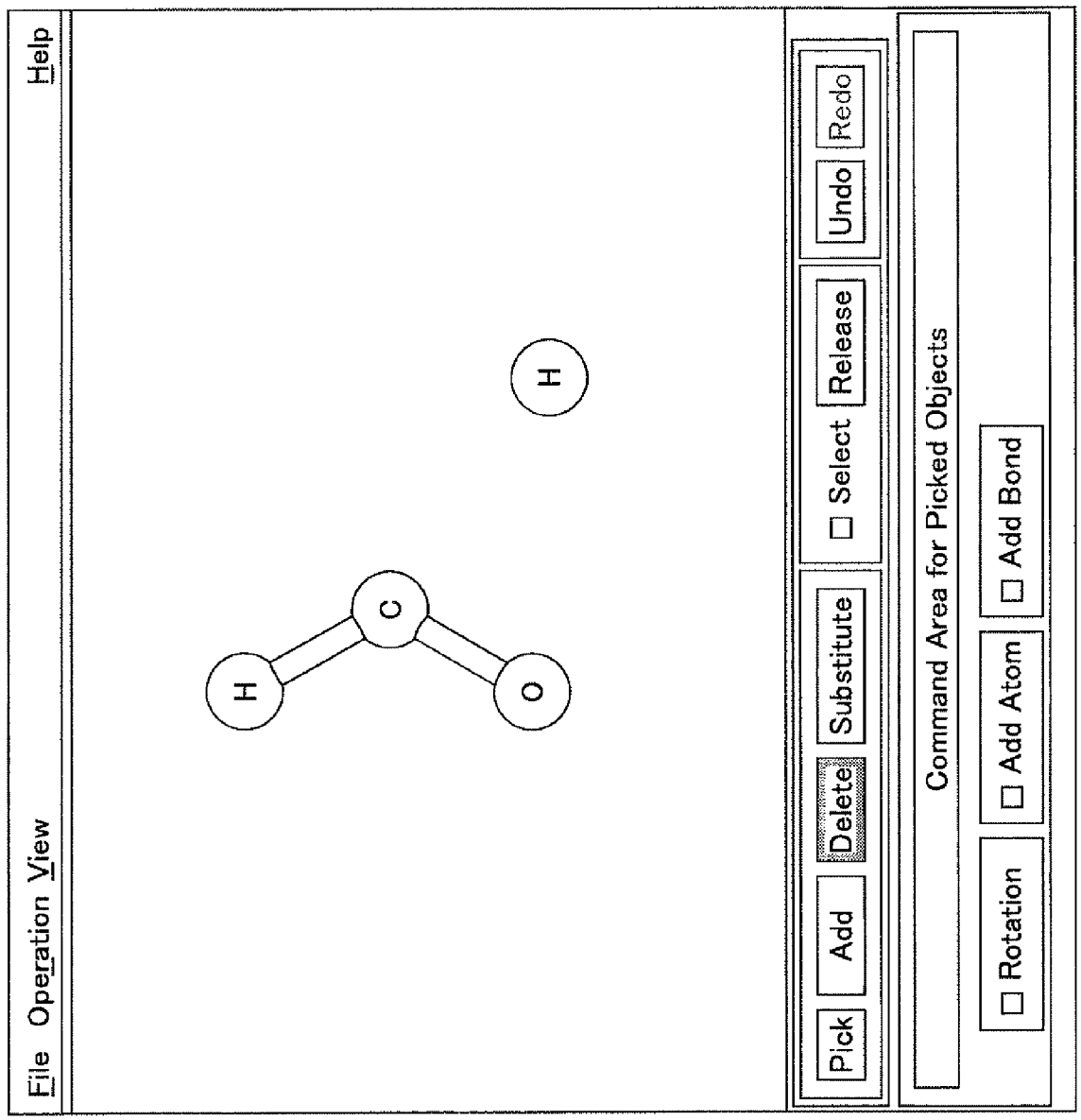
FIG. 25 is a diagram illustrating a display state of the molecular structure after the Redo operation.

FIG. 25 is a diagram illustrating a display state of the molecular structure on the display screen 102a after the Redo operation illustrated in FIG. 24. In the state after the Redo operation illustrated in FIG. 25, the Undo operation can be performed, but the Redo operation cannot be performed.

2. Relationship Among Substitute Event Operation, Undo Operation and Redo Operation:

With respect to the data structure illustrated in FIG. 1 that is constructed by the process illustrated in FIG. 13, the user selects an atom item by clicking the mouse 104, for example, in order to set a select bit "Select" in the event eventFlag" of the selected atom item. This process is represented by M→B→eventFlag=Select or M→A→eventFlag=Select. When the substitute bit "Substitute" is set in the event flag "eventFlag" of the auxiliary data structure "D", a substitute event is executed as illustrated in FIG. 26 in the case of the example illustrated in FIG. 2. FIG. 26 is a diagram illustrating an example of a data change by the substitute event for the formic acid (HCOOH). FIG. 26 illustrates a state before the substitute event, a user input, a substitute event operation, and a state after the substitute event. The event flag "eventFlag" of the auxiliary data structure "D" may be set in advance.

First, the substitute bit "Substitute" and the select bit "Select" are set in the bond axis data corresponding to the bond axis information included in the atom item for which the select bit "Select" is set and the atomic data thereof. Only the select bit "Select" may be set in the bond axis data depending on the algorithm used. Next, a present total event operation number is updated to M→ne=M→ne-M→nu+1, and the Undo event operation number is initialized to M→nu=0. When the total event operation number is updated, the subsequent event data is initialized to E[n>=M→ne]=Null, and the data for the substitute event is substituted into the present event by E[M→ne]→eventFlag=Substitute, . . . , etc. In the case of the substitute event, the information of the atom item and the bond axis information for which the substitute bit "Substitute" or the select bit "Select" is set are registered in the bond axis data before the processing of the event data and the atomic data before the processing of the event data, as well as the numbers thereof. In this state, the substitute bit "Substitute" and the select bit "Select" are reset with respect to the bond axis data before the processing of the event data and the atomic data before the processing of the event data. After the substitution to the event data ends, the atom number information and the bond axis information of the molecular data are updated, and the bond axis information included in the atomic data of the atom item is updated if necessary. In this state, the atomic type after the substitution is changed to the atomic setting information of the auxiliary data according to M→A→Atom=D→Atom. In addition, the vector information of the bond axis data is also updated to match that of the atomic type, if necessary. Finally, the item information for which the substitute bit "Substitute" or the select bit "Select" is set is registered in the bond axis data after the processing of the event data and the atomic data after the processing of the event data. The substitute bit "Substitute" and the select bit "Select" in the bond axis data after the processing of the event data and the atomic data after the processing of the event data are reset when registering the item information in this manner.

The substitute event operation is completed by redisplaying the molecular structure so as to substitute the item for which the substitute bit "Substitute" or the select bit "Select" is set on the main window, after the data updating described above.

The Undo operation related to the substitute event illustrated in FIG. 26 is constructed as illustrated in FIG. 27. FIG. 27 is a diagram for explaining the constructing of the Undo operation related to the substitute event illustrated in FIG. 26. In other words, when an Undo bit is set in the event flag "eventFlag" of the auxiliary data structure "D", the Undo event operation number "nu" is first updated to M→nu=M→nu+1. The corresponding event number is set by the total event operation number and the Undo event operation number according to n=M→ne-M→nu+1, and the data before the processing of the corresponding event data is substituted into the present molecular data. The Undo operation is completed by finally redisplaying the molecular structure on the main window.

The Redo operation related to the Undo operation illustrated in FIG. 27 is constructed as illustrated in FIG. 28. FIG. 28 is a diagram for explaining the constructing of the Redo operation related to the Undo operation illustrated in FIG. 27. In other words, when a Redo bit is set in the event flag "eventFlag" of the auxiliary data structure "D", the corresponding event number is first set by the total event operation number and the Undo event operation number according to n=M→ne-M→nu+1. Then, the Undo event operation number is updated to M→nu=M→nu−1, and the data after the processing of the corresponding event data is substituted into the present molecular data. The Redo operation is completed by finally redisplaying the molecular structure on the main window.

Figure 30:
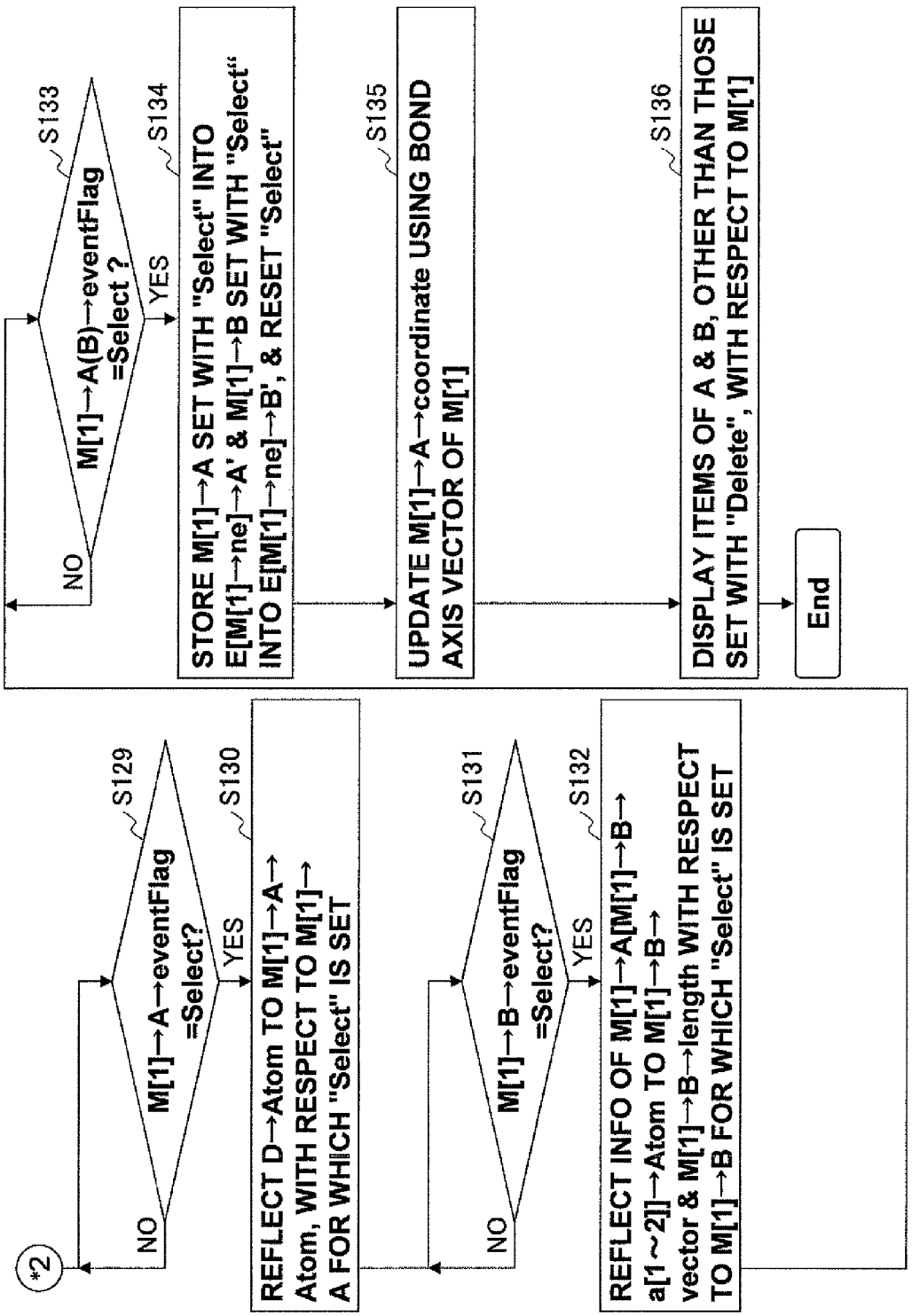
FIG. 30 is a flow chart for explaining the process of the substitute event.

FIGS. 29 and 30 are flow charts for explaining the process of the substitute event.

First, in FIG. 29, a step S121 sets D→eventFlag=Substitute, that is, sets the substitute bit "Substitute" in the event flag "eventFlag" of the auxiliary data structure "D", based on a setting made by the user from the input part. A step S122 selects M[1]→$A_{B1~Bm}$→eventFlag=Select, that is, selects m corresponding items to m atoms $A_{B1}$~$A_{Bm}$ of the molecular data M[1], based on a selection made by the user from the input part. In this example, the atom item AM[3] is selected according to M[1]→AM[3]→eventFlag=Select. Next, a step S123 determines M[1]→ne according to M[1]→ne=M[1]→ne-M[1]→nu+1 and M[1]→nu=0, and E[n]=Null(M[1]→ne<=n<=MaxEvent), and releases the storage part of E[i: i>=M[1]→ne]. In other words, the total event operation number ne of M[1] is determined, and the storage part is released with respect to the M[1]→(ne)th and subsequent event data. A step S124 decides whether M[1]→$A_{B1~Bm}$→b[1~M[1]→$A_{B1~Bm}$→nb]=M M[1]→$B_{Aj(1<=j<=n)}$→b, and the process advances to a step S125 if the decision result is YES. The step S125 sets the select bit "Select" in the event flag "eventFlag" for a total of n bonding axes $B_{A1}$~$B_{An}$, made up of all bond axes linked to the atoms $A_{B1~Bm}$ and the bond axes $B_{A1}$~$B_{Al}$ according to M[1]→$B_{A1}$→eventFlag=Select, . . . , M[1]→$B_{An}$→eventFlag=Select. A step S126 stores setting of the bond axis number n set with the select bit "Select", the number m of terminal atoms at both ends, and D→eventFlag in the event data, according to E[M[1]→ne]→eventFlag=D→eventFlag, E[M[1]→ne]→na'=m, and E[M[1]→ne]→nb'=n. A step S127 decides whether M[1]→B→eventFlag=Select, and the process advances to a step S128 if the decision result is YES.

The step S128 stores n bond axes M[1]→$B_{A1~An}$ set with the select bit "Select" and m terminal atoms M[1]→$A_{B1~Bm}$ at both ends into B and A of E[M[1]→ne], according to E[M[1]→ ne]→AM[1]=M[1]→$A_{B1}$, . . . , E[M[1]→ne]→AM[1]→ eventFlag=Null, . . . , E[M[1]→ne]→A[m]=M[1]→$A_{Bm}$, E[M[1]→ne]→A[m]→eventFlag=Null, E[M[1]→ne]→BM[1]=M[1]→$B_{A1}$, E[M[1]→ne]→BM[1]=eventFlag=Null, . . . , E[M[1]→ne]B[n]=M[1]→$B_{An}$, E[M[1]→ne]→B[n]→eventFlag=Null, and releases the select bit "Select". After the step S128, the process advances to a step S129 illustrated in FIG. 30.

After substituting the data into the event data, the substitute operation actually makes the substitution with respect to the molecular data M[1] as illustrated in FIG. 30. The step S129 decides whether M[1]→A→eventFlag=Select, and the process advances to a step S130 if the decision result is YES. The step S130 performs an operation of reflecting D→Atom to M[1]→A→Atom, with respect to the atom M[1]→A for which the select bit "Select" is set, according to M[1]→$A_{B1}$→Atom=D→Atom, . . . , M[1]→$A_{Bm}$→Atom=D→Atom. A step S131 decides whether M[1]→B→eventFlag=Select, and the process advances to a step S132 if the decision result is YES. The step S132 reflects the information of M[1]→A[M[1]→B →a[1~2]]→Atom to M[1]→B→vector and M[1]→B→length with respect to the bond axis M[1]→B for which the select bit "Select" is set, according to M[1]→$B_{A1}$→vector={x'BA1, y'BA1, z'BA1}, M[1]→$B_{A1}$→length=length'_$B_{A1}$, . . . , M[1]→ $B_{An}$→vector={x'BAn, y'BAn, z'BAn}, M[1]→ $B_{An}$→length=length'_$B_{An}$.

A step S133 decides whether M[1]→A(B)→eventFlag=Select, and the process advances to a step S134 if the decision result is YES. The step S134 stores M[1]→A set with the select flag "Select" into E[M[1]→ne]→A' and M[1]→ B set with the select flag "Select" into E[M[1]→ne]→ B', according to E[M[1]→ne]→A'[1~m]=M[1]→$A_{B1~Bm}$, E[M[1]→ne]→A'[1~m]→eventFlag=Null, E[M[1]→ne]→B'[1~n]=M[1]→$B_{A1~An}$, E[M[1]→ne]→B' [1~n]=eventFlag=Null, and resets the select bit "Select". A step S135 updates M[1]→A→coordinate using the bond axis vector of M[1], according to M[1]→A[i]→coordinate={x'i, y'i, z'i} (where 1<=i<=M[1]→na), M[1]→A[i]→eventFlag~=Select (where 1<=i<=M[1]→na), and M[1]→B [j]→eventFlag~=Select (where 1<=j<=M[1]→nb), and resets all of the select bits "Select" of the atom and bond axis.

Finally, a step S136 displays on the display screen 102a items of the atom A and items of the bond axis B, other than those set with the delete bit "Delete", with respect to the molecular data M[1], and the series of operations ends.

Figure 31:
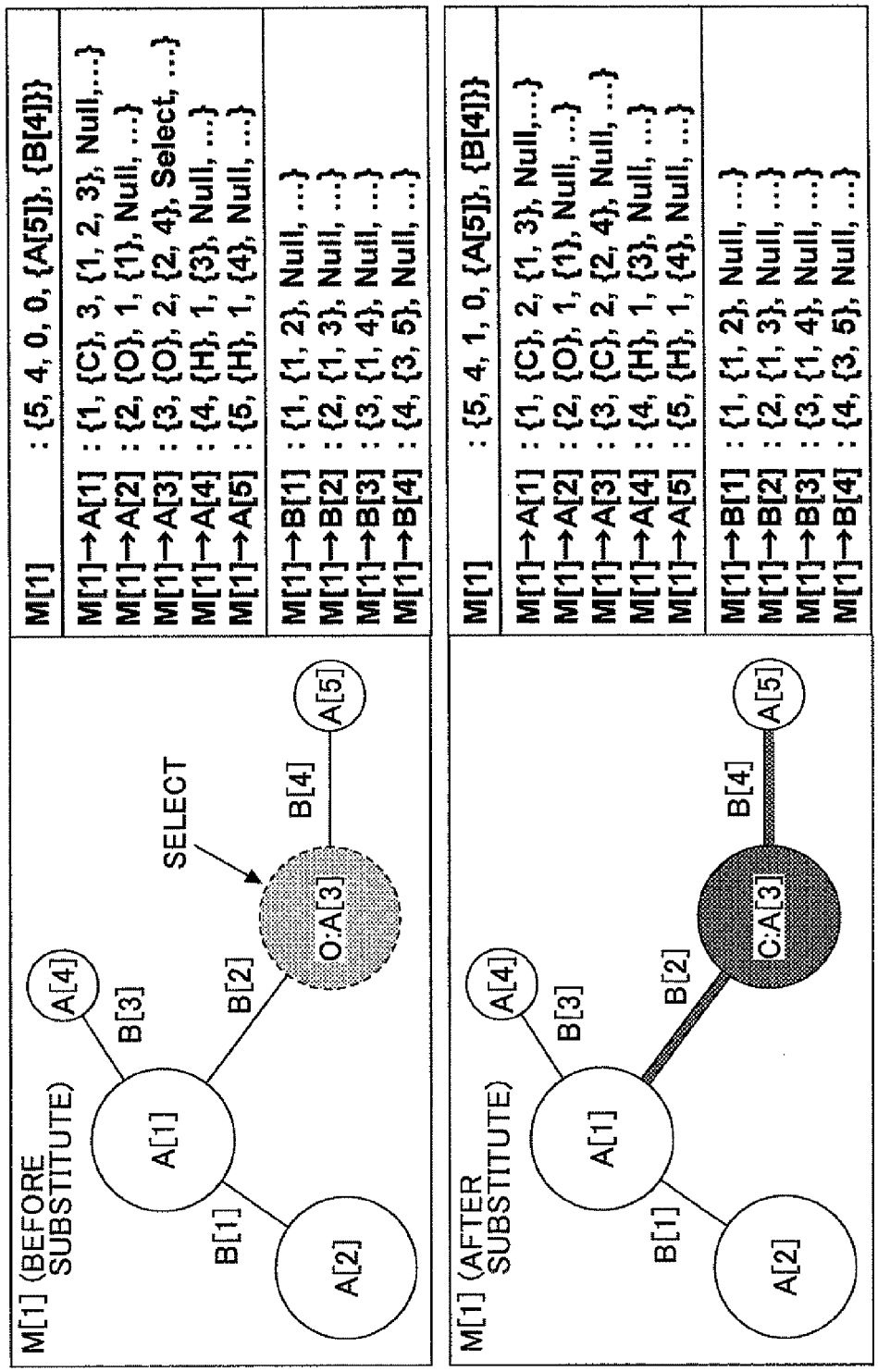
FIG. 31 is a diagram illustrating an example of a structural change by the substitute event for the formic acid (HCOOH)

FIG. 31 is a diagram illustrating an example of a structural change by the substitute event for the formic acid (HCOOH). In FIG. 31, the left side indicates the display state of the molecular structure of the molecular data M[1] on the display screen 102a before and after the substitute event, and the right side indicates the change in the structural data of the molecular data M[1] before and after the substitute event. FIG. 31 illustrates a case where an oxygen atom AM[3] indicated by "O" is substituted by a carbon atom A[3} indicated by "C".

Figure 32:
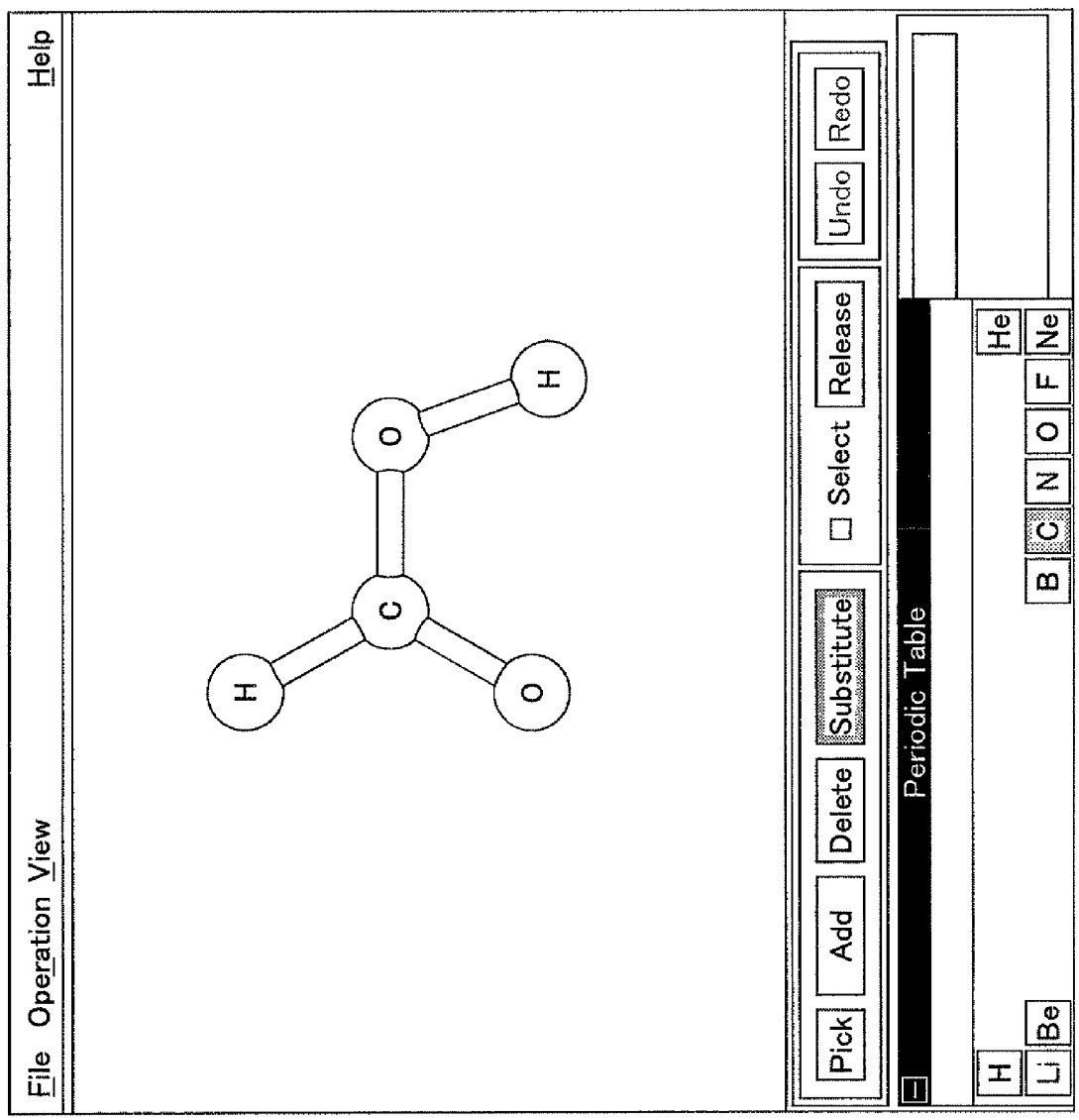
FIG. 32 is a diagram illustrating a display state of the molecular structure before the substitute event.
Figure 33:
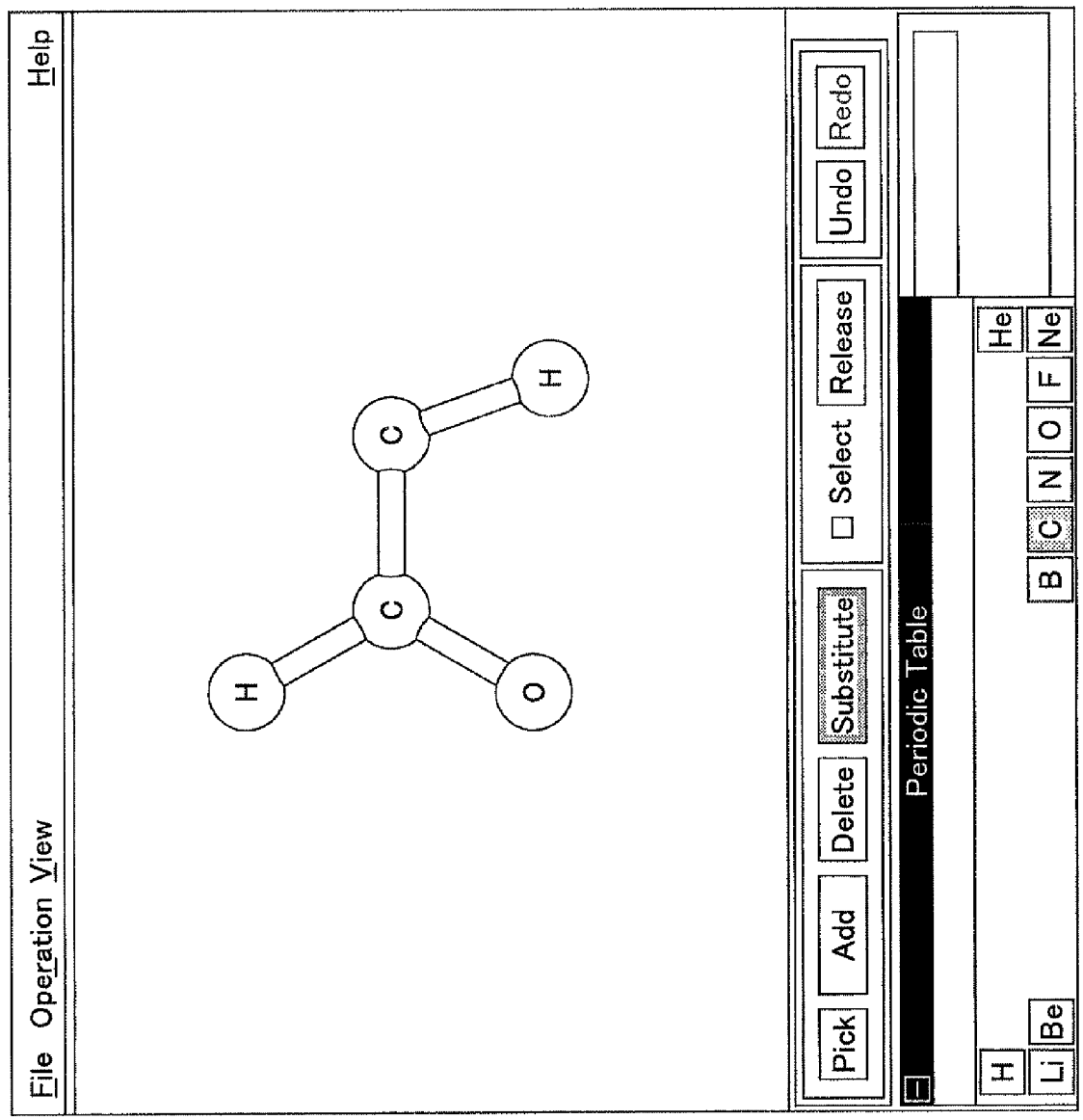
FIG. 33 is a diagram illustrating a display state of the molecular structure after the substitute event.

FIG. 32 is a diagram illustrating a display state of the molecular structure on the display screen 102a before the substitute event, and FIG. 33 is a diagram illustrating a display state of the molecular structure on the display screen 102a after the substitute event. The Undo operation and the Redo operation cannot be performed in the state before the substitute event illustrated in FIG. 32. On the other hand, the Undo operation can be performed and the Redo operation cannot be performed in the state after the substitute event illustrated in FIG. 33.

Figure 34:
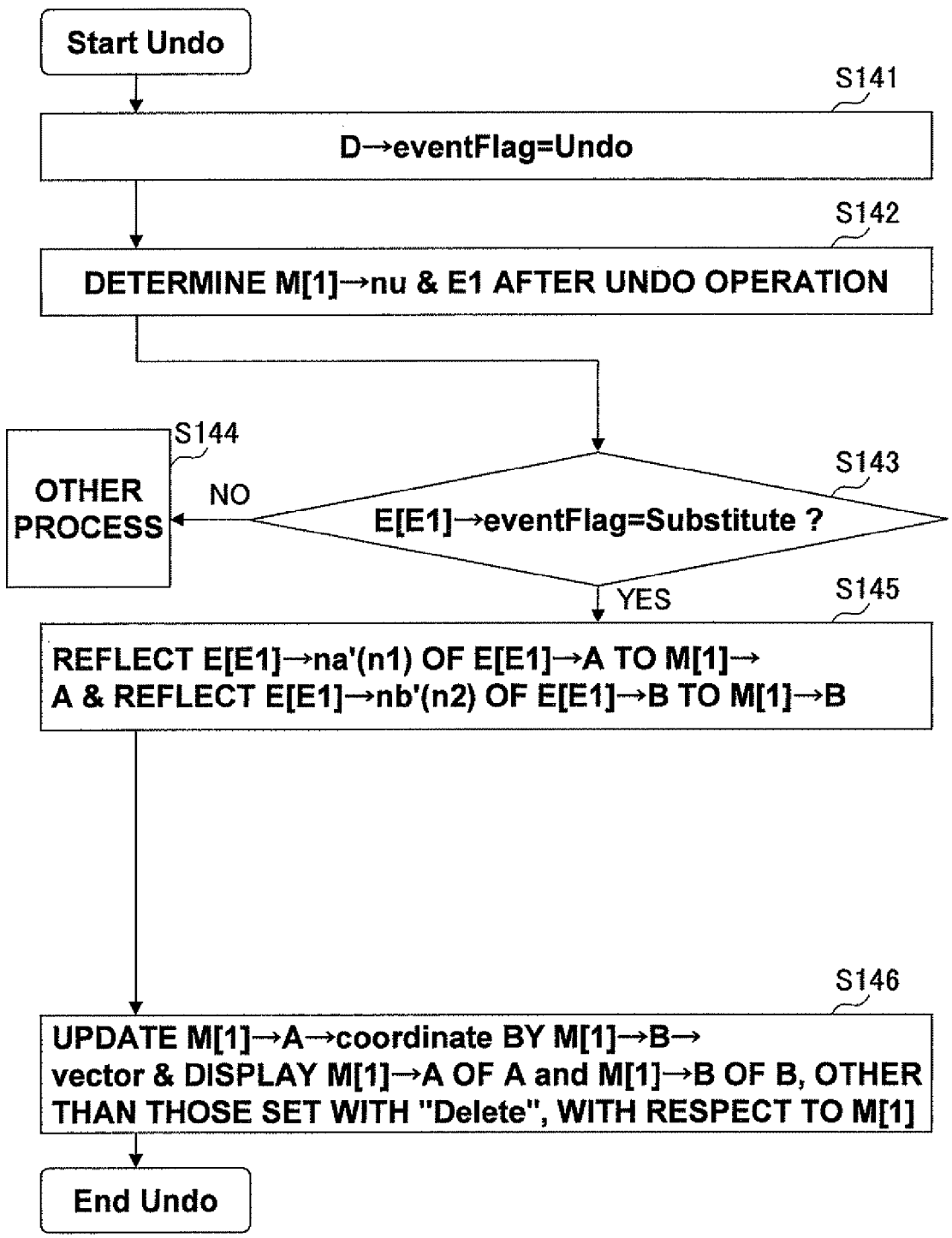
FIG. 34 is a flow chart for explaining an Undo operation of the substitute event.

FIG. 34 is a flow chart for explaining the Undo operation of the substitute event. When the Undo operation is started, a step S141 sets the event flag "eventFlag" of the auxiliary data to "Undo" according to D→eventFlag=Undo, based on a setting made by the user from the input part. A step S142 determines M[1]→nu and determines an event number E1 after the Undo operation, according to M[1]→nu=M[1]→nu+1 and E1=M[1]→ne-M[1]→nu+1. A step S143 decides whether E[E1]→eventFlag=Substitute, and the process advances to a step S144 which performs another process that is not directly related to the subject matter of the present invention if the decision result is NO. On the other hand, the process advances to a step S145 if the decision result in the step S143 is YES.

The step S145 reflects a number E[E1]→na'(n1) of E[E1]→ A to M[1]→A, and reflects a number E[E1]→nb' (n2) of E[E1]→B to M[1]→B, according to M[1]→A[E[E1]→AM[1]→a]=E[E1]→AM[1], . . . , M[1]→A[n1]=E[E1]→A[E[E1]→na'], M[1]→B[E[E1]→BM[1]→b]=E[E1]→BM[1], . . . , M[1]→B[n2]=E[E1]→B [E[E1]→nb']. Further, a step S146 updates M[1]→A→coordinate by M[1]→B→vector, and displays on the display screen 102a items M[1]→A of the atom A and items M[1]→B of the bond axis B, other than those set with the delete bit "Delete", with respect to the molecular data M[1], and the Undo operation ends.

Figure 35:
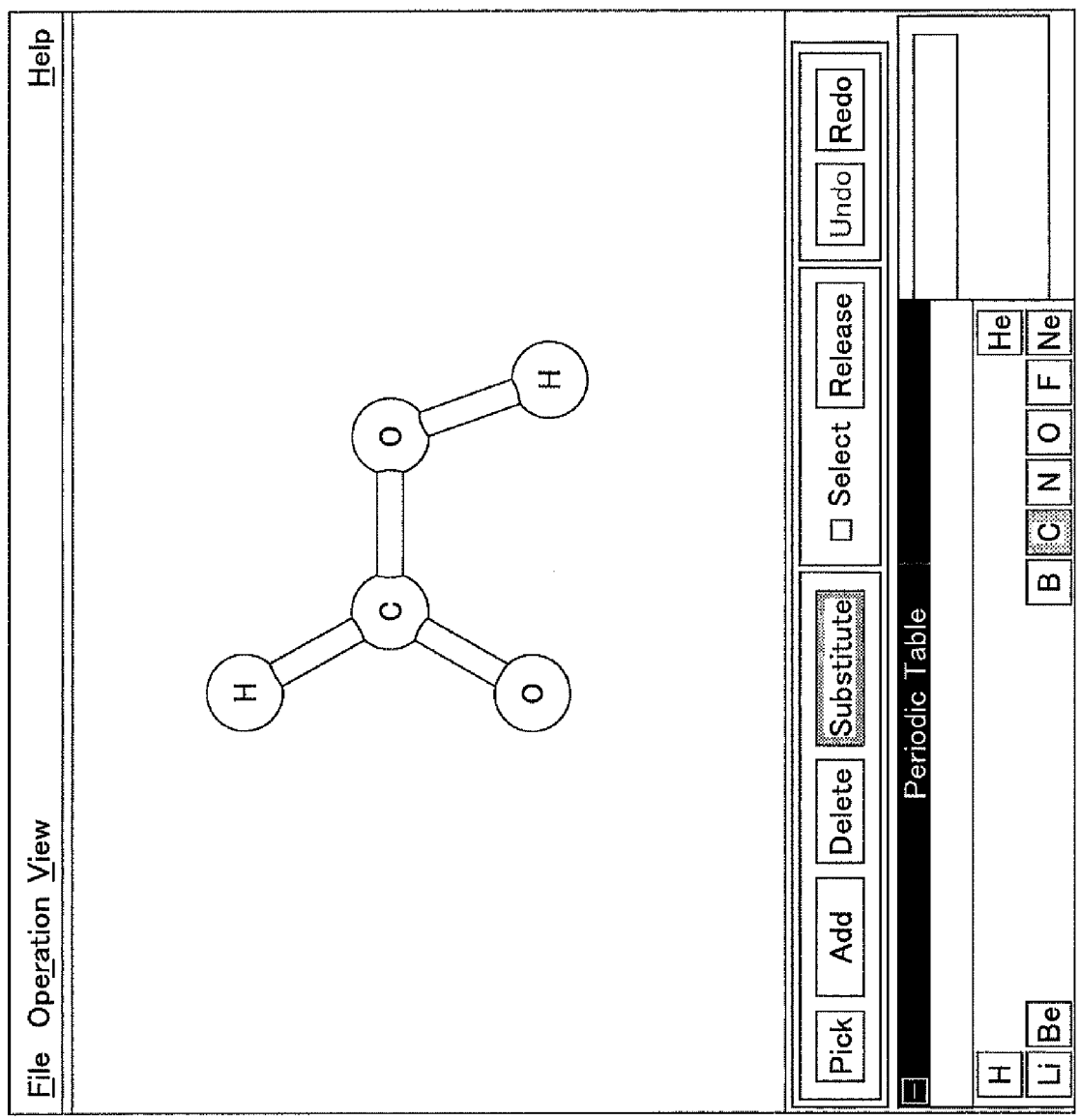
FIG. 35 is a diagram illustrating a display state of the molecular structure after the Undo operation.

FIG. 35 is a diagram illustrating a display state of the molecular structure on the display screen 102a after the Undo operation illustrated in FIG. 34. In the state after the Undo operation illustrated in FIG. 35, the Undo operation cannot be performed, but the Redo operation can be performed.

Figure 36:
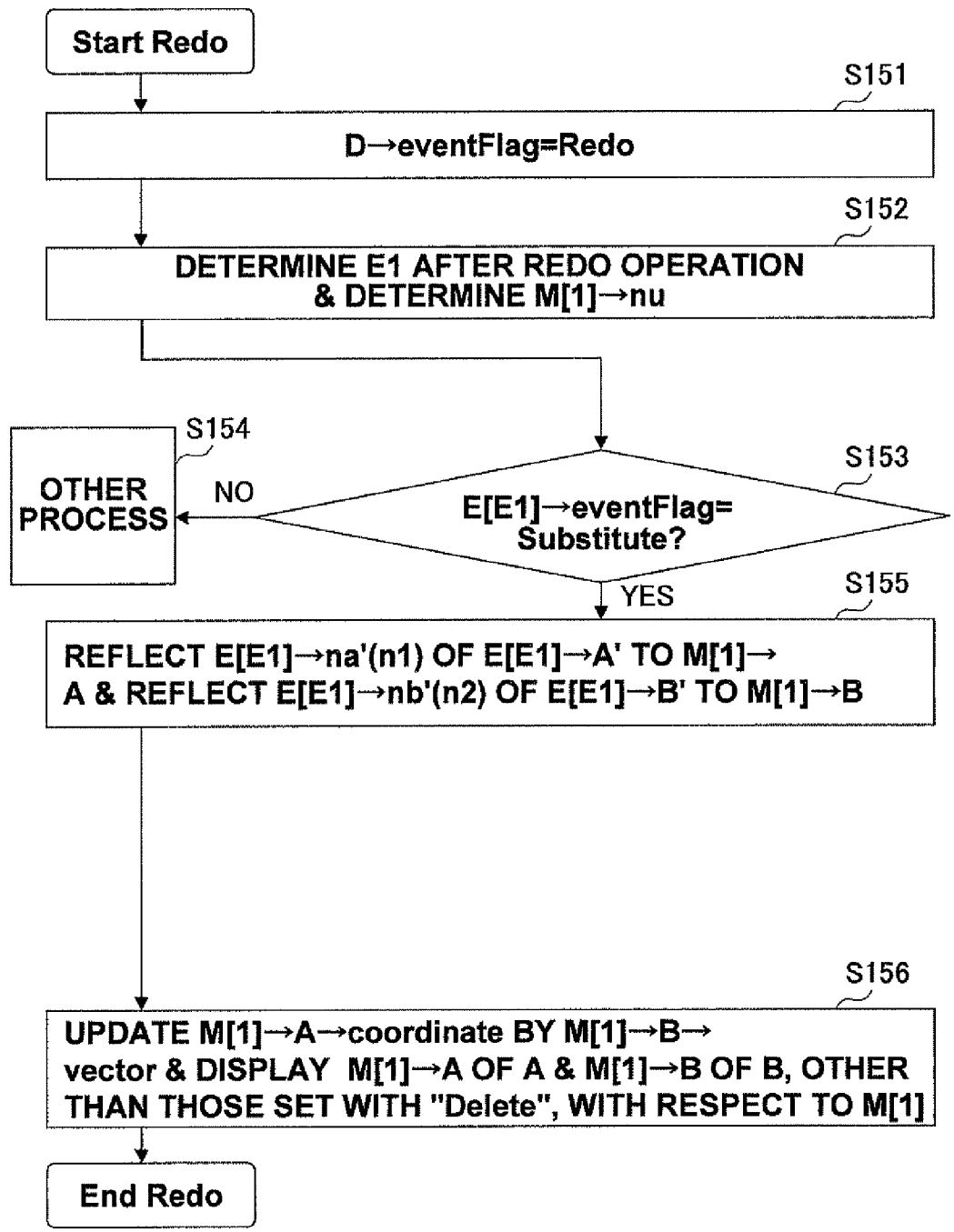
FIG. 36 is a flow chart for explaining a Redo operation of the substitute event.

FIG. 36 is a flow chart for explaining the Redo operation of the substitute event. When the Redo operation is started, a step S151 sets the event flag "eventFlag" of the auxiliary data to "Redo" according to D→eventFlag=Redo, based on a setting made by the user from the input part. A step S152 determines an event number E1 after the Redo operation and determines M[1]→nu, according to EM[1]=M[1]→ne−M[1]→nu+1 and M[1]→nu=M[1]→nu−1. A step S153 decides whether E[E1]→eventFlag=Substitute, and the process advances to a step S154 which performs another process that is not directly related to the subject matter of the present invention if the decision result is NO. On the other hand, the process advances to a step S155 if the decision result in the step S153 is YES.

The step S155 reflects a number E[E1]→na'(n1) of E[E1]→A' to M[1]→A, and reflects a number E[E1]→nb' (n2) of E[E1]→B' to M[1]→B, according to M[1]→A[E[E1]→A'M[1]→a]=E[E1]→A'M[1], . . . , M[1]→A[n1]=E[E1]→A'[E[E1]→na'], M[1]→B[E[E1]→B'M[1]b]=E[E1]→B'M[1], . . . , M[1]→B[n2]=E[E1]→B'[E[E1]→nb']. Further, a step S156 updates M[1]→A→coordinate by M[1]→B→vector, and displays on the display screen 102a items M[1]→A of the atom A and items M[1]→B of the bond axis B, other than those set with the delete bit "Delete", with respect to the molecular data M[1], and the Redo operation ends.

Figure 37:
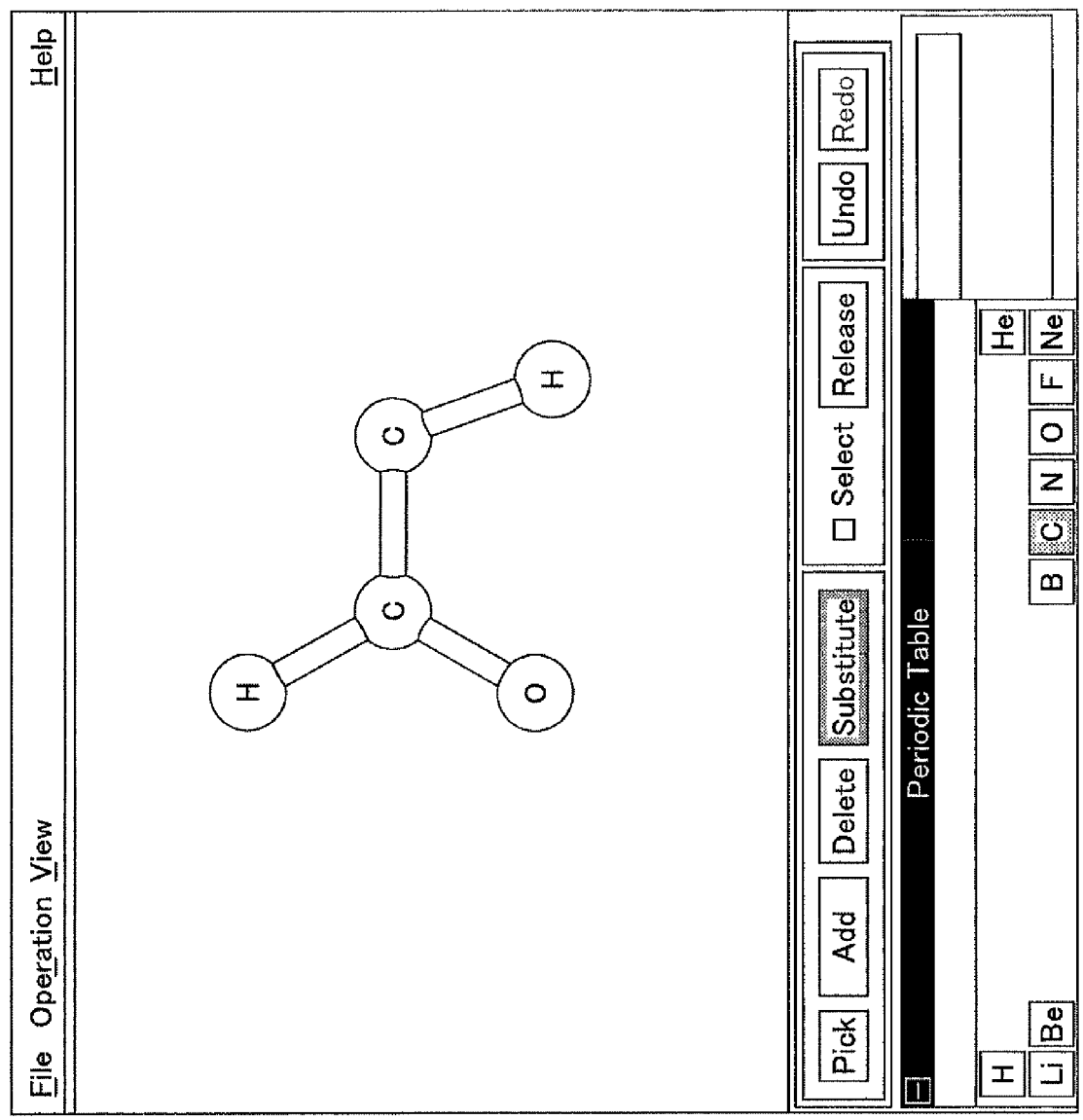
FIG. 37 is a diagram illustrating a display state of the molecular structure after the Redo operation.

FIG. 37 is a diagram illustrating a display state of the molecular structure on the display screen 102a after the Redo operation illustrated in FIG. 36. In the state after the Redo operation illustrated in FIG. 37, the Undo operation can be performed, but the Redo operation cannot be performed.

3. Relationship Among Add Event Operation, Undo Operation and Redo Operation:

With respect to the data structure illustrated in FIG. 1 that is constructed by the process illustrated in FIG. 13, the user selects an atom item by clicking the mouse 104, for example, in order to set a select bit "Select" in the event flag "eventFlag" of the selected atom item. This process is represented by M→B→eventFlag=Select or M→A→eventFlag=Select. When the add bit "Add" is set in the event flag "eventFlag" of the auxiliary data structure "D", an add event is executed as illustrated in FIG. 38 in the case of the example illustrated in FIG. 2. FIG. 38 is a diagram illustrating an example of a data change by the add event for the formic acid (HCOOH). FIG. 38 illustrates a state before the add event, a user input, an add event operation, and a state after the add event. The event flag "eventFlag" of the auxiliary data structure "D" may be set in advance. FIG. 38 illustrates a case where HCOOH changes to $CH_3COOH$ by the add event.

First, the add bit "Add" and the select bit "Select" are set in the bond axis data corresponding to the bond axis information included in the atomic data for which the select bit "Select" is set and the atomic data thereof. Only the select bit "Select" may be set in the bond axis data depending on the algorithm used. Next, a present total event operation number is updated to M→ne=M→ne−M→nu+1, and the Undo event operation number is initialized to M→nu=0. When the total event operation number is updated, the subsequent event data is initialized to E[n>=M→ne]=Null, and the data for the add event is substituted into the present event by E[M→ne]→eventFlag=Add, . . . , etc. In the case of the add event, the information of the atom item and the bond axis information for which the add bit "Add" or the select bit "Select" is set are registered in the bond axis data before the processing of the event data and the atomic data before the processing of the event data, as well as the numbers thereof. In this state, the add bit "Add" and the select bit "Select" are reset with respect to the bond axis data before the processing of the event data and the atomic data before the processing of the event data. The partial structure to be added is loaded from the storage part, for example, using the molecule setting information included in the auxiliary data. After the substitution to the event data ends, the atom number information of the molecular data, the bond axis information, the atomic data and the bond axis data are updated in the form of adding the loaded data of the partial structure, and the vector information of the bond axis information is updated to match the atomic type substituted by the add event operation if necessary. The atomic data after the substitution and the bond axis data related thereto are substituted into the atomic data after processing of and included in the event data and the bond axis data after the processing of and included in the event data.

The add event operation is completed by redisplaying the molecular structure so as to add the item for which the add bit "Add" or the select bit "Select" is set, after the data updating described above.

The Undo operation related to the add event illustrated in FIG. 38 is constructed as illustrated in FIG. 39. FIG. 39 is a diagram for explaining the constructing of the Undo operation related to the add event illustrated in FIG. 38. In other words, when an Undo bit is set in the event flag "eventFlag" of the auxiliary data structure "D", the Undo event operation number "nu" is first updated to M→nu=M→nu+1. The corresponding event number is set by the total event operation number and the Undo event operation number according to n=M→ne−M→nu+1, and the atom number (or number of atoms) and the bond axis number (or number of bond axes) in the partial structure included in the corresponding event data are subtracted from the atom number and the bond axis number in the present molecular data. The data of the corresponding event data, before the processing of the corresponding data, is substituted into the present molecular data. Finally, the Undo operation is completed by finally redisplaying only the items matching the atom number and the bond axis number of the molecular data on the main window.

The Redo operation related to the Undo operation illustrated in FIG. 39 is constructed as illustrated in FIG. 40. FIG. 40 is a diagram for explaining the constructing of the Redo operation related to the Undo operation illustrated in FIG. 39. In other words, when a Redo bit is set in the event flag "eventFlag" of the auxiliary data structure "D", the corresponding event number is first set by the total event operation number and the Undo event operation number according to n=M→ne−M→nu+1. Then, the Undo event operation number is updated to M→nu=M→nu−1, the atom number and the bond axis number of the partial structure included in the corresponding event data are added, and the data after the processing of the corresponding event data is substituted into the present molecular data. The Redo operation is completed by finally redisplaying the molecular structure on the main window.

Figure 41:
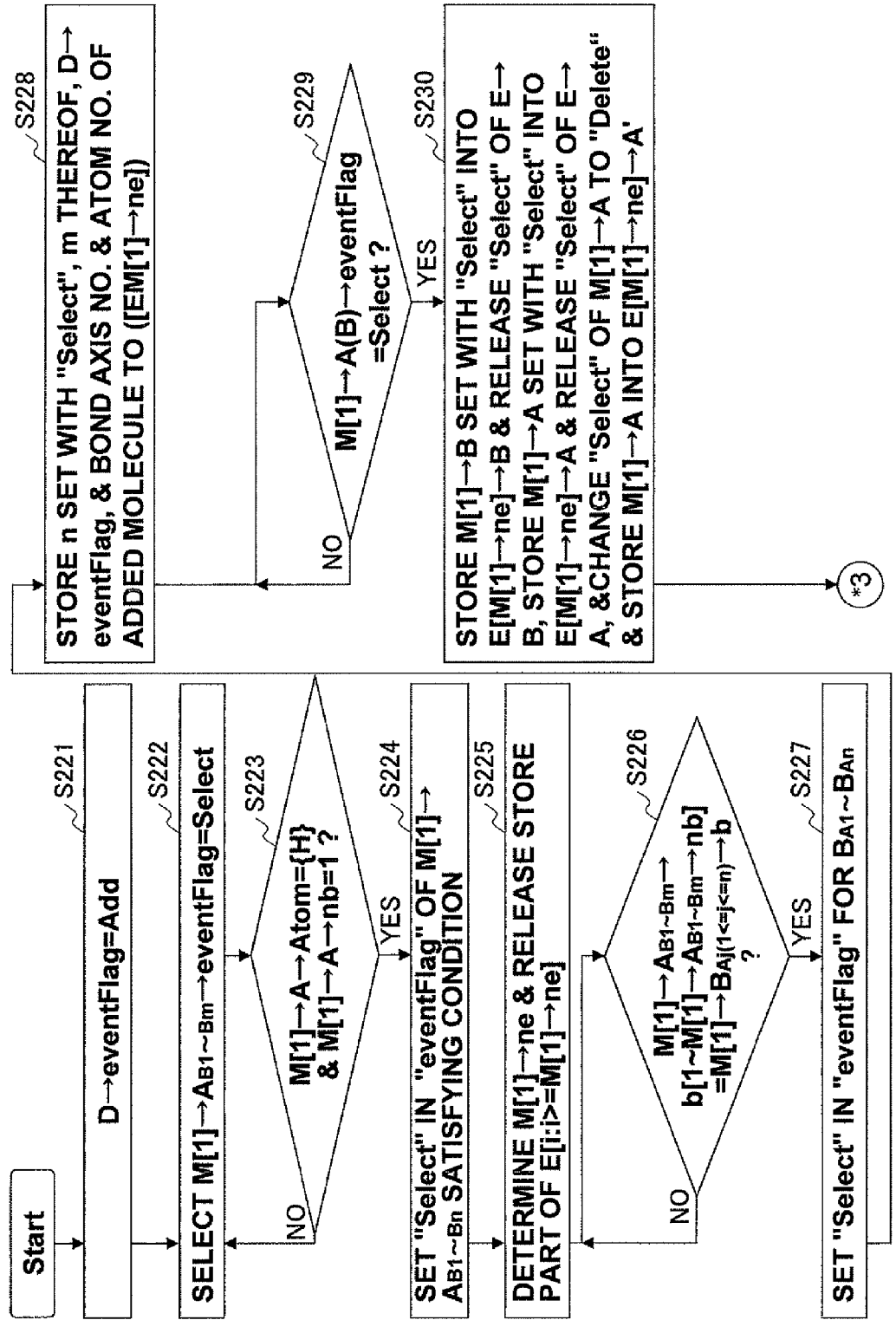
FIG. 41 is a flow chart for explaining a process of the add event.
Figure 42:
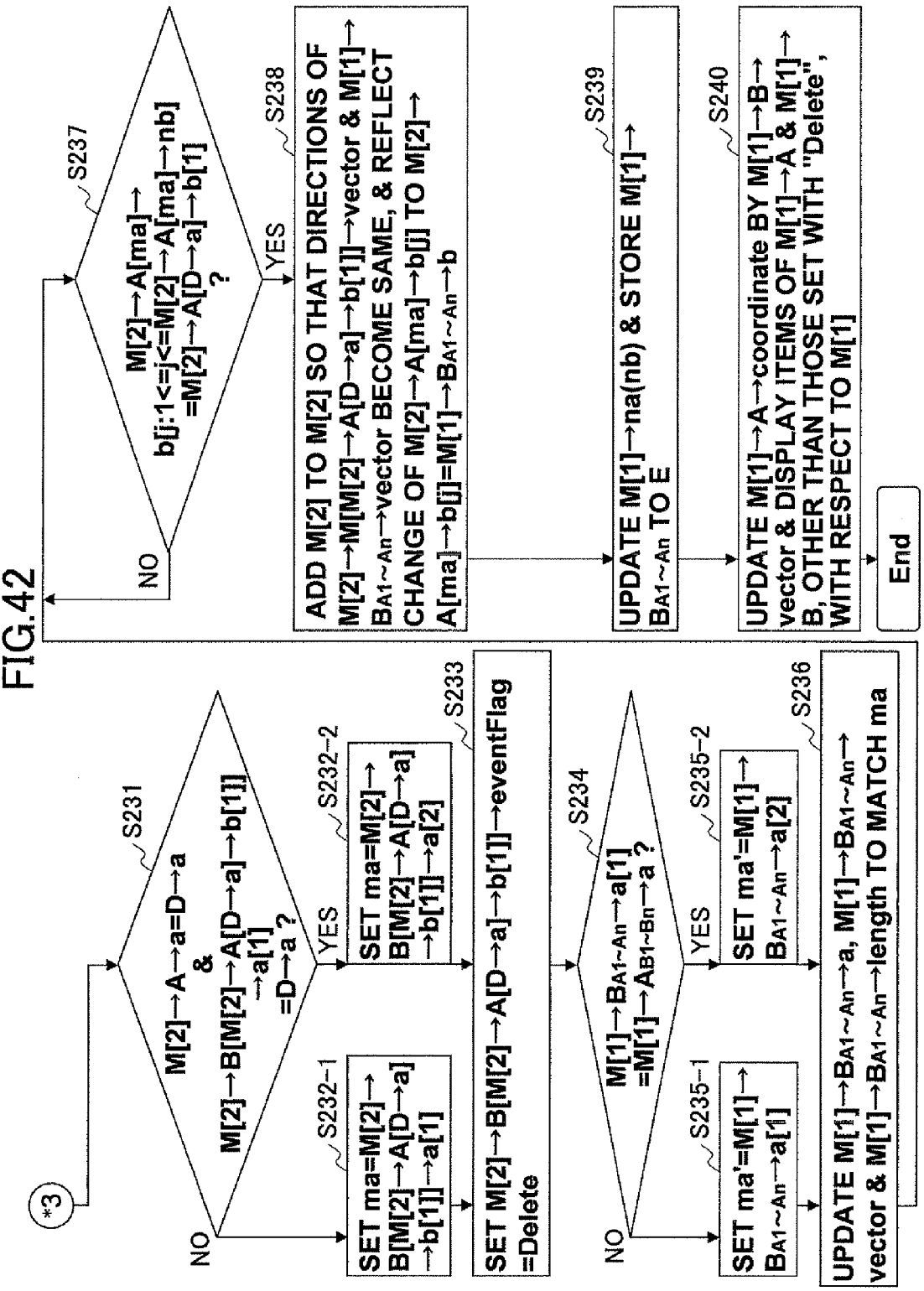
FIG. 42 is a flow chart for explaining the process of the add event.

FIGS. 41 and 42 are flow charts for explaining the process of the add event.

First, in FIG. 41, a step S221 sets D→eventFlag=Add, that is, sets the add bit "Add" in the event flag "eventFlag" of the auxiliary data structure "D", based on a setting made by the user from the input part. A step S222 selects M[1]→$A_{B1 \sim Bm}$→eventFlag=Select, that is, selects m corresponding items to m atoms $A_{B1} \sim A_{Bm}$ of the molecular data M[1], based on a selection made by the user from the input part. In this example, the atom item AM[4] is selected according to M[1]→AM[4]→eventFlag=Select. Next, a step S223 decides whether M[1]→A→Atom={H} and M[1]→A→nb=1, and the process advances to a step S224 if the decision result is YES. The step S224 sets the select bit "Select" in the event flag "eventFlag" of M[1]→$A_{B1~Bn}$ satisfying the condition according to M[1]→$A_{B1~Bn}$→eventFlag=Select. A step S225 determines M[1]→ne according to M[1]→ne=M[1]→ne−M[1]→nu+1, M[1]→nu=0, and E[n]=Null(M[1]→ne<=n<=MaxEvent), and releases the storage part of E[i:i>=M[1]→ne]. In other words, the total event operation number ne of M[1] is determined, and the storage part is released with respect to the M[1]→(ne)th and subsequent event data. A step S226 decides whether M[1]→$A_{B1~Bm}$→b[1~M[1]→$A_{B1~Bm}$→nb]=M[1]→$B_{Aj(1<=j<=n)}$→b, and the process advances to a step S227 if the decision result is YES. The step S227 sets the select bit "Select" in the event flag "eventFlag" for a total of n bonding axes $B_{A1}$~$B_{An}$ made up of all bond axes linked to the atoms $A_{B1~Bm}$ and the bond axes $B_{A1}$~$B_{Al}$ according to M[1]→$B_{A1~An}$→eventFlag=Select. A step S228 stores the bond axis number n set with the select bit "Select", the terminal atom number m thereof, D→eventFlag, and the bond axis number and the atom number of the added molecule to the event data ([EM[1]→ne]), according to E[M[1]→ne]→eventFlag=D→eventFlag, E[M[1]→ne]→na=M[2]→na, E[M[1]→ne]→nb=M[2]→nb, E[M[1]→ne]→n, and E[M[1]→ne]→nb'=n. A step S229 decides whether M[1]→A(B)→eventFlag=Select, and the process advances to a step S230 if the decision result is YES.

The step S230 stores M[1]→B set with the select bit "Select" into E[M[1]→ne]→B and releases the select bit "Select" of E→B, stores M[1]→A set with the select bit "Select" into E[M[1]→ne]→A and releases the select bit "Select" of E→A, and changes the set select bit "Select" of M[1]→A to the delete bit "Delete" and stores M[1]→A into E[M[1]→ne]→A', according to E[M[1]→ne]→A[1~n]=M[1]→$A_{B1~Bn}$, ..., E[M[1]→ne]→A[1~n]→eventFlag=Null, E[M[1]→ne]→B[1~n]=M[1]→$B_{A1~Ab}$→ eventFlag=Delete, E[M[1]→ne]→A'[1~n]=M[1]→$A_{B1~Bn}$, and releases the select bit "Select". After the step S230, the process advances to a step S231 illustrated in FIG. 42.

After substituting the data into the event data, the add operation actually adds to the molecular data M[1] as illustrated in FIG. 42. The step S231 decides whether M[2]→A→a=D→a and M[2]→B[M[2]→A[D→a]→bM[1]]→aM[1]=D→a, and the process advances to a step S232-1 if the decision result is NO, and the process advances to a step S232-2 if the decision result is YES. The step S232-1 sets ma=M[2]→B[M[2]→A[D→a]→bM[1]]→aM[1], and the process advances to a step S233. The step S232-2 sets ma=M[2]→B[M[2]→A[D→a]→bM[1]]→aM[2], and the process advances to the step S233. The step S233 sets M[2]→B[M[2]→A[D→a]→bM[1]]→eventFlag=Delete, and the process advances to a step S234.

The step S234 decides whether M[1]→$B_{A1~An}$→aM[1]=M[1]→$A_{B1~Bn}$→a, and the process advances to a step S235-1 if the decision result is NO, and the process advances to a step S235-2 if the decision result is YES. The step S235-1 sets ma'=M[1]→$B_{A1~An}$→aM[1], and the process advances to a step S236. The step S235-2 sets ma'=M[1]→$B_{A1~An}$→aM[2], and the process advances to the step S236. The step S236 updates M[1]→$B_{A1~An}$→a, M[1]→$B_{A1~An}$→vector, and M[1]→$B_{A1~An}$→length to match ma, according to M[1]→$B_{Ai(1<=i<=n)}$→a{ma, ma'}, M[1]→$B_{Ai}$→vector={x'BAi, y'BAi, z'BAi}, and M[1]→$B_{Ai}$→length=length'_BAi.

A step S237 decides whether M[2]→A[ma]→b[j: 1<=j<=M[2]→A[ma]→nb]=M[2]→A[D→a]→bM[1], and the process advances to a step S238 if the decision result is YES. The step S238 adds M[2] to M[2] so that the directions of M[2]→M[M[2]→A[D→a]→b[1]]→vector and M[1]→$B_{A1~An}$→vector become the same, and reflects the change of M[2]→A[ma]→b[j] to M[2]→A[ma]→b[j]=M[1]→$B_{A1~An}$→b, according to 1<=kb<=M[2]→nb, 1<=ka<=M[2]→na, 1<=i<=n, M[1]→nb+M[2]→nb*(i−1)+kb=m, M[1]→na+M[2]→na*(i−1)+ka=m', M[1]→na+M[2]→na*(j−1)+ka=mj, M[1]→B[m]=M[2]→$B_{kb}$, M[1]→B[m]→vector=M[2]→$B_{kb}$→{x'i, y'i, z'i}, M[1]→A[m']=M[2]→$A_{ka}$, M[1]→A[mj]→b[j]=M[1]→$B_{Ai}$→b, and E[M[1]→ne]→B'[1~n]→eventFlag=Null.

A step S239 updates M[1]→na(nb) and stores M[1]→$B_{A1~An}$ to E, according to M[1]→na=M[1]→na+M[2]→na*n, M[1]→nb=M[1]→nb+M[2]→nb*n, and E[M[1]→ne]→B'[1~n]=M[1]→$B_{A1~An}$.

Finally, a step S240 updates M[1]→A→coordinate by M[1]→B→vector, and displays on the display screen 102a items of M[1]→A and M[1]→B, other than those set with the delete bit "Delete", with respect to the molecular data M[1], and the series of operations ends.

Figure 43:
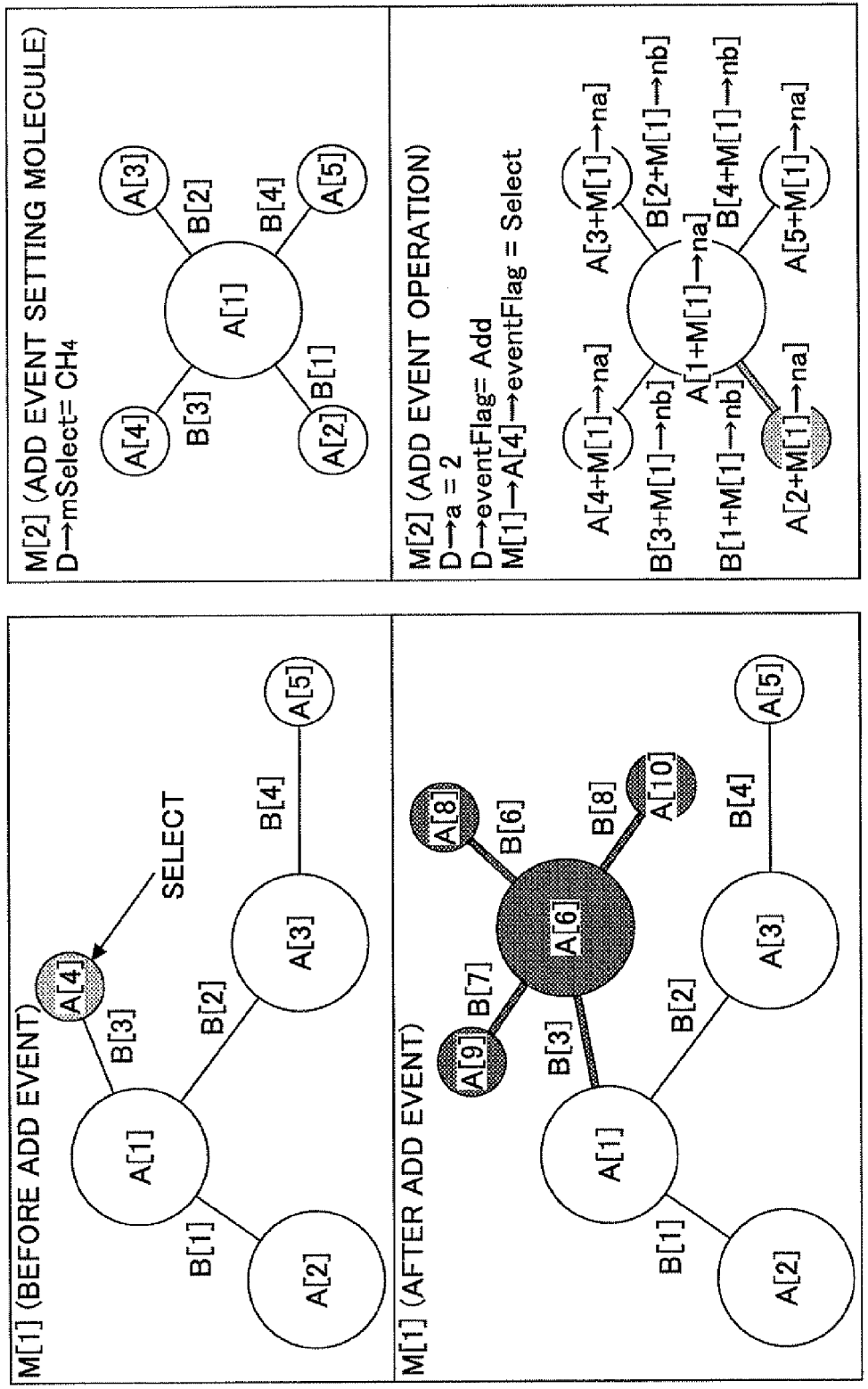
FIG. 43 is a diagram illustrating an example of a structural change by the add event for the formic acid (HCOOH)

FIG. 43 is a diagram illustrating an example of a structural change by the add event for the formic acid (HCOOH). In FIG. 43, the left side indicates the display state of the molecular structure of the molecular data M[1] on the display screen 102a before and after the add event, and the right side indicates the change in the structural data of the molecular data M[1] before and after the add event. FIG. 43 illustrates a case where a carbon atom AM[1] and hydrogen atoms AM[2]~AM[5] are added to the hydrogen atom AM[4]. In this case, the hydrogen atom linked to the carbon atom is substituted by the carbon atom of methane, and the structure as a whole is changed to a structure in which the methyl group is added to the original molecular structure. When the methane is changed to the methyl group, the hydrogen atom number to be deleted is registered in D→a.

Figure 44:
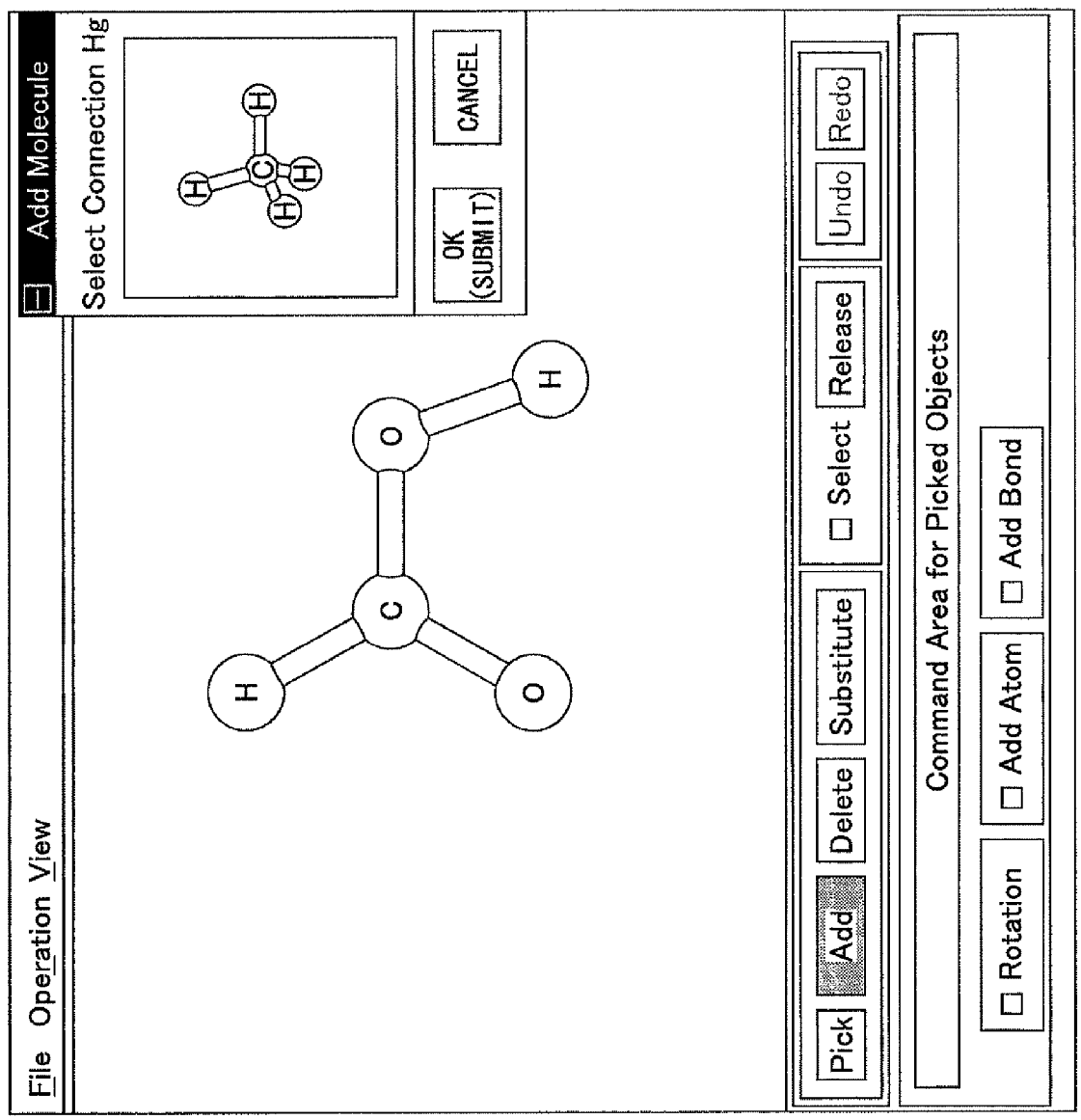
FIG. 44 is a diagram illustrating a display state of the molecular structure before the add event.
Figure 45:
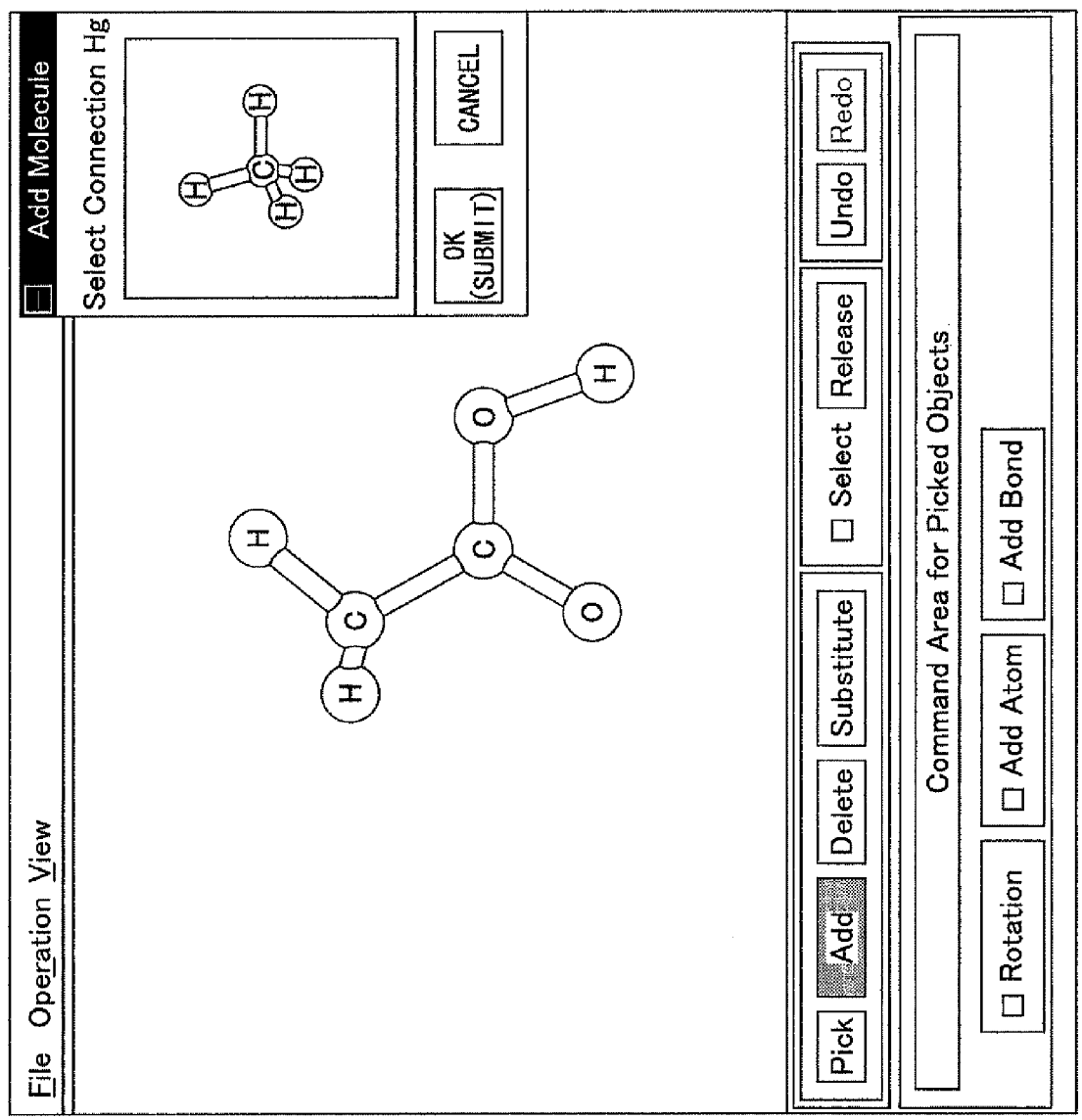
FIG. 45 is a diagram illustrating a display state of the molecular structure after the add event.

FIG. 44 is a diagram illustrating a display state of the molecular structure on the display screen 102a before the add event, and FIG. 45 is a diagram illustrating a display state of the molecular structure on the display screen 102a after the add event. The Undo operation and the Redo operation cannot be performed in the state before the add event illustrated in FIG. 44. On the other hand, the Undo operation can be performed and the Redo operation cannot be performed in the state after the add event illustrated in FIG. 45.

Figure 46:
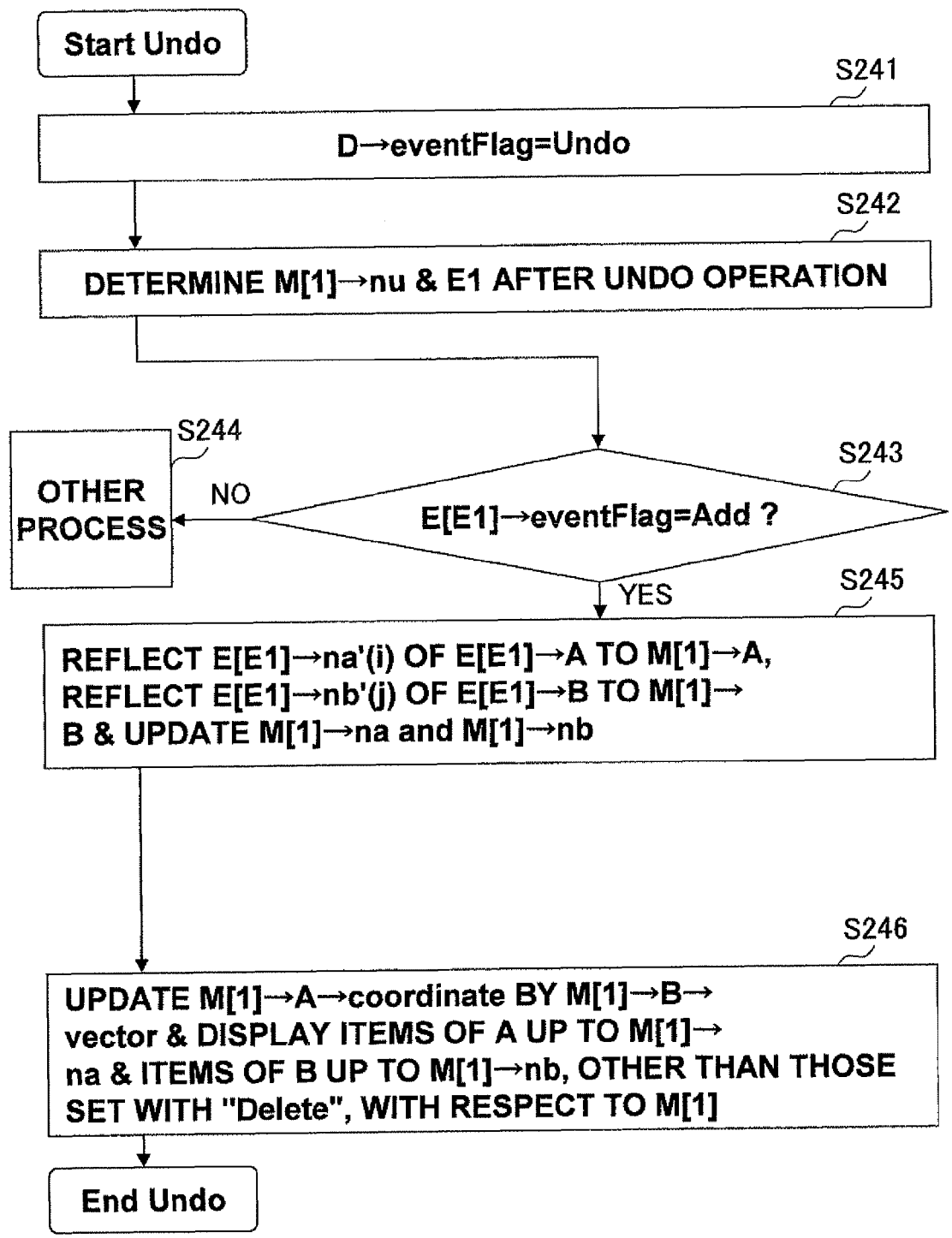
FIG. 46 is a flow chart for explaining a Redo operation of the add event.

FIG. 46 is a flow chart for explaining the Undo operation of the add event. When the Undo operation is started, a step S241 sets the event flag "eventFlag" of the auxiliary data to "Undo" according to D→eventFlag=Undo, based on a setting made by the user from the input part. A step S242 determines M[1]→nu and determines an event number E1 after the Undo operation, according to M[1]→nu=M[1]→nu+1 and E1=M[1]→ne−M[1]→nu+1. A step S243 decides whether E[E1]→eventFlag=Add, and the process advances to a step S244 which performs another process that is not directly related to the subject matter of the present invention if the decision result is NO. On the other hand, the process advances to a step S245 if the decision result in the step S243 is YES.

The step S245 reflects a number E[E1]→na'(i) of E[E1]→A to M[1]→A, reflects a number E[E1]→nb'(j) of E[E1]→B to M[1]→B, and updates M[1]→na and M[1]→nb, according to M[1]→A[E[E1]→A[1~i]→a]=E

[E1]→A[1~i], M[1]→B[E1]→B[1~j]→b]=E[E1]→B[1~j], M[1]→na=M[1]→na−E[E1]→na*E[E1]→na', and M[1]→nb=M[1]→nb−E[E1]→nb*E[E1]→nb'. Further, a step S246 updates M[1]→A→coordinate by M[1]→B→vector, and displays on the display screen 102a items of the atom A up to M[1]→na and items of the bond axis B up to M[1]→nb, other than those set with the delete bit "Delete", with respect to the molecular data M[1], and the Undo operation ends.

Figure 47:
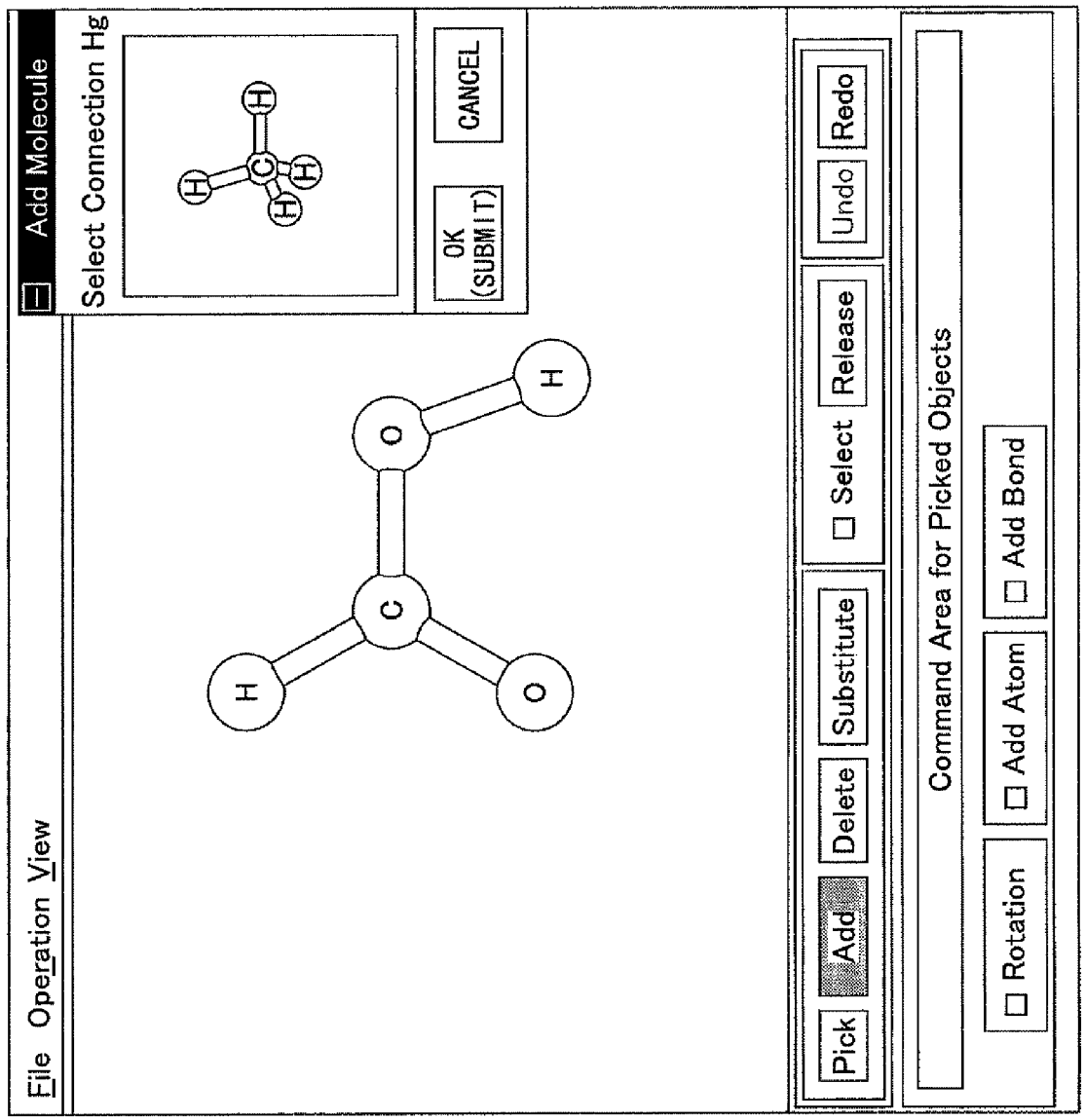
FIG. 47 is a diagram illustrating a display state of the molecular structure after the Undo operation.

FIG. 47 is a diagram illustrating a display state of the molecular structure on the display screen 102a after the Undo operation illustrated in FIG. 46. In the state after the Undo operation illustrated in FIG. 47, the Undo operation cannot be performed, but the Redo operation can be performed.

Figure 48:
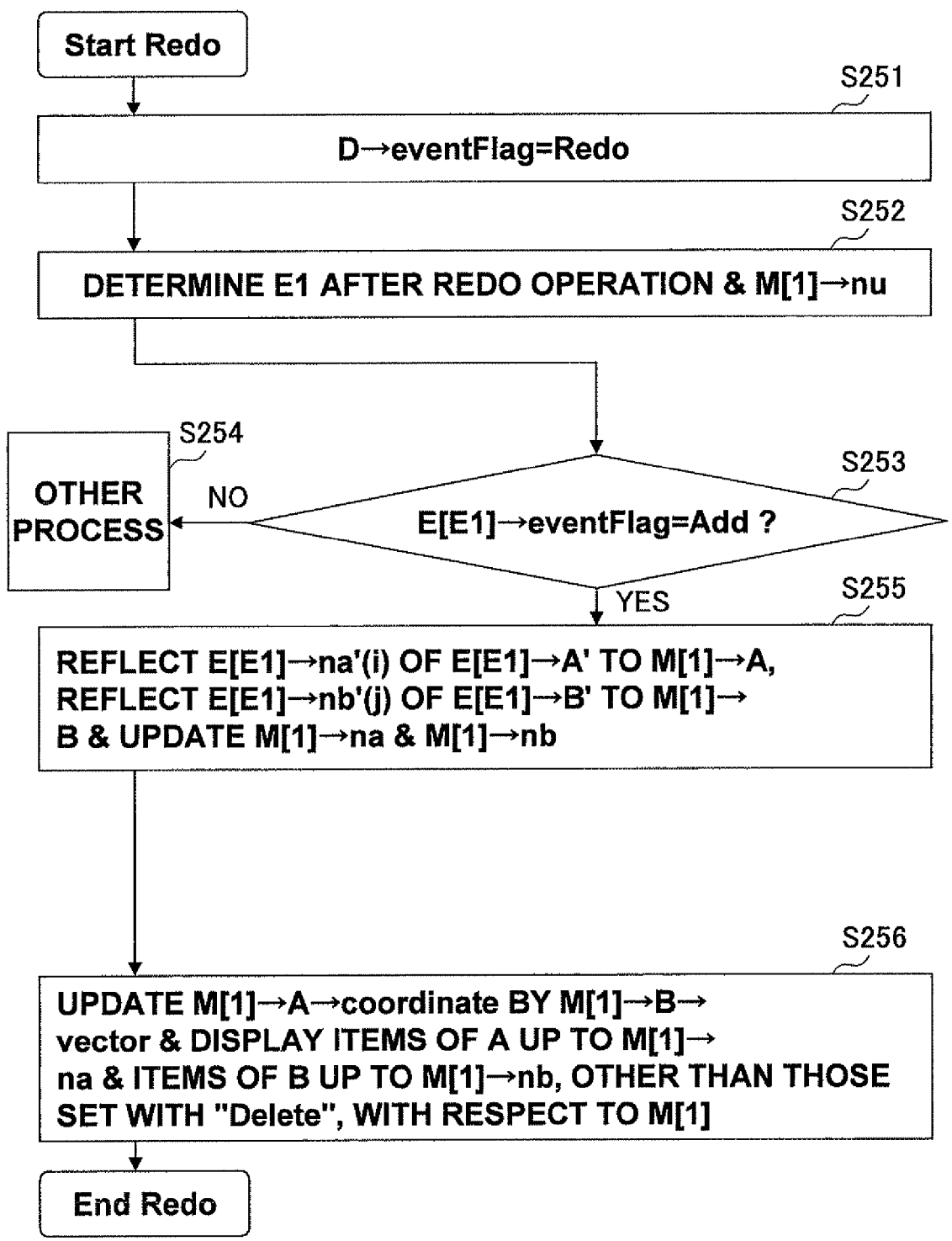
FIG. 48 is a flow chart for explaining a Redo operation of the add event.

FIG. 48 is a flow chart for explaining the Redo operation of the add event. When the Redo operation is started, a step S251 sets the event flag "eventFlag" of the auxiliary data to "Redo" according to D→eventFlag=Redo, based on a setting made by the user from the input part. A step S252 determines an event number E1 after the Redo operation and determines M[1]→nu, according to EM[1]=M[1]→ne−M[1]→nu+1 and M[1]→nu=M[1]→nu−1. A step S253 decides whether E[E1]→eventFlag=Add, and the process advances to a step S254 which performs another process that is not directly related to the subject matter of the present invention if the decision result is NO. On the other hand, the process advances to a step S255 if the decision result in the step S253 is YES.

The step S255 reflects a number E[E1]→na'(i) of E[E1]→A' to M[1]→A, reflects a number E[E1]→nb'(j) of E[E1]→B' to M[1]→B, and updates M[1]→na and M[1]→nb, according to M[1]→A[E1]→A[1~i]→a]=E[E1]→A[1~i], M[1]→B[E1]→B[1~j]→b]=E[E1]→B[1~j], M[1]→na=M[1]→na+E[E1]→na*E[E1]→na', and M[1]→nb=M[1]→nb+E[E1]→nb*E[E1]→nb'. Further, a step S256 updates M[1]→A→coordinate by M[1]→B→vector, and displays on the display screen 102a items of the atom A up to M[1]→na and items of the bond axis B up to M[1]→nb, other than those set with the delete bit "Delete", with respect to the molecular data M[1], and the Redo operation ends.

Figure 49:
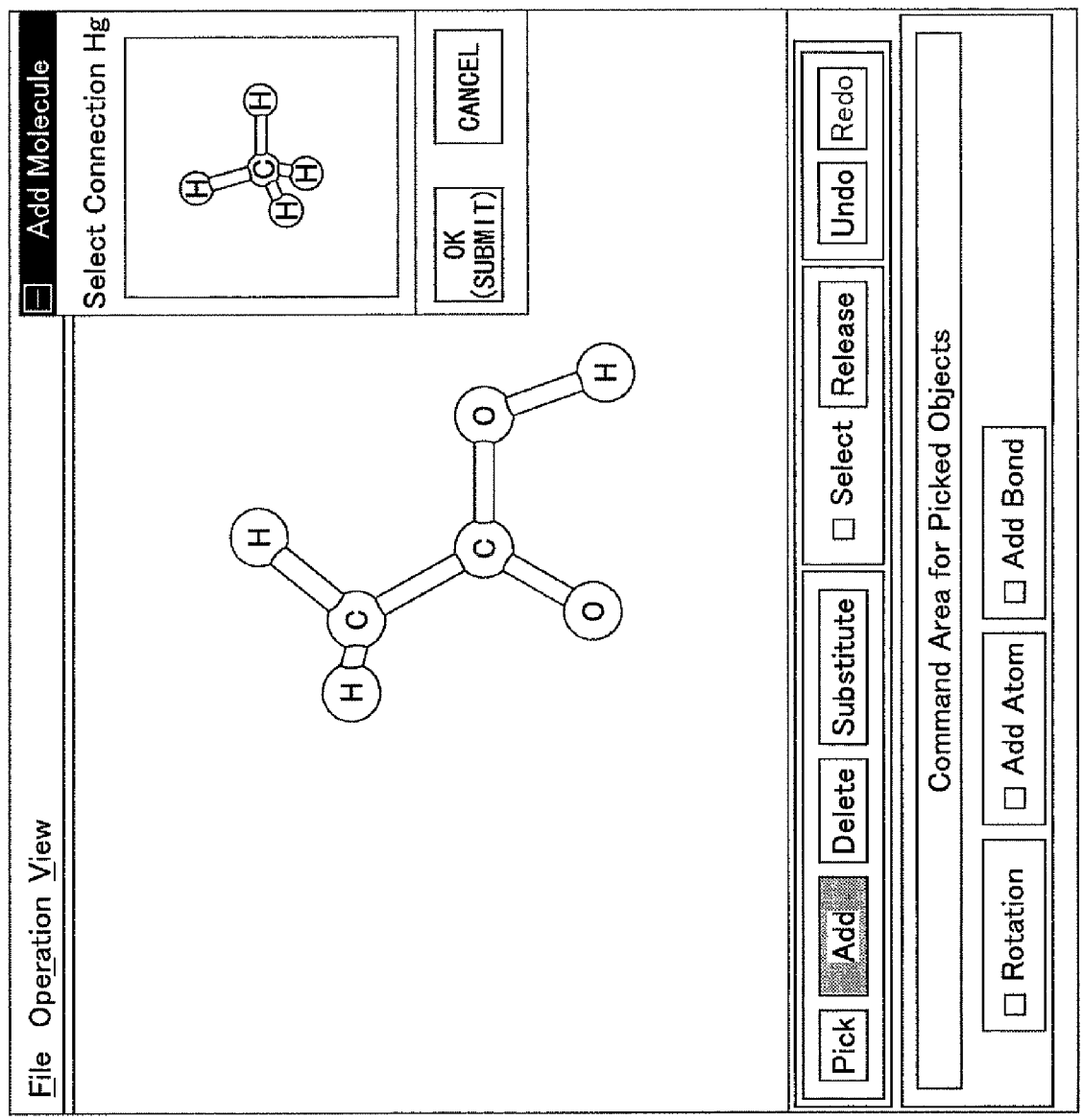
FIG. 49 is a diagram illustrating a display state of the molecular structure after the Redo operation.

FIG. 49 is a diagram illustrating a display state of the molecular structure on the display screen 102a after the Redo operation illustrated in FIG. 48. In FIG. 49, sub-windows are the same as those illustrated in FIG. 45. In the state after the Redo operation illustrated in FIG. 49, the Undo operation can be performed, but the Redo operation cannot be performed.

4. Relationship Among New Bond Event Operation, Undo Operation and Redo Operation:

With respect to the data structure illustrated in FIG. 1 that is constructed by the process illustrated in FIG. 13, the user selects two atom items by clicking the mouse 104, for example, in order to set a select bit "Select" in the event flag "eventFlag" of the selected atom items. This process is represented by M→A→eventFlag=Select. When the a new bond bit (or new bond axis adding bit) "NewBond" is set in the event flag "eventFlag" of the auxiliary data structure "D", a new bond event (or new bond axis adding event) is executed as illustrated in FIG. 50 in the case of the example illustrated in FIG. 2. FIG. 50 is a diagram illustrating an example of a data change by the new bond event for the formic acid (HCOOH). FIG. 50 illustrates a state before the new bond event, a user input, a new bond event operation, and a state after the new bond event. The event flag "eventFlag" of the auxiliary data structure "D" may be set in advance.

First, a present total event operation number is updated to M→ne=M→ne−M→nu+1, and the Undo event operation number is initialized to M→nu=0. When the total event operation number is updated, the subsequent event data is initialized to E[n>=M→ne]=Null, and the data for the new bond event is substituted into the present event by E[M→ne]→eventFlag=NewBond, . . . , etc. In the case of the new bond event, two atomic numbers are registered in place of the atom number and the bond axis in the atom number data and the bond axis data of the event data. After the substitution to the event data ends, the bond axis number of the molecular data is incremented by 1, and the bond axis data corresponding to a maximum bond axis number is added to the molecular data. Atomic information related to the bond axis data is set as the atomic information for which the select bit "Select" is set, and the length and the vector are set as the interatomic bond distance and the distance vector for which the select bit "Select" is set. Further, new bond axis information is added to the atomic data for which the select bit "Select" is set.

The new bond event operation is completed by redisplaying the molecular structure added with the new bond axis on the main window, after the data updating described above.

The Undo operation related to the new bond event illustrated in FIG. 50 is constructed as illustrated in FIG. 51. FIG. 51 is a diagram for explaining the constructing of the Undo operation related to the new bond event illustrated in FIG. 50. In other words, when an Undo bit is set in the event flag "eventFlag" of the auxiliary data structure "D", the Undo event operation number "nu" is first updated to M→nu=M→nu+1. The corresponding event number is set by the total event operation number and the Undo event operation number according to n=M→ne−M→nu+1, and the bond axis information is updated with respect to the atomic data corresponding to the atom number information included in the corresponding event data. More particularly, the bond axis number is decremented by 1, and a number corresponding to the bond axis number of the molecular data is deleted from the bond axis numbers included. In addition, the bond axis number of the present molecular data is decremented by 1. Finally, the Undo operation is completed by finally redisplaying only the items matching the atom number and the bond axis number of the molecular data on the main window.

The Redo operation related to the Undo operation illustrated in FIG. 51 is constructed as illustrated in FIG. 52. FIG. 52 is a diagram for explaining the constructing of the Redo operation related to the Undo operation illustrated in FIG. 51. In other words, when a Redo bit is set in the event flag "eventFlag" of the auxiliary data structure "D", the corresponding event number is first set by the total event operation number and the Undo event operation number according to n=M→ne−M→nu+1. Then, the Undo event operation number is updated to M→nu=M→nu−1, and the bond axis number of the present molecular data is incremented by 1. Moreover, the bond axis information is updated with respect to the atomic data corresponding to the atom number information included in the corresponding event data. More particularly, the bond axis number is incremented by 1, and the number corresponding to the bond axis number of the molecular data is added. The Redo operation is completed by finally redisplaying the molecular structure on the main window.

Figure 53:
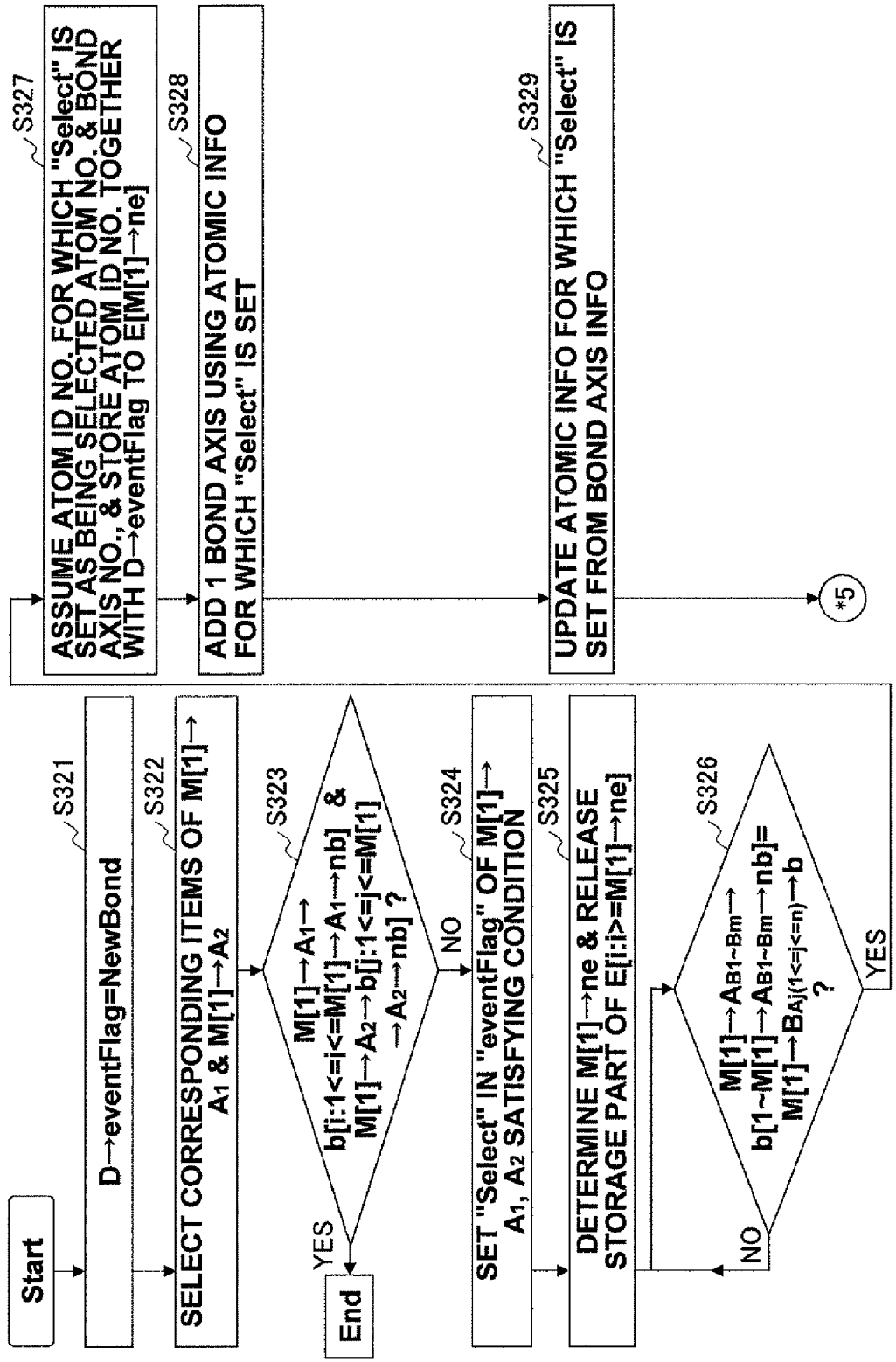
FIG. 53 is a flow chart for explaining a process of the new bond event.
Figure 54:
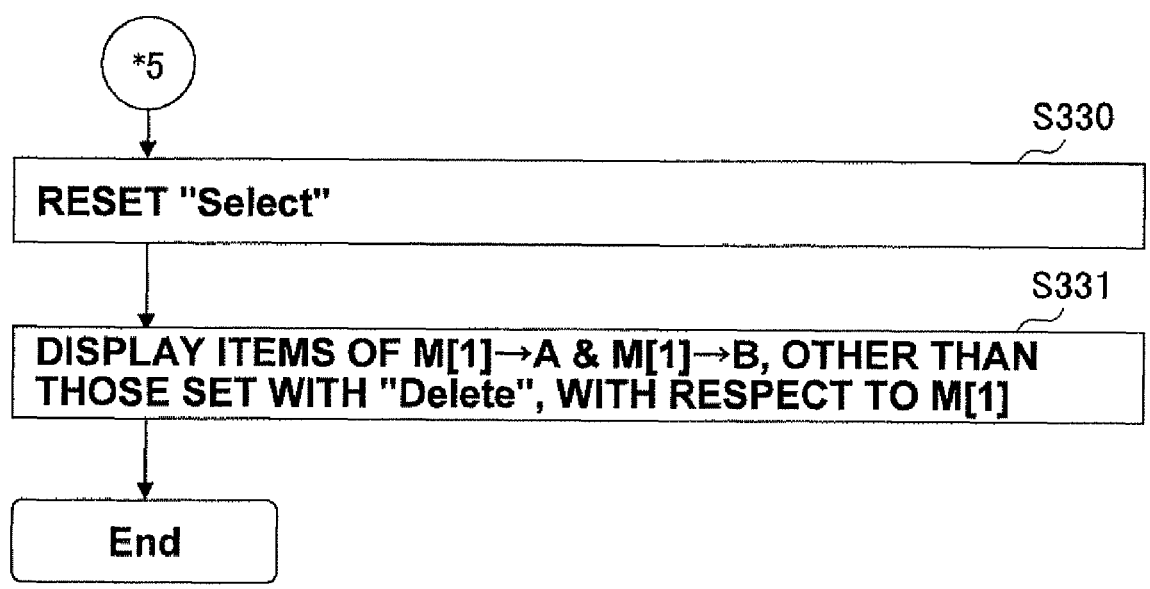
FIG. 54 is a flow chart for explaining the process of the new bond event.

FIGS. 53 and 54 are flow charts for explaining the process of the new bond event.

First, in FIG. 53, a step S321 sets D→eventFlag=NewBond, that is, sets the new bond bit "NewBond" in the event flag "eventFlag" of the auxiliary data structure "D", based on a setting made by the user from the input part. A step S322 selects corresponding items of M[1]→$A_1$ and M[1]→$A_2$, based on a selection made by the user from the input part. In this example, the atom items AM[3] and AM[2] are selected according to M[1]→AM[3]

and M[1]→AM[2]. Next, a step S323 decides whether M[1]→$A_1$→b[i:1<=i<=M[1]→$A_1$→nb] and M[1]→$A_2$→b[j:1<=j<=M[1]→$A_2$→nb], and the process ends if the decision result is YES. On the other hand, if the decision result in the step S323 is NO, the process advances to a step S324. The step S324 sets the select bit "Select" in the event flag "eventFlag" of M[1]→$A_1$, $A_2$ satisfying the condition according to M[1]→$A_1$→eventFlag=Select and M[1]→$A_2$→eventFlag=Select. A step S325 determines M[1]→ne according to M[1]→ne=M[1]→ne−M[1]→nu+1, M[1]→nu=0, and E[n]=Null(M[1]→ne<=n<=MaxEvent), and releases the storage part of E[i:i>=M[1]→ne]. In other words, the total event operation number ne of M[1] is determined, and the storage part is released with respect to the M[1]→(ne)th and subsequent event data. A step S326 decides whether M[1]→$A_{B1\sim Bm}$→b[1~M[1]→$A_{B1\sim Bm}$→nb]=M[1]→$B_{Aj(1<=j<=n)}$→b, and the process advances to a step S327 if the decision result is YES. The step S327 assumes the atom identification number for which the select bit "Select" is set as being the selected atom number and bond axis number, and stores the atom identification number together with D→eventFlag to E[M[1]→ne], according to E[M[1]→ne]→eventFlag=D→eventFlag, E[M[1]→ne]→na'=M[1]→$A_1$→a, and E[M[1]→ne]→nb'=M[1]→$A_s$→a. A step S328 adds one bond axis using the atomic information for which the select bit "Select" is set, according to M[1]→nb=M[1]→nb+1, M[1]→B[M[1]→nb]→b=M[1]→nb, M[1]→B[M[1]→nb]→aM[1]=M[1]→$A_1$→a, M[1]→B[M[1]→nb]→aM[2]=M[1]→$A_2$→a, M[1]→B[M[1]→nb]→eventFlag=Null, M[1]→B[M[1]→nb]→vector=M[1]→$A_1$→coordinate−M[1]→B[M[1]→nb]→length=sqrt($B^2$), and (B=M[1]→B[M[1]→nb]→vector). A step S329 updates the atomic information for which the select bit "Select" is set from the bond axis information, according to M[1]→$A_1$→nb=M[1]→$A_1$→nb+1, M[1]→$A_2$→nb=M[1]→$A_2$→nb+1, M[1]→$A_1$→b[M[1]→$A_1$→nb]=M[1]→nb, and M[1]→$A_2$→b[M[1]→$A_2$→nb]=M[1]→nb. After the step S329, the process advances to a step S330 illustrated in FIG. 54.

In FIG. 54, the step S330 resets the select bit "Select", according to M[1]→$A_1$→eventFlag=Null and M[1]→$A_2$→eventFlag=Null. Finally, a step S331 displays on the display screen 102a items of M[1]→A and M[1]→B, other than those set with the delete bit "Delete", with respect to the molecular data M[1], and the series of operations ends.

Figure 55:
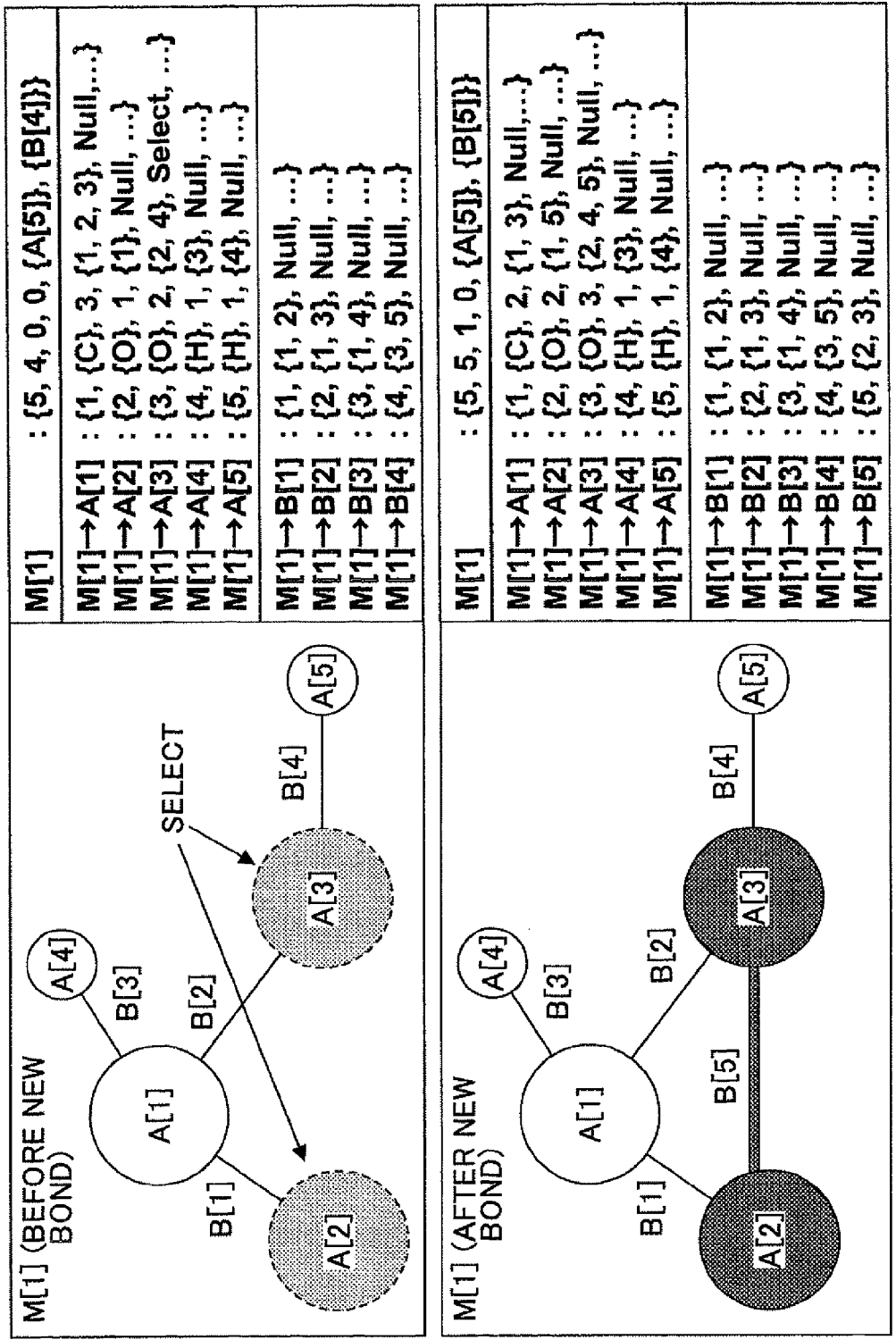
FIG. 55 is a diagram illustrating an example of a structural change by the new bond event for the formic acid (HCOOH)

FIG. 55 is a diagram illustrating an example of a structural change by the new bond event for the formic acid (HCOOH). In FIG. 55, the left side indicates the display state of the molecular structure of the molecular data M[1] on the display screen 102a before and after the new bond event, and the right side indicates the change in the structural data of the molecular data M[1] before and after the new bond event. FIG. 55 illustrates a case where a new bond axis BM[5] is added.

Figure 56:
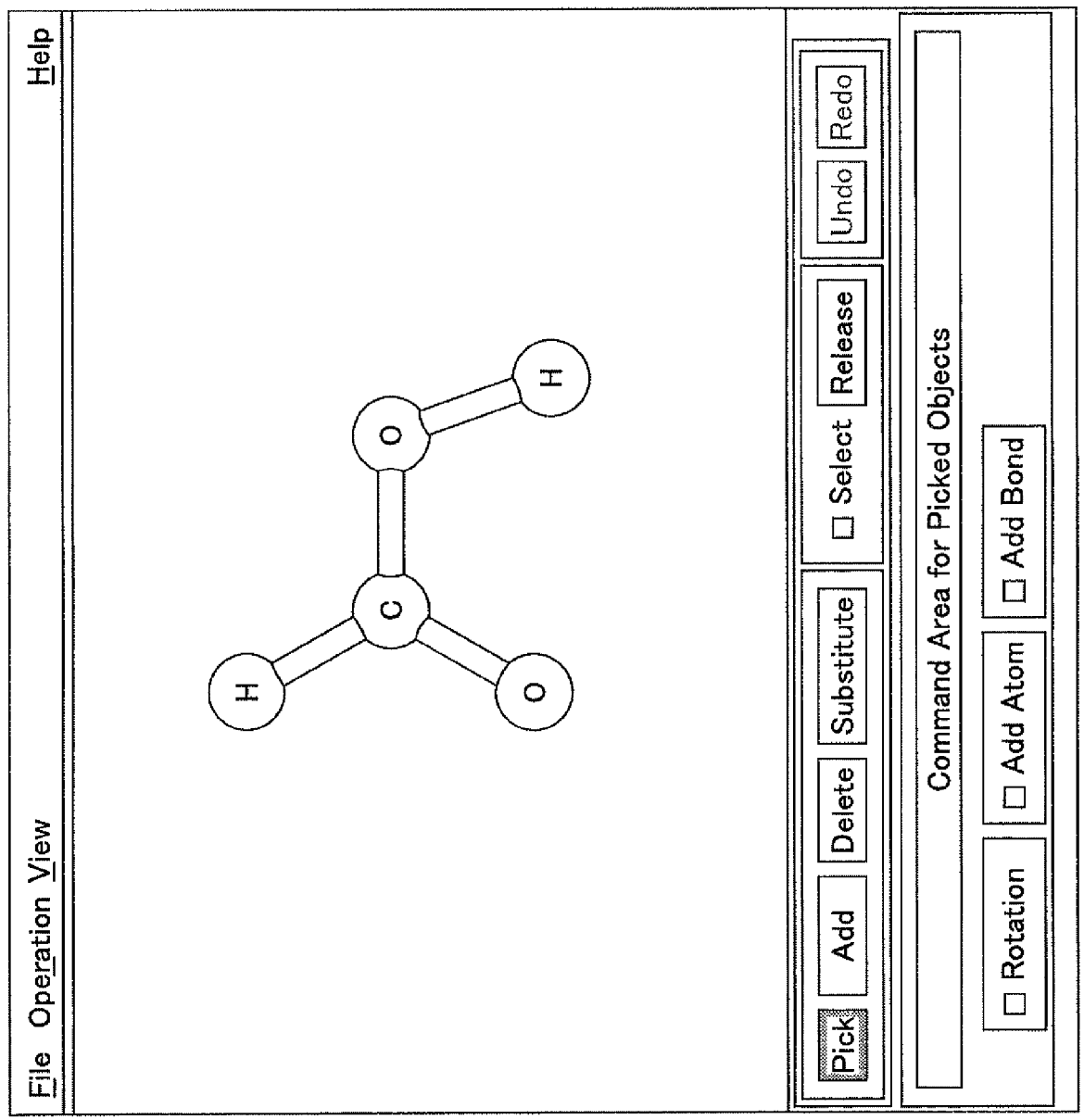
FIG. 56 is a diagram illustrating a display state of the molecular structure before the new bond event.
Figure 57:
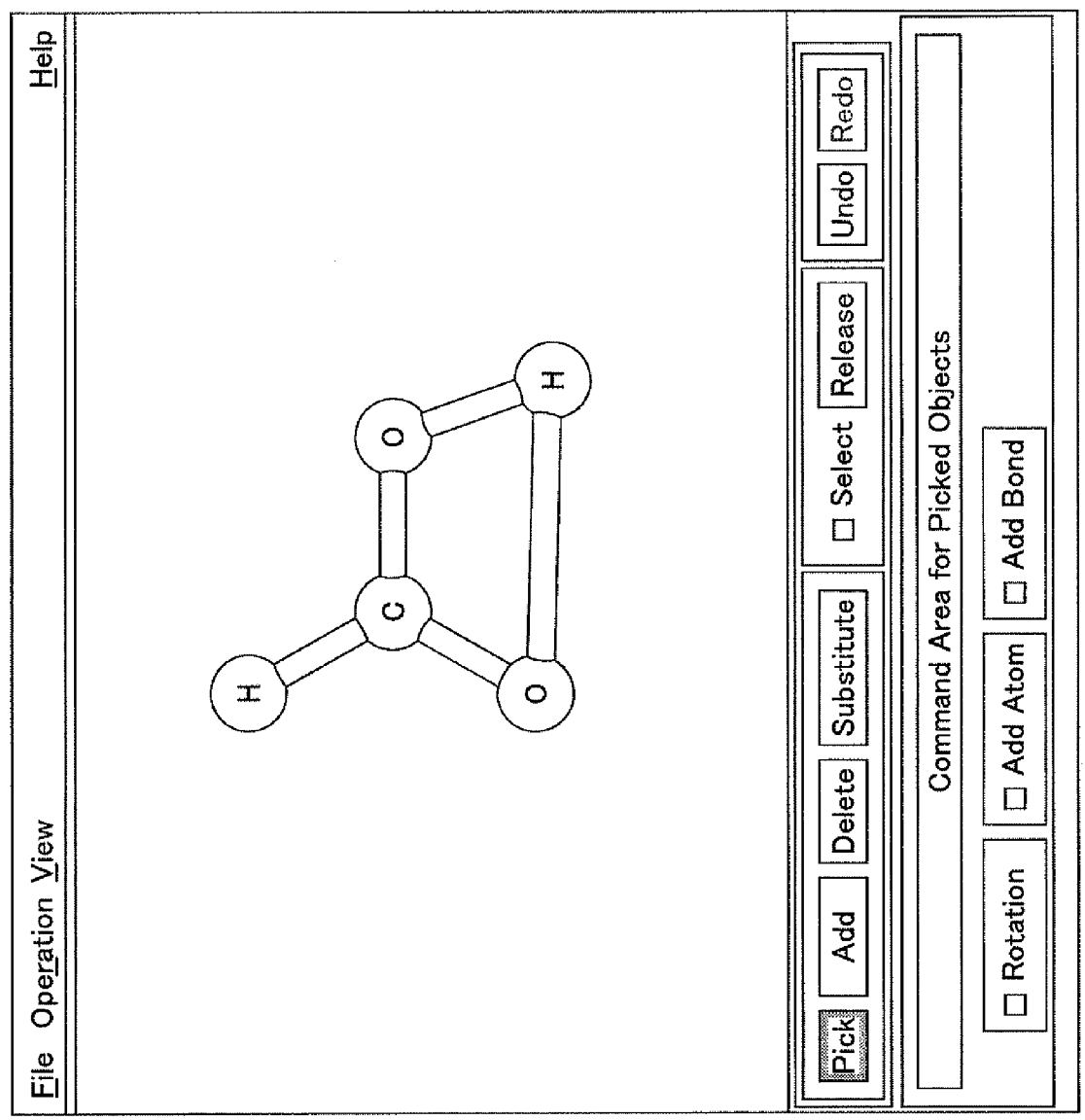
FIG. 57 is a diagram illustrating a display state of the molecular structure after the new bond event.

FIG. 56 is a diagram illustrating a display state of the molecular structure on the display screen 102a before the new bond event, and FIG. 57 is a diagram illustrating a display state of the molecular structure on the display screen 102a after the new bond event. The Undo operation and the Redo operation cannot be performed in the state before the new bond event illustrated in FIG. 56. On the other hand, the Undo operation can be performed and the Redo operation cannot be performed in the state after the new bond event illustrated in FIG. 57.

Figure 58:
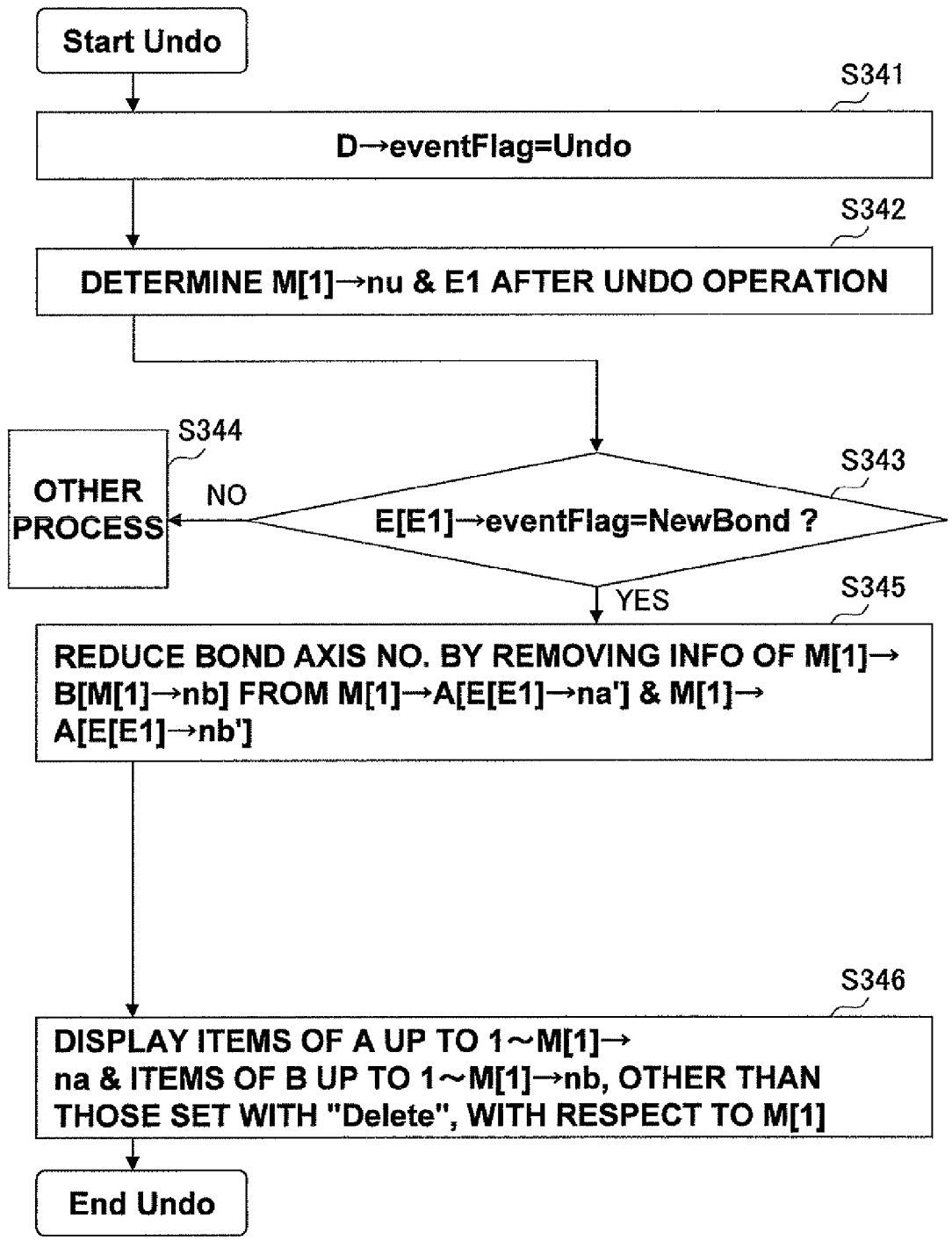
FIG. 58 is a flow chart for explaining an Undo operation of the new bond event.

FIG. 58 is a flow chart for explaining the Undo operation of the new bond event. When the Undo operation is started, a step S341 sets the event flag "eventFlag" of the auxiliary data to "Undo" according to D→eventFlag=Undo, based on a setting made by the user from the input part. A step S342 determines M[1]→nu and determines an event number E1 after the Undo operation, according to M[1]→nu=M[1]→nu+1 and E1=M[1]→ne−M[1]→nu+1. A step S343 decides whether E[E1]→eventFlag=NewBond, and the process advances to a step S344 which performs another process that is not directly related to the subject matter of the present invention if the decision result is NO. On the other hand, the process advances to a step S345 if the decision result in the step S343 is YES.

The step S345 reduces the bond axis number by removing information of M[1]→B[M[1]→nb] from M[1]→A[E[E1]→na'] and M[1]→A[E[E1]→nb'], according to M[1]→A[E[E1]→na']→nb−1, M[1]→A[E[E1]→nb']→nb−1, and M[1]→nb=M[1]→nb−1. Further, a step S346 displays on the display screen 102a items of the atom A up to 1~M[1]→na and items of the bond axis B up to 1~M[1]→nb, other than those set with the delete bit "Delete", with respect to the molecular data M[1], and the Undo operation ends.

Figure 59:
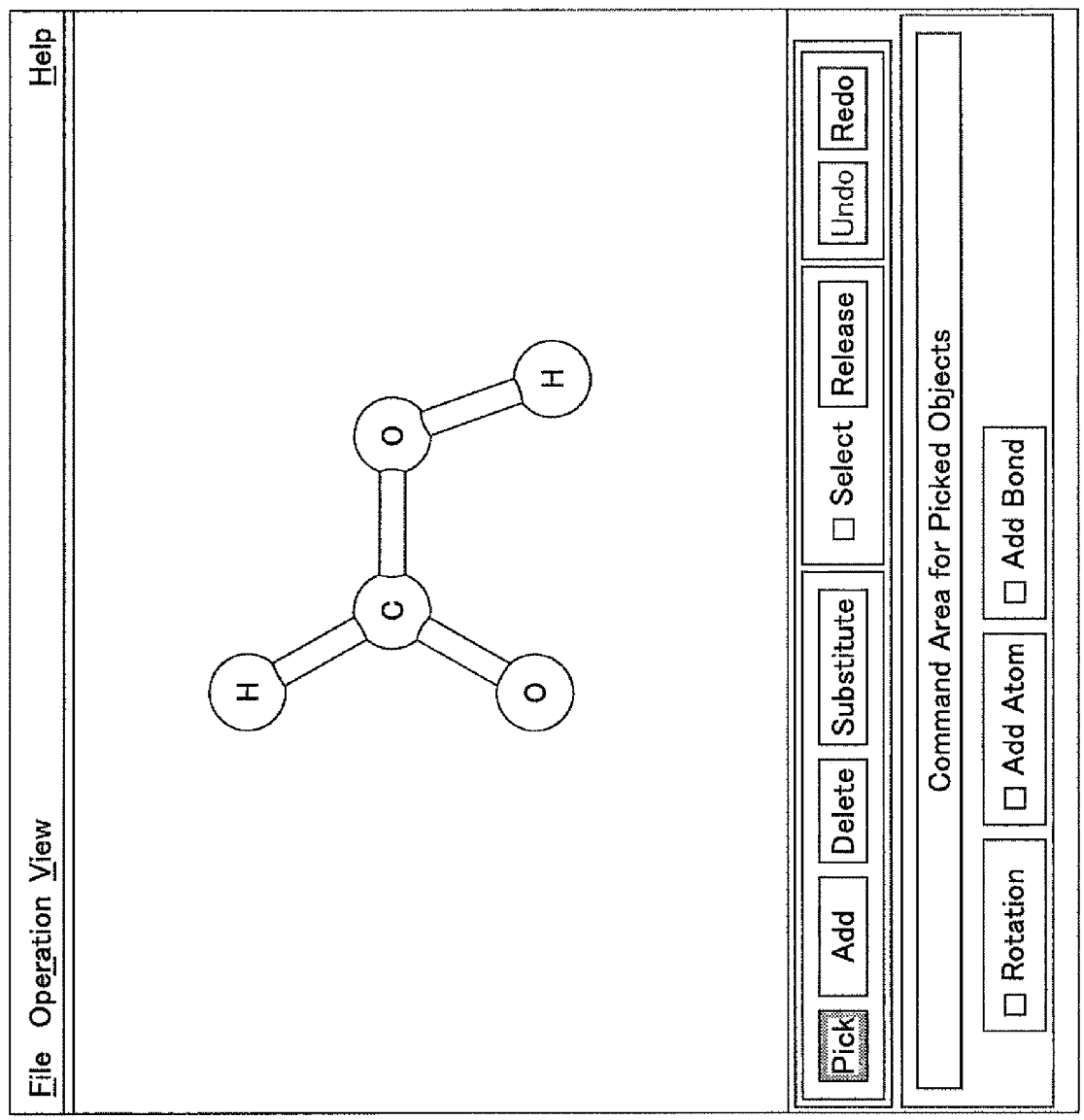
FIG. 59 is a diagram illustrating a display state of the molecular structure after the Undo operation.

FIG. 59 is a diagram illustrating a display state of the molecular structure on the display screen 102a after the Undo operation illustrated in FIG. 58. In the state after the Undo operation illustrated in FIG. 59, the Undo operation cannot be performed, but the Redo operation can be performed.

Figure 60:
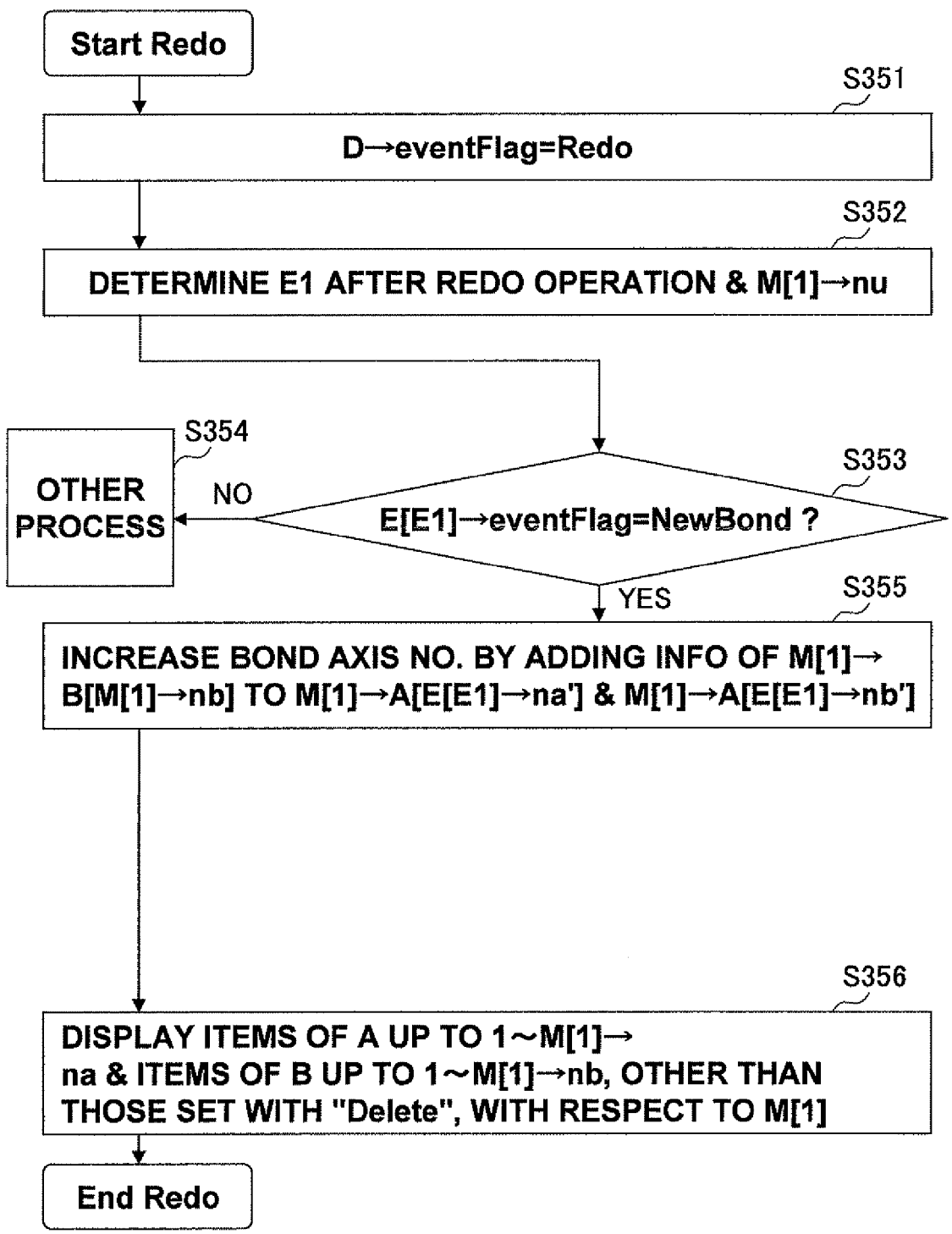
FIG. 60 is a flow chart for explaining a Redo operation of the new bond event.

FIG. 60 is a flow chart for explaining the Redo operation of the new bond event. When the Redo operation is started, a step S351 sets the event flag "eventFlag" of the auxiliary data to "Redo" according to D→eventFlag=Redo, based on a setting made by the user from the input part. A step S352 determines an event number E1 after the Redo operation and determines M[1]→nu, according to EM[1]=M[1]→ne−M[1]→nu+1 and M[1]→nu=M[1]→nu−1. A step S353 decides whether E[E1]→eventFlag=NewBond, and the process advances to a step S354 which performs another process that is not directly related to the subject matter of the present invention if the decision result is NO. On the other hand, the process advances to a step S355 if the decision result in the step S353 is YES.

The step S355 increases the bond axis number by adding the information of M[1]→B[M[1]→nb] to M[1]→A[E[E1]→na'] and M[1]→A[E[E1]→nb'], according to M[1]→nb=M[1]→nb+1, M[1]→A[E[E1]→na']→nb+1, and M[1]→A[E[E1]→nb']→nb+1. Further, a step S356 displays on the display screen 102a items of the atom A up to 1~M[1]→na and items of the bond axis B up to 1~M[1]→nb, other than those set with the delete bit "Delete", with respect to the molecular data M[1], and the Redo operation ends.

Figure 61:
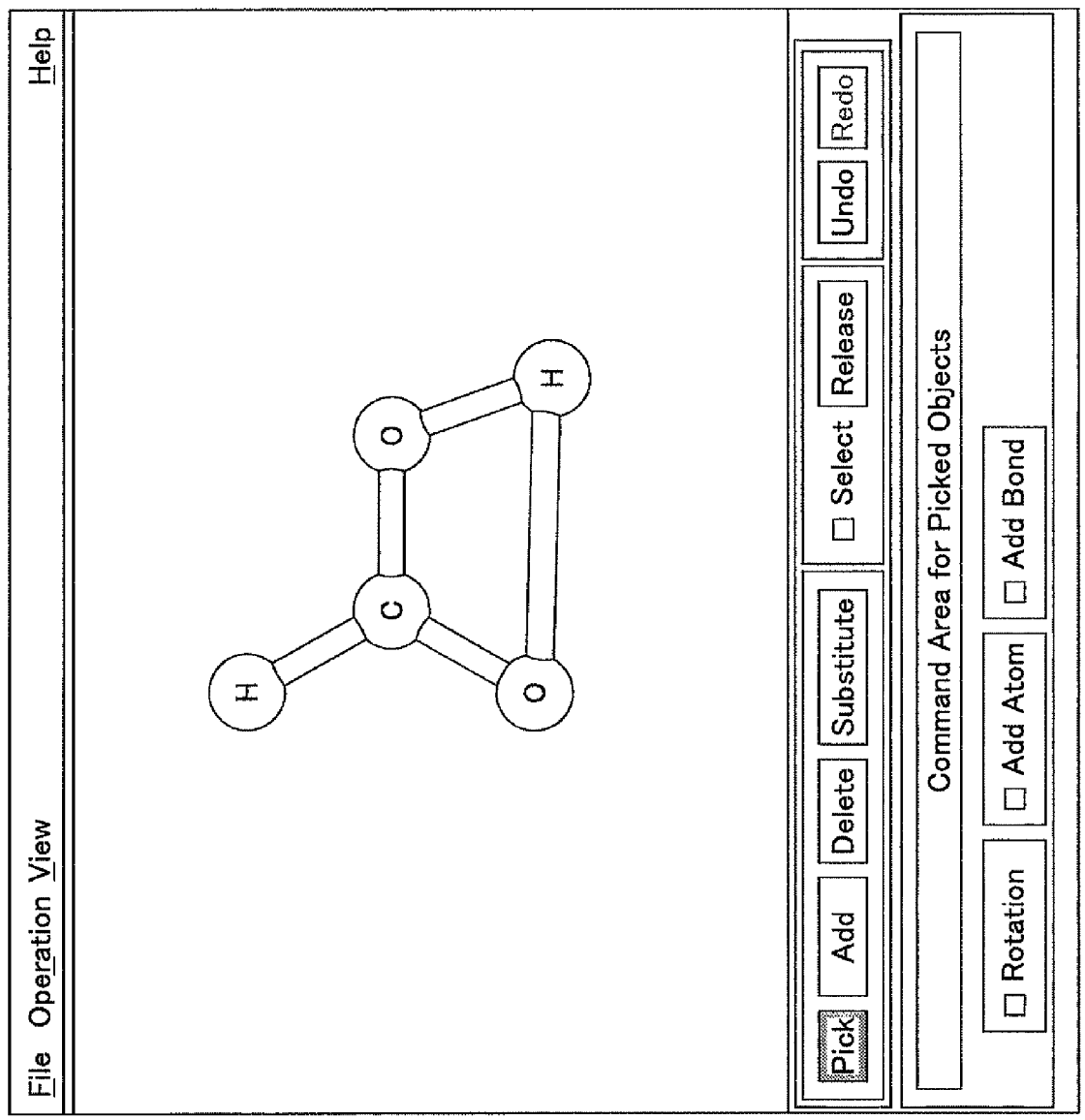
FIG. 61 is a diagram illustrating a display state of the molecular structure after the Redo operation.

FIG. 61 is a diagram illustrating a display state of the molecular structure on the display screen 102a after the Redo operation illustrated in FIG. 60. In the state after the Redo operation illustrated in FIG. 61, the Undo operation can be performed, but the Redo operation cannot be performed.

5. Relationship Among New Atom Event Operation, Undo Operation and Redo Operation:

With respect to the data structure illustrated in FIG. 1 that is constructed by the process illustrated in FIG. 13, the user selects two atom items by clicking the mouse 104, for example, in order to set a select bit "Select" in the event flag "eventFlag" of the selected atom items. This process is represented by M→A→eventFlag=Select. When the a new atom bit (or new atom adding bit) "NewAtom" is set in the event flag "eventFlag" of the auxiliary data structure "D", a new atom event (or new atom adding event) is executed as illustrated in FIG. 62 in the case of the example illustrated in FIG. 2. FIG. 62 is a diagram illustrating an example of a data change by the new atom event for the formic acid (HCOOH). FIG. 62 illustrates a state before the new atom event, a user input, a new atom event operation, and a state after the new atom event. The event flag "eventFlag" of the auxiliary data structure "D" may be set in advance. FIG. 62 illustrates a case where HCOOH changes to $CH_3COOH$ by the new atom event.

First, a present total event operation number is updated to M→ne=M→ne-M→nu+1, and the Undo event operation number is initialized to M→nu=0. When the total event operation number is updated, the subsequent event data is initialized to E[n>=M→ne]=Null, and the data for the new atom event is substituted into the present event by E[M→ne]→eventFlag=NewAtom, ..., etc. In the case of the new atom event, the atom number information of the atom for which the select bit "Select" is set is registered in the atom number of the event data. After the substitution to the event data ends, the atom number and the bond axis number of the molecular data are updated by incrementing by 1, and the atomic data and the bond axis data corresponding to a maximum atom number and a maximum bond axis number are added to the molecular data. Distance information related to the new bond axis data may be specified to a constant by restricting the atomic data that is to be added to only the hydrogen atom, for example. Further, measures may be taken with respect to the vector information so as to prevent overlap with other bond axes. The atomic data that is added may be changed to an arbitrary atomic data by performing a substitute event operation after the adding of the atomic data.

The new atom event operation is completed by redisplaying the molecular structure added with the new atom on the main window, after the data updating described above.

The Undo operation related to the new atom event illustrated in FIG. 62 is constructed as illustrated in FIG. 63. FIG. 63 is a diagram for explaining the constructing of the Undo operation related to the new atom event illustrated in FIG. 62. In other words, when an Undo bit is set in the event flag "eventFlag" of the auxiliary data structure "D", the Undo event operation number "nu" is first updated to M→nu=M→nu+1. The corresponding event number is set by the total event operation number and the Undo event operation number according to n=M→ne-M→nu+1, and the bond axis information is updated with respect to the atomic data corresponding to the atom number information included in the corresponding event data. More particularly, the bond axis number is decremented by 1. In addition, the atom number and the bond axis number in the present molecular data are decremented by 1. Finally, the Undo operation is completed by finally redisplaying only the items matching the atom number and the bond axis number of the molecular data on the main window.

The Redo operation related to the Undo operation illustrated in FIG. 63 is constructed as illustrated in FIG. 64. FIG. 64 is a diagram for explaining the constructing of the Redo operation related to the Undo operation illustrated in FIG. 63. In other words, when a Redo bit is set in the event flag "eventFlag" of the auxiliary data structure "D", the corresponding event number is first set by the total event operation number and the Undo event operation number according to n=M→ne-M→nu+1. Then, the Undo event operation number is updated to M→nu=M→nu-1, and the atom number and the bond axis number of the present molecular data are incremented by 1. Moreover, the bond axis information is updated with respect to the atomic data corresponding to the atom number information included in the corresponding event data. More particularly, the bond axis number is incremented by 1. The Redo operation is completed by finally redisplaying the molecular structure on the main window.

Figure 65:
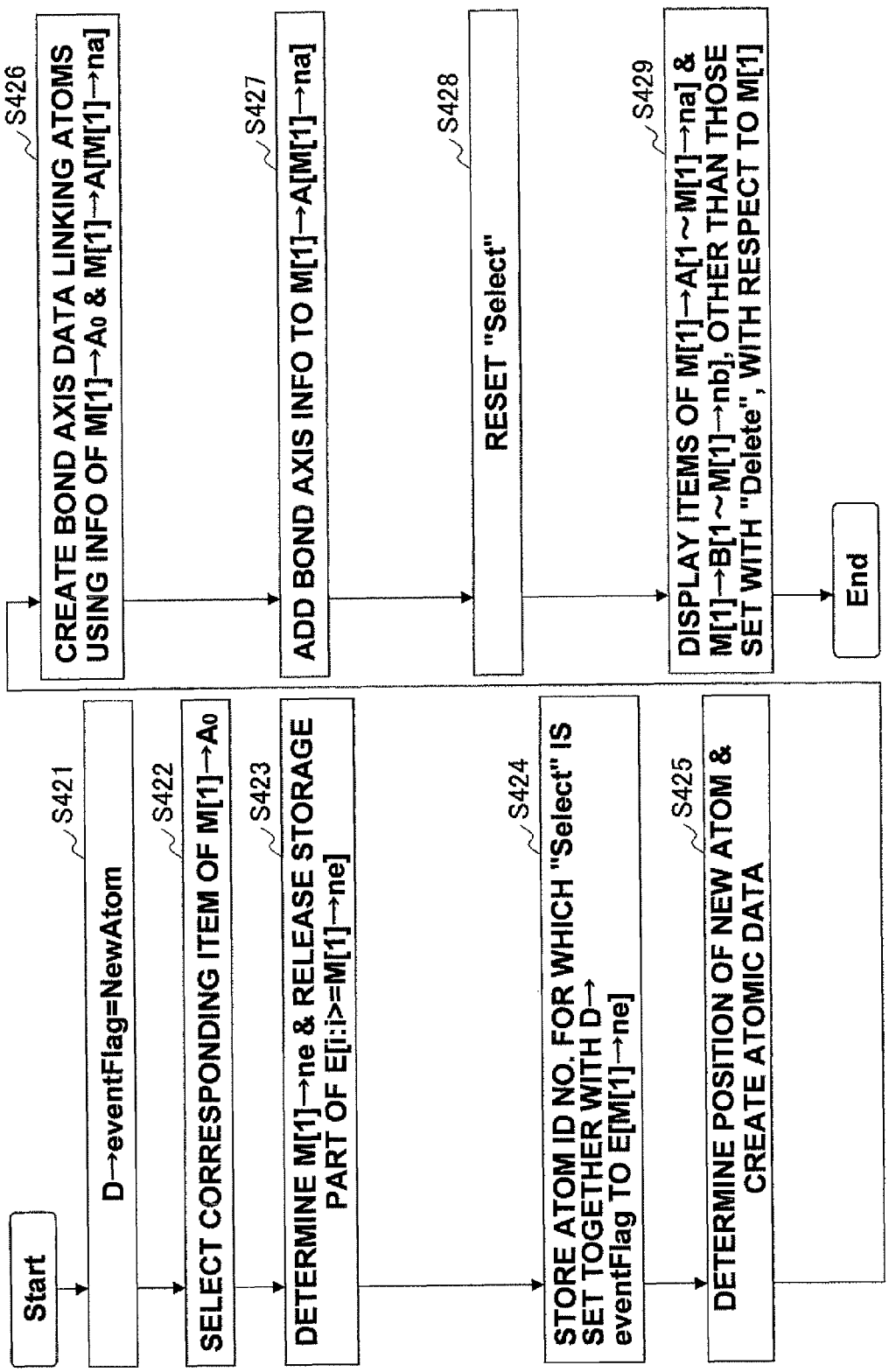
FIG. 65 is a flow chart for explaining a process of the new atom event.

FIG. 65 is a flow chart for explaining the process of the new atom event.

First, in FIG. 65, a step S421 sets D→eventFlag=NewAtom, that is, sets the new atom bit "NewAtom" in the event flag "eventFlag" of the auxiliary data structure "D", based on a setting made by the user from the input part. A step S422 selects a corresponding item of $M[1] \rightarrow A_0$ according to $M[1] \rightarrow A_0$eventFlag=Select, based on a selection made by the user from the input part. In this example, the atom item AM[3] is selected according to M[1]→AM[3]. Next, a step S423 determines M[1]→ne according to M[1]→ne=M[1]→ne-M[1]→nu+1, M[1]→nu=0, and E[n]=Null(M[1]→ne<=n<=MaxEvent), and releases the storage part of E[i:i>=M[1]→ne]. In other words, the total event operation number ne of M[1] is determined, and the storage part is released with respect to the M[1]→(ne)th and subsequent event data. A step S424 stores the atom identification number for which the select bit "Select" is set together with D→eventFlag to E[M[1]→ne], according to E[M[1]→ne]→eventFlag=D→eventFlag, and $E[M[1] \rightarrow ne] \rightarrow na'=M[1] \rightarrow A_0 \rightarrow a$. A step S425 determines the position of the new atom and creates the atomic data, according to M[1]→na=M[1]→na+1, M[1]→A[M[1]→na]→a=M[1]→a, M[1]→A[M[1]→na]→eventFlag=Null, and M[1]→A[M[1]→na]→coordinate={x, y, z}. A step S426 creates the bond axis data linking the atoms using information of $M[1] \rightarrow A_0$ and M[1]→A[M[1]→na], according to M[1]→nb=M[1]→nb+1, M[1]→B[M[1]→nb]b=M[1]→nb, M[1]→B[M[1]→nb]→eventFlag=Null, M[1]→B[M[1]→nb]→aM[1]=M[1]→$A_0$→a, M[1]→B[M[1]→nb]aM[2]=M[1]→na, M[1]→B[M[1]→nb]→vector=M[1]→A[M[1]→na]→coordinate-M[1]→$A_0$→coordinate, and M[1]→B[M[1]→nb]→length=sqrt((M[1]→B[M[1]→nb]→vector)**2). A step S427 adds the bond axis information to M[1]→A[M[1]→na], according to M[1]→A[M[1]→na]+1 and M[1]→A[M[1]→na]→bj=M[1]→nb. A step S428 resets the select bit "Select", according to M[1]→$A_1$→eventFlag=Null and M[1]→$A_2$→eventFlag=Null. Finally, a step S429 displays on the display screen 102a items of M[1]→A[1~M[1]→na] and M[1]→B[1~M[1]→nb], other than those set with the delete bit "Delete", with respect to the molecular data M[1], and the series of operations ends.

FIG. 66 is a diagram illustrating an example of a structural change by the new atom event for the formic acid (HCOOH). In FIG. 66, the left side indicates the display state of the molecular structure of the molecular data M[1] on the display screen 102a before and after the new atom event, and the right side indicates the change in the structural data of the molecular data M[1] before and after the new atom event. FIG. 66 illustrates a case where a new atom AM[6] is added.

Figure 67:
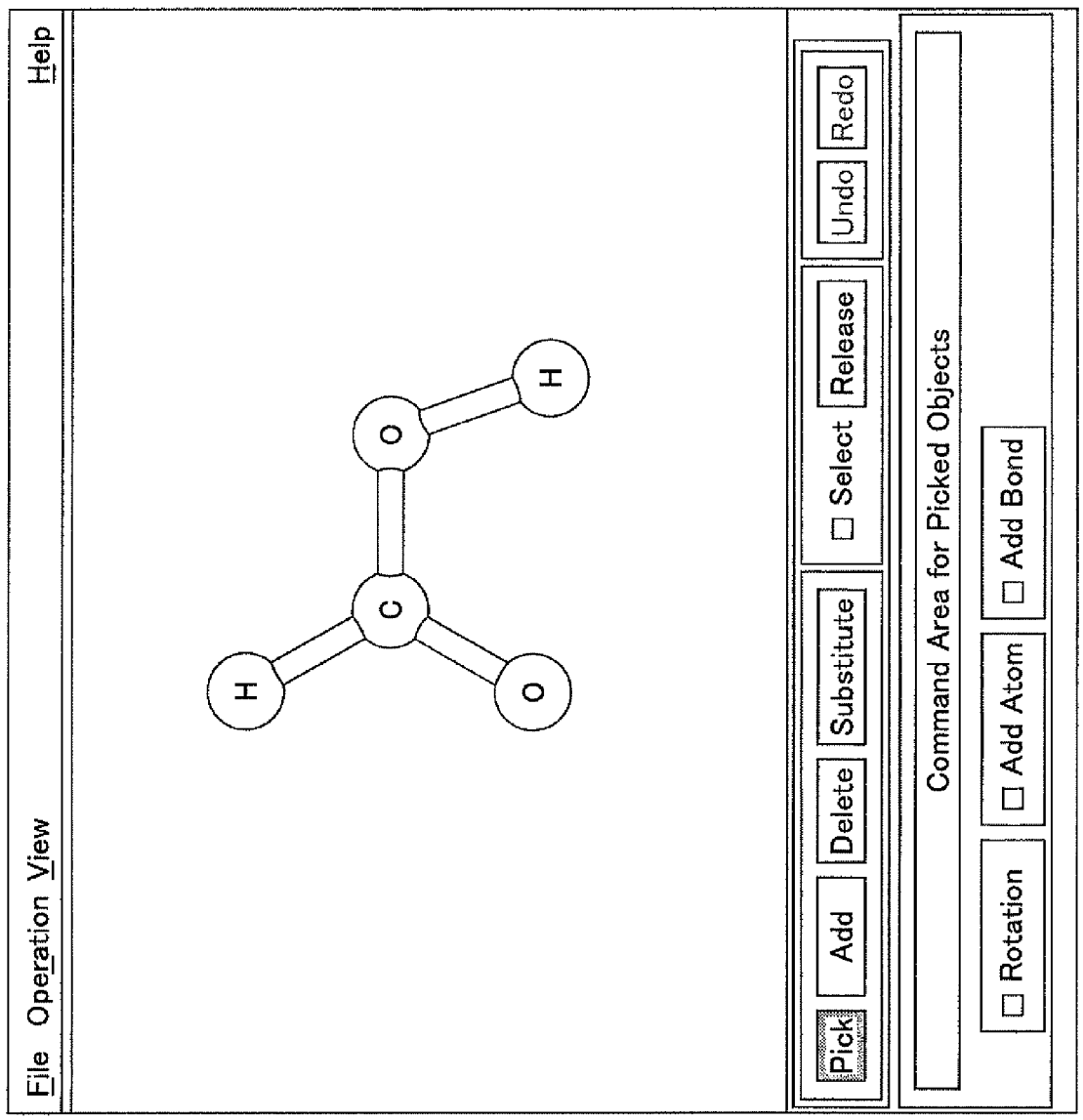
FIG. 67 is a diagram illustrating a display state of the molecular structure before the new atom event.
Figure 68:
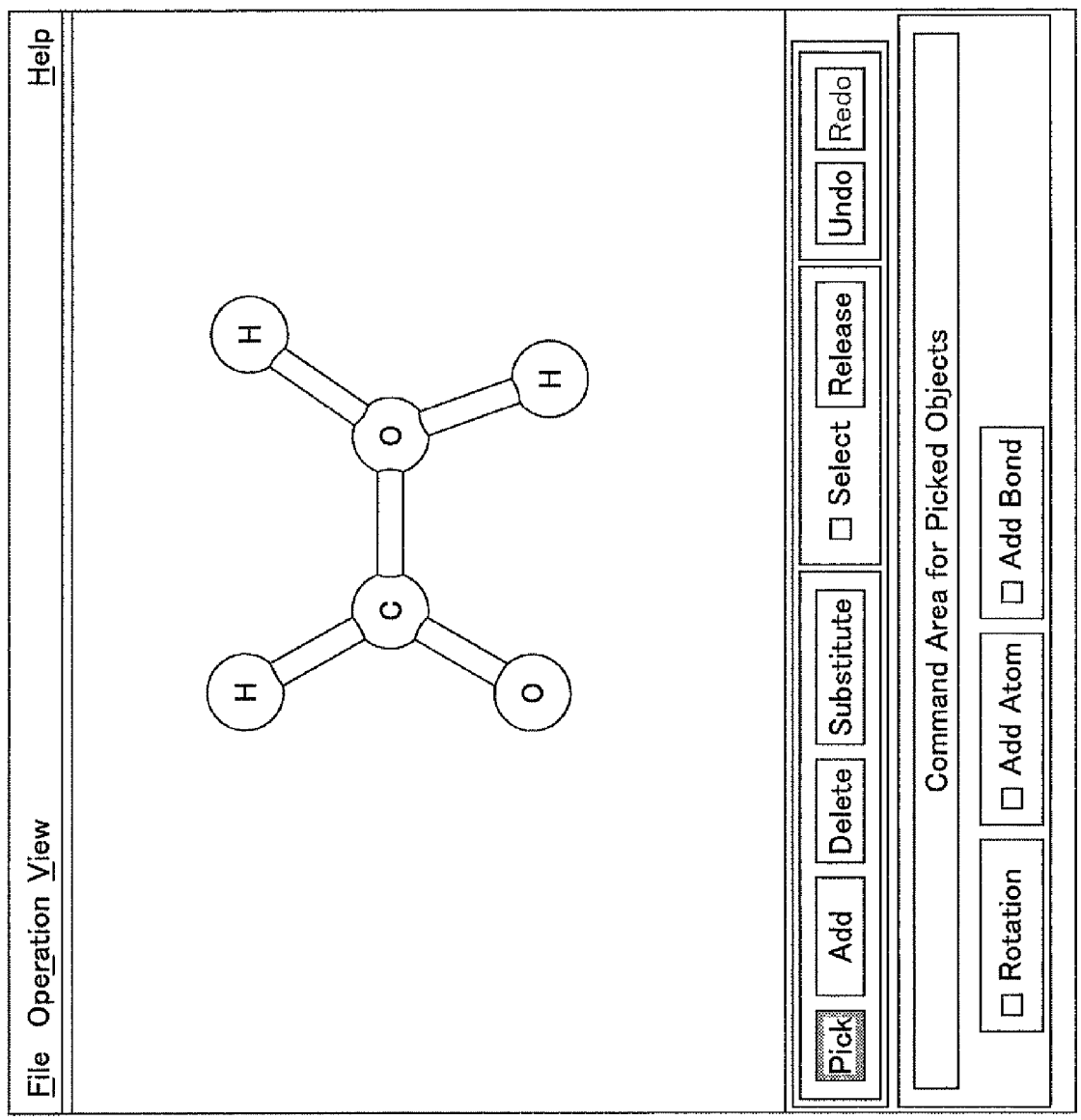
FIG. 68 is a diagram illustrating a display state of the molecular structure after the new atom event.

FIG. 67 is a diagram illustrating a display state of the molecular structure on the display screen 102a before the new atom event, and FIG. 68 is a diagram illustrating a display state of the molecular structure on the display screen 102a after the new atom event. The Undo operation and the Redo operation cannot be performed in the state before the new atom event illustrated in FIG. 67. On the other hand, the Undo operation can be performed and the Redo operation cannot be performed in the state after the new atom event illustrated in FIG. 68.

Figure 69:
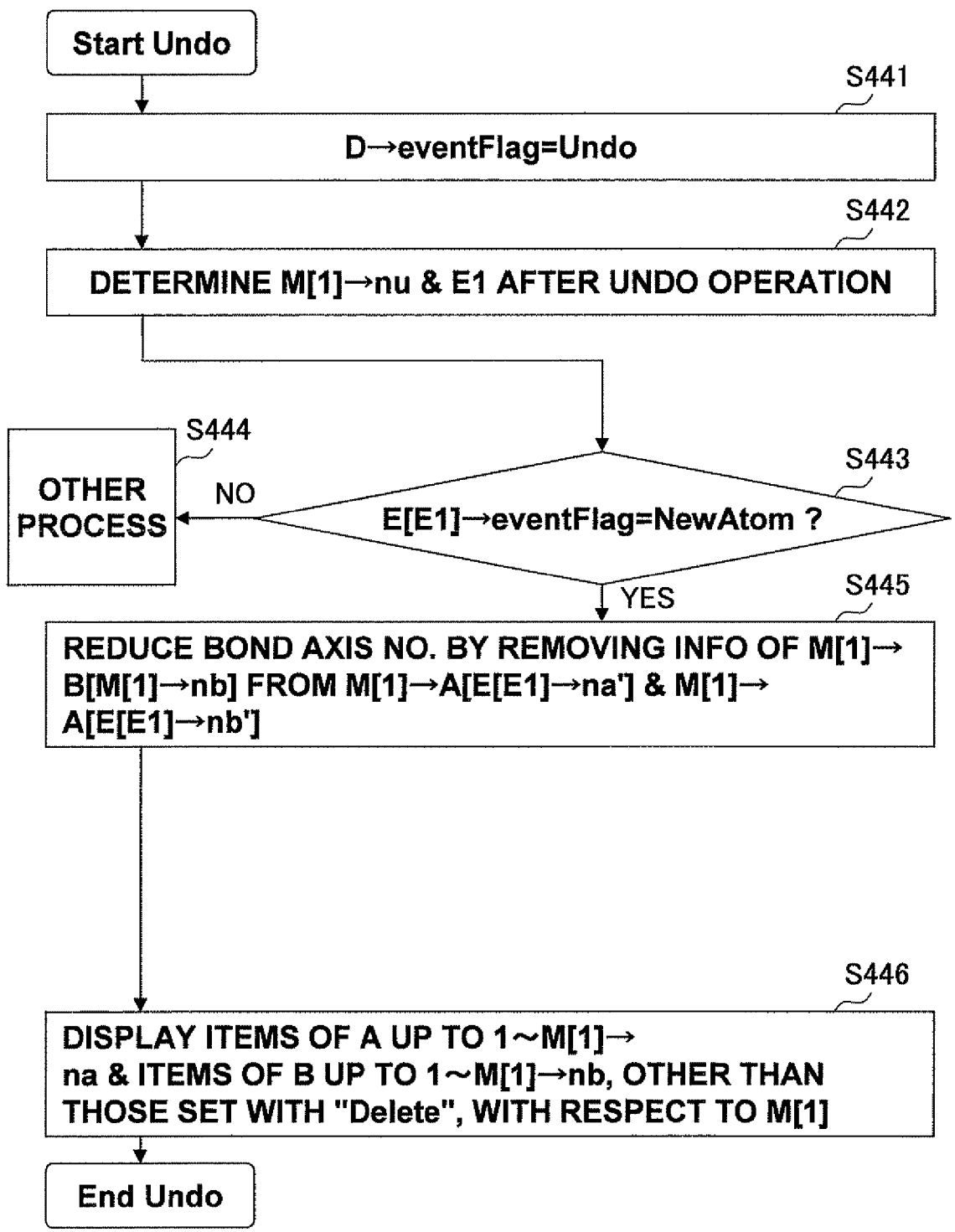
FIG. 69 is a flow chart for explaining an Undo operation of the new atom event.

FIG. 69 is a flow chart for explaining the Undo operation of the new atom event. When the Undo operation is started, a step S441 sets the event flag "eventFlag" of the auxiliary data to "Undo" according to D→eventFlag=Undo, based on a setting made by the user from the input part. A step S442 determines M[1]→nu and determines an event number E1 after the Undo operation, according to M[1]→nu=M[1]→nu+1 and E1=M[1]→ne-M[1]→nu+1. A step S443 decides whether E[E1]→eventFlag=NewAtom, and the process advances to a step S444 which performs another process that is not directly related to the subject matter of the present invention if the decision result is NO. On the other hand, the process advances to a step S445 if the decision result in the step S443 is YES.

The step S445 reduces the bond axis number by removing information of M[1]→B[M[1]→nb] from M[1]→A[E[E1]→na'] and M[1]→A[E[E1]→nb'], according to M[1]→A[E[E1]→na']→nb-1, M[1]→na=M[1]→na-1, and M[1]→nb=M[1]→nb-1. Further, a step S446 displays on the display screen 102a items of the atom A up to 1~M[1]→na and items of the bond axis B up to 1~M[1]→nb, other than those set with the delete bit "Delete", with respect to the molecular data M[1], and the Undo operation ends.

Figure 70:
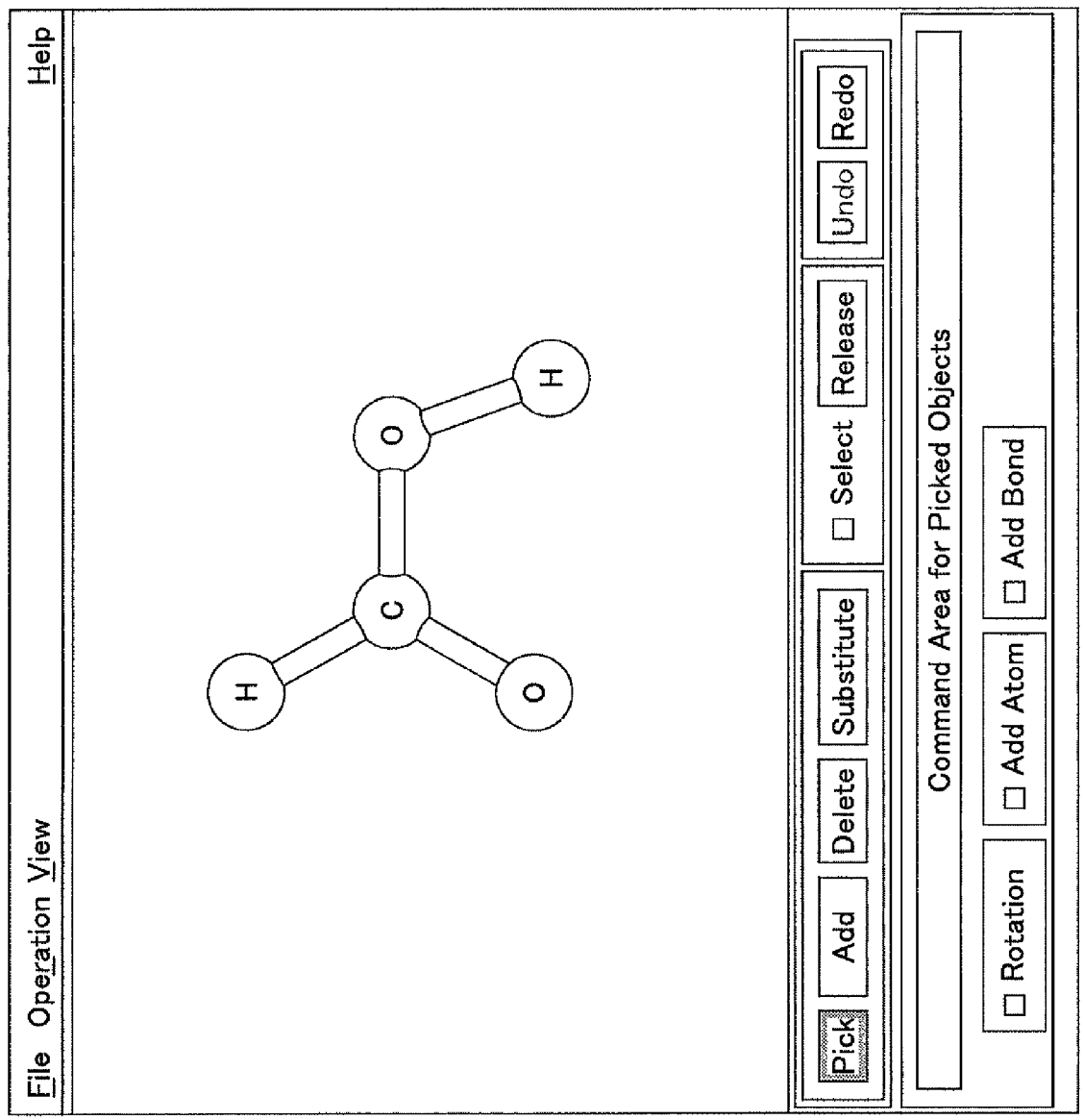
FIG. 70 is a diagram illustrating a display state of the molecular structure after the Undo operation.

FIG. 70 is a diagram illustrating a display state of the molecular structure on the display screen 102a after the Undo operation illustrated in FIG. 69. In the state after the Undo operation illustrated in FIG. 70, the Undo operation cannot be performed, but the Redo operation can be performed.

Figure 71:
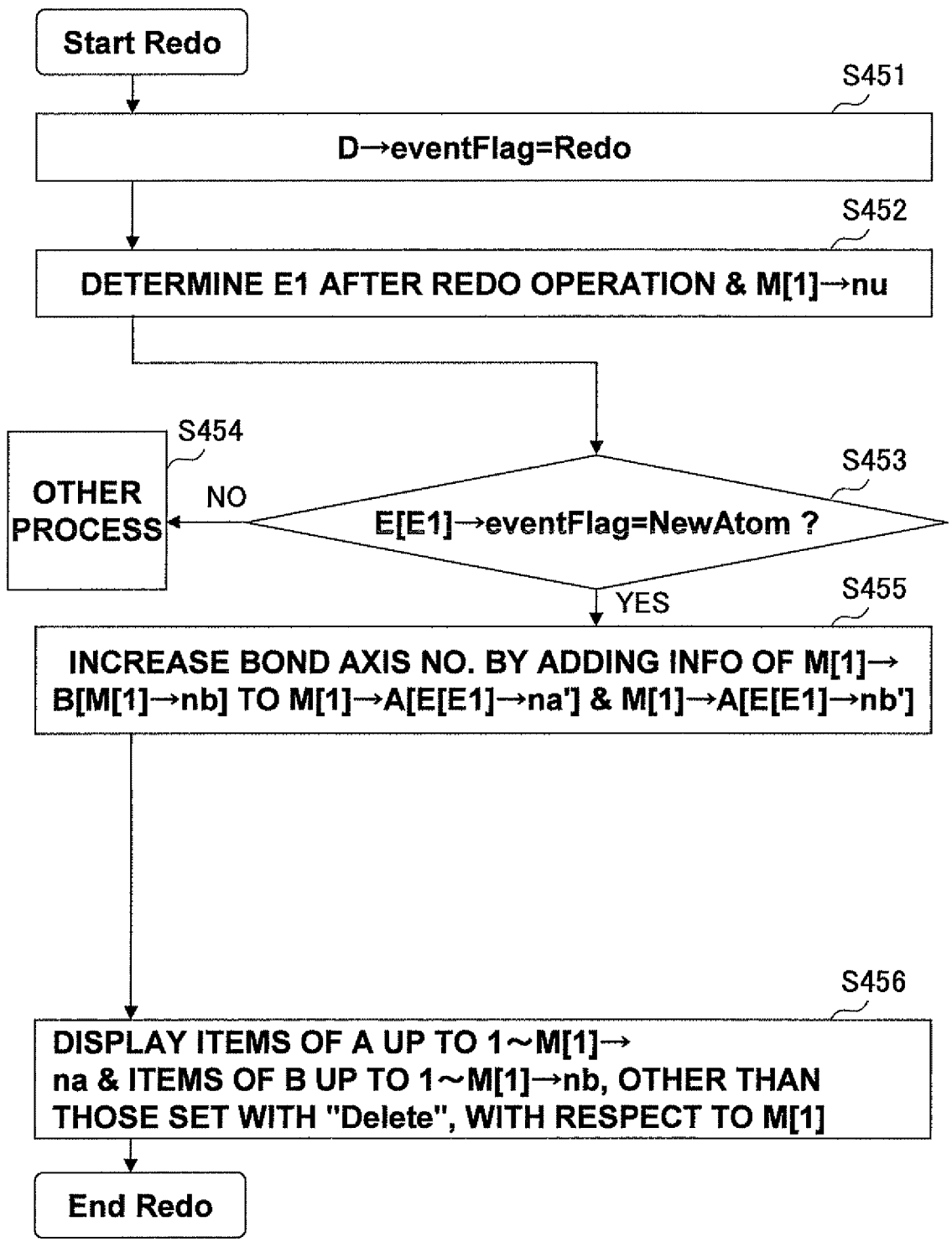
FIG. 71 is a flow chart for explaining a Redo operation of the new atom event.

FIG. 71 is a flow chart for explaining the Redo operation of the new atom event. When the Redo operation is started, a step S451 sets the event flag "eventFlag" of the auxiliary data to "Redo" according to D→eventFlag=Redo, based on a setting made by the user from the input part. A step S452 determines an event number E1 after the Redo operation and determines M[1]→nu, according to EM[1]=M[1]→ne−M[1]→nu+1 and M[1]→nu=M[1]→nu-1. A step S453 decides whether E[E1]→eventFlag=NewAtom, and the process advances to a step S454 which performs another process that is not directly related to the subject matter of the present invention if the decision result is NO. On the other hand, the process advances to a step S455 if the decision result in the step S453 is YES.

The step S455 increases the bond axis number by adding the information of M[1]→B[M[1]→nb] to M[1]→A[E[E1]→na'] and M[1]→A[E[E1]→nb'], according to M[1]→na=M[1]→na+1, M[1]→nb=M[1]→nb+1, and M[1]→A[E[E1]→na']→nb+1. Further, a step S456 displays on the display screen 102a items of the atom A up to 1~M[1]→na and items of the bond axis B up to 1~M[1]→nb, other than those set with the delete bit "Delete", with respect to the molecular data M[1], and the Redo operation ends.

Figure 72:
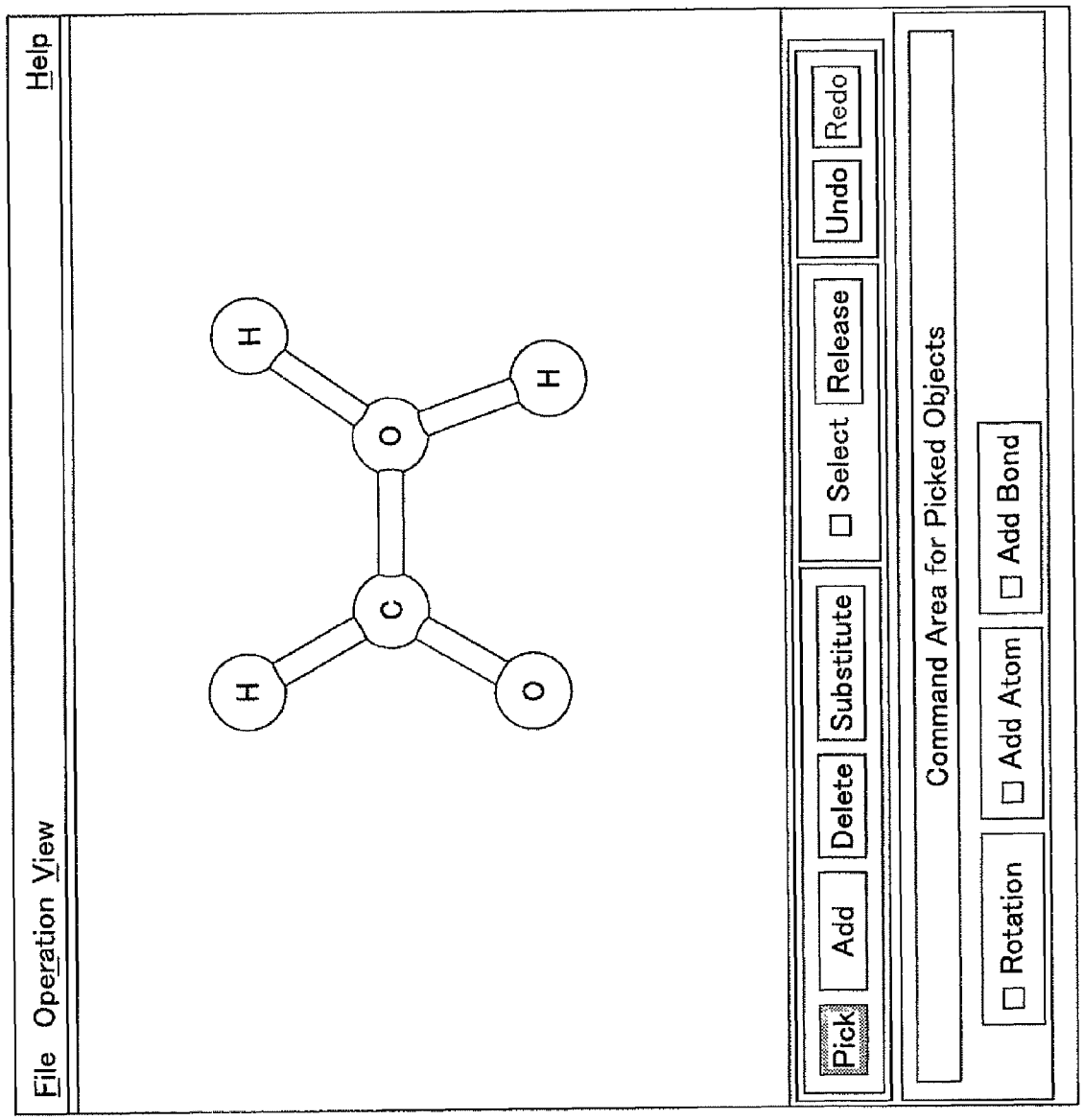
FIG. 72 is a diagram illustrating a display state of the molecular structure after the Redo operation.

FIG. 72 is a diagram illustrating a display state of the molecular structure on the display screen 102a after the Redo operation illustrated in FIG. 71. In the state after the Redo operation illustrated in FIG. 72, the Undo operation can be performed, but the Redo operation cannot be performed.

FIG. 73 is a diagram comparing data structures of the embodiment and the conventional example. As may be seen from FIG. 73, the embodiment greatly differs from the conventional example in that the embodiment employs the data structure illustrated in FIG. 1 including the atomic data structure "A", the bond axis data structure "B", the molecular data structure "M", the auxiliary data structure "D", and the event data structure "E".

FIG. 74 is a diagram comparing effects of the embodiment and the conventional example. It is assumed for the sake of convenience in FIG. 74 that the initial atom number is "n", the initial bond axis number is "nb", the storage capacity of the storage part (or GUI memory) for the atomic sphere is "x" bytes, the storage capacity of the storage part (or GUI memory) for the bond axis is "y" bytes, and the embodiment and the conventional example employ the data structures illustrated in FIG. 73. In addition, for the sake of convenience, the capacity of the storage part (or GUI memory) required for the atom items and the bond axis items is neglected, and it is assumed that the atom number is 1000, the bond axis number is 1000, and the new atom event (or new atom adding event) for which the Undo operation and the Redo operation are possible is repeated 1000 times. Furthermore, the storage capacity required for the new atom event for which the Undo operation and the Redo operation are possible was computed by setting the storage capacity "x" for the atomic sphere to zero, the storage capacity "y" for the bond axis to zero, and the other necessary constants "a", "b" and "c" to zero. As a result, it was confirmed that the required storage capacity can be reduced to approximately 1/776 that required by the conventional example, by using the data structure of the embodiment described above. In other words, it was confirmed that the embodiment enables the Undo operation and the Redo operation using an extremely small storage capacity compared to the conventional example.

By employing the data structure of the embodiment, it is possible to perform theoretical chemistry computations including molecular orbit computations, molecular dynamics computations and the like in high-tech research, such as drug design.

All examples and conditional language recited herein are intended for pedagogical purposes to aid the reader in understanding the invention and the concepts contribute by the inventor to furthering the art, and are to be construed as being without limitation to such specifically recited examples and conditions, nor does the organization of such examples in the specification related to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A molecular design method to be implemented in a computer to perform a design process by the computer, said molecular design method comprising:

constructing, by the computer, a data structure including an atomic data structure "A" related to an atom, a bond axis data structure "B" related to a bond axis, a molecular data structure "M" related to a molecule, an auxiliary data structure "D" assisting an event operation that includes a molecular structure modifying operation, and an event data structure "E" related to event information data, with respect to data of a given three-dimensional molecular structure, and storing, by the computer, the data structure in a storage part that is coupled to the computer;

displaying, by the computer, the three-dimensional molecular structure on a screen of a display in one of a half vector format, a ball-and-stick format and a space fill format;

determining, by the computer, a partial structure that is a modifying target using the data structure, based on an atom or a bond axis that is specified from an input part;

displaying, by the computer, a modified three-dimensional molecular structure in which the partial structure that is the modifying target has been subjected to a molecular structure modifying operation specified from the input part on the screen of the display; and performing, by the computer, an Undo or Redo operation on the molecular structure modifying operation specified from the input part using the data structure, wherein the atomic data structure "A" and the bond axis data structure "B" respectively include data having a 1:1 correspondence with each atom and each bond axis, the molecular data structure "M" includes an Undo event operation number, and each of the atomic data structure "A", the bond axis data structure "B", the molecular data structure "M", the auxiliary data structure "D", and the event data structure "E" includes an event flag.

2. The molecular design method as claimed in claim 1, wherein:
the atomic data structure "A" is represented by A={a, {Atom}, nb, {b[nb]}, eventFlag, {coordinate}}, where "a" denotes an identification number made up of an atomic sequence number in an internal coordinate, "Atom" denotes an atomic number made up of a chemical symbol, "nb" denotes a bond axis number made up of a numerical value which varies when an arbitrary new molecular structure is added to an original molecule, "b" denotes an identification number of the bond axis made up of data of a set of identification numbers of each of bond axes included in the bond axis number "nb", "eventFlag" denotes an event flag indicating a kind of a present event operation with respect to an event operation of a molecular structure constructing GUI and includes at least a delete operation, an add operation, a substitute operation, a new bond operation and a new atom operation, "coordinate" denotes xyz coordinates indicating Cartesian coordinates and includes data indicating a position of each atom existing in a three-dimensional space;
the bond axis data structure "B" is represented by B={b, {a[2]}, eventFlag, {vector}, length}, where "b" denotes an identification number made up of a number necessary to make a 1:1 correspondence for all of the bond axes, "a" denotes an identification number of a terminal atom and is made up of data of a set of identification numbers of the atoms existing at both ends of the bond axis, "vector" denotes vector information indicating a 1:1 correspondence of the bond axis and a three-dimensional vector, "length" denotes a bond axis length indicating a length of the bond axis when the vector information "vector" is represented by a unit vector;
the molecular data structure "M" is represented by M={na, nb, ne, nu, {A[na]}, {B[nb]}}, where "na" denotes an atomic data number, "nb" denotes a bond axis data number, "ne" denotes a total event operation number, "nu" denote an Undo event operation number, "A" denotes an atomic data within the molecule, and "B" denotes a bond axis data within the molecule;
the auxiliary data structure "D" is represented by D={eventFlag, {Atom}, {mSelect}, a}, where "mSelect" denotes molecule setting information corresponding to atomic setting information after substitution by a substitute operation or an added partial structure of an add operation, "a" denotes identification information of an added atom in order to identify a bond position of the add operation with respect to the original molecular structure; and
the event data structure "E" is represented by E={eventFlag, na', nb', na, nb, {A[na']}, {B[nb']}, {A'}, {B'}}, where "na'" denotes a selected atom number indicating a position of an atom that is specified in order to determine an operation position of the event operation, "nb'" denotes a selected bond axis number indicating a position of a bond axis that is specified in order to determine an operation position of the event operation, "na" denotes an added atom data number indicating the number of atoms within the partial structure related to the add operation, "nb" denotes a bond axis data number indicating the number of bond axes within the partial structure related to the add operation, "A" denotes an atomic data indicating the atomic data structure before the event operation, "B" denotes a bond axis data indicating the bond axis data structure before the event operation, "A'" denotes an atomic data indicating the atomic data structure after the event operation, and "B'" denotes a bond axis data indicating the bond axis data structure after the event operation.

3. The molecular design method as claimed in claim 1, wherein, when the molecular structure modifying operation is a delete operation which deletes the partial structure from the three-dimensional molecular structure, said displaying the modified three-dimensional molecular structure determines the partial structure that is a delete target and displays on the screen of the display a new molecular structure which has been deleted of the partial structure, based on the bond axis in the half vector format or, the atom or the atom and the bond axis in the ball-and-stick format or, the atom in the space fill format specified from the input part.

4. The molecular design method as claimed in claim 1, wherein, when the molecular structure modifying operation is a substitute operation which substitutes the partial structure of the three-dimensional molecular structure, said displaying the modified three-dimensional molecular structure determines the partial structure that is a substitute target and displays on the screen of the display a new molecular structure which has been substituted of the partial structure, based on the atom in the ball-and-stick format or, the atom in the space fill format specified from the input part.

5. The molecular design method as claimed in claim 1, wherein, when the molecular structure modifying operation is an add operation which adds the partial structure in place of a position of a certain atom in the three-dimensional molecular structure, said displaying the modified three-dimensional molecular structure determines a position where a target partial structure is to be added and displays on the screen of the display a new molecular structure which has been added with the target partial structure in place of the certain atom, based on the bond axis in the half vector format or, the atom in the ball-and-stick format or, the atom in the space fill format specified from the input part.

6. The molecular design method as claimed in claim 1, wherein, when the molecular structure modifying operation is a new bond operation which adds a new bond axis to the three-dimensional molecular structure, said displaying the modified three-dimensional molecular structure determines positions of two target atoms that are to be added with the new bond axis and displays on the screen of the display a new molecular structure which has been added with the new bond axis, based on the two target atoms in the ball-and-stick format specified from the input part.

7. The molecular design method as claimed in claim 1, wherein, when the molecular structure modifying operation is a new atom operation which adds a new atom to the three-dimensional molecular structure, said displaying the modified three-dimensional molecular structure determines a position where the new atom is to be added and displays on the screen of the display a new molecular structure which has been added with the new atom, based on the new atom in the ball-and-stick format or the space fill format specified from the input part.

8. A non-transitory computer-readable storage medium which stores a program which, when executed by a computer, causes the computer to perform a process comprising:
constructing a data structure including an atomic data structure "A" related to an atom, a bond axis data structure "B" related to a bond axis, a molecular data structure "M" related to a molecule, an auxiliary data structure "D" assisting an event operation that includes a molecular structure modifying operation, and an event data structure "E" related to event information data, with respect to data of a given three-dimensional molecular structure, and storing the data structure in a storage part that is coupled to the computer;

displaying the three-dimensional molecular structure on a screen of a display in one of a half vector format, a ball-and-stick format and a space fill format;

determining a partial structure that is a modifying target using the data structure, based on an atom or a bond axis that is specified from an input part;

displaying a modified three-dimensional molecular structure in which the partial structure that is the modifying target has been subjected to a molecular structure modifying operation specified from the input part on the screen of the display; and performing an Undo or Redo operation on the molecular structure modifying operation specified from the input part using the data structure, wherein the atomic data structure "A" and the bond axis data structure "B" respectively include data having a 1:1 correspondence with each atom and each bond axis, the molecular data structure "M" includes an Undo event operation number, and each of the atomic data structure "A", the bond axis data structure "B", the molecular data structure "M", the auxiliary data structure "D", and the event data structure "E" includes an event flag.

9. The non-transitory computer-readable storage medium as claimed in claim 8, wherein:

the atomic data structure "A" is represented by A={a, {Atom}, nb, {b[nb]}, eventFlag, {coordinate}}, where "a" denotes an identification number made up of an atomic sequence number in an internal coordinate, "Atom" denotes an atomic number made up of a chemical symbol, "nb" denotes a bond axis number made up of a numerical value which varies when an arbitrary new molecular structure is added to an original molecule, "b" denotes an identification number of the bond axis made up of data of a set of identification numbers of each of bond axes included in the bond axis number "nb", "eventFlag" denotes an event flag indicating a kind of a present event operation with respect to an event operation of a molecular structure constructing GUI and includes at least a delete operation, an add operation, a substitute operation, a new bond operation and a new atom operation, "coordinate" denotes xyz coordinates indicating Cartesian coordinates and includes data indicating a position of each atom existing in a three-dimensional space;

the bond axis data structure "B" is represented by B={b, {a[2]}, eventFlag, {vector}, length}, where "b" denotes an identification number made up of a number necessary to make a 1:1 correspondence for all of the bond axes, "a" denotes an identification number of a terminal atom and is made up of data of a set of identification numbers of the atoms existing at both ends of the bond axis, "vector" denotes vector information indicating a 1:1 correspondence of the bond axis and a three-dimensional vector, "length" denotes a bond axis length indicating a length of the bond axis when the vector information "vector" is represented by a unit vector;

the molecular data structure "M" is represented by M={na, nb, ne, nu, {A[na]}, {B[nb]}}, where "na" denotes an atomic data number, "nb" denotes a bond axis data number, "ne" denotes a total event operation number, "nu" denote an Undo event operation number, "A" denotes an atomic data within the molecule, and "B" denotes a bond axis data within the molecule;

the auxiliary data structure "D" is represented by D={eventFlag, {Atom}, {mSelect}, a}, where "mSelect" denotes molecule setting information corresponding to atomic setting information after substitution by a substitute operation or an added partial structure of an add operation, "a" denotes identification information of an added atom in order to identify a bond position of the add operation with respect to the original molecular structure; and the event data structure "E" is represented by E={eventFlag, na', nb', na, nb, {A[na']}, {B[nb']}, {A'}, {B'}}, where "na'" denotes a selected atom number indicating a position of an atom that is specified in order to determine an operation position of the event operation, "nb'" denotes a selected bond axis number indicating a position of a bond axis that is specified in order to determine an operation position of the event operation, "na" denotes an added atom data number indicating the number of atoms within the partial structure related to the add operation, "nb" denotes a bond axis data number indicating the number of bond axes within the partial structure related to the add operation, "A" denotes an atomic data indicating the atomic data structure before the event operation, "B" denotes a bond axis data indicating the bond axis data structure before the event operation, "A'" denotes an atomic data indicating the atomic data structure after the event operation, and "B'" denotes a bond axis data indicating the bond axis data structure after the event operation.

10. The non-transitory computer-readable storage medium as claimed in claim 8, wherein, when the molecular structure modifying operation is a delete operation which deletes the partial structure from the three-dimensional molecular structure, said displaying the modified three-dimensional molecular structure determines the partial structure that is a delete target and displays on the screen of the display a new molecular structure which has been deleted of the partial structure, based on the bond axis in the half vector format or, the atom or the atom and the bond axis in the ball-and-stick format or, the atom in the space fill format specified from the input part.

11. The non-transitory computer-readable storage medium as claimed in claim 8, wherein, when the molecular structure modifying operation is a substitute operation which substitutes the partial structure of the three-dimensional molecular structure, said displaying the modified three-dimensional molecular structure determines the partial structure that is a substitute target and displays on the screen of the display a new molecular structure which has been substituted of the partial structure, based on the atom in the ball-and-stick format or, the atom in the space fill format specified from the input part.

12. The non-transitory computer-readable storage medium as claimed in claim 8, wherein, when the molecular structure modifying operation is an add operation which adds the partial structure in place of a position of a certain atom in the three-dimensional molecular structure, said displaying the modified three-dimensional molecular structure determines a position where a target partial structure is to be added and displays on the screen of the display a new molecular structure which has been added with the target partial structure in place of the certain atom, based on the bond axis in the half vector format or, the atom in the ball-and-stick format or, the atom in the space fill format specified from the input part.

13. The non-transitory computer-readable storage medium as claimed in claim 8, wherein, when the molecular structure modifying operation is a new bond operation which adds a new bond axis to the three-dimensional molecular structure, said displaying the modified three-dimensional molecular structure determines positions of two target atoms that are to be added with the new bond axis and displays on the screen of the display a new molecular structure which has been added with the new bond axis, based on the two target atoms in the ball-and-stick format specified from the input part.

14. The non-transitory computer-readable storage medium as claimed in claim 8, wherein, when the molecular structure modifying operation is a new atom operation which adds a new atom to the three-dimensional molecular structure, said displaying the modified three-dimensional molecular structure determines a position where the new atom is to be added and displays on the screen of the display a new molecular structure which has been added with the new atom, based on the new atom in the ball-and-stick format or the space fill format specified from the input part.

* * * * *